United States Patent
Micol

(10) Patent No.: US 12,195,746 B2
(45) Date of Patent: Jan. 14, 2025

(54) COMPOSITIONS AND PROCESSES FOR TARGETED DELIVERY, EXPRESSION AND MODULATION OF CODING RIBONUCLEIC ACIDS IN TISSUE

(71) Applicant: Combined Therapeutics, Inc., Wilmington, DE (US)

(72) Inventor: Romain Micol, London (GB)

(73) Assignee: Combined Therapeutics, Inc., Wilmington, DE (US)

( * ) Notice: Subject to any disclaimer, the term of this patent is extended or adjusted under 35 U.S.C. 154(b) by 0 days.

(21) Appl. No.: 17/706,522

(22) Filed: Mar. 28, 2022

(65) Prior Publication Data

US 2022/0220506 A1 Jul. 14, 2022

Related U.S. Application Data

(63) Continuation of application No. 16/811,504, filed on Mar. 6, 2020, now Pat. No. 11,359,212, which is a continuation of application No. PCT/US2018/049772, filed on Sep. 6, 2018.

(60) Provisional application No. 62/632,056, filed on Feb. 19, 2018.

(30) Foreign Application Priority Data

Sep. 7, 2017 (GB) .................................. 1714430

(51) Int. Cl.
| | |
|---|---|
| C12N 15/86 | (2006.01) |
| A61K 31/7088 | (2006.01) |
| A61K 35/763 | (2015.01) |
| A61K 45/06 | (2006.01) |
| A61K 48/00 | (2006.01) |

(52) U.S. Cl.
CPC .......... *C12N 15/86* (2013.01); *A61K 31/7088* (2013.01); *A61K 35/763* (2013.01); *A61K 45/06* (2013.01); *A61K 48/0058* (2013.01); *C12N 2310/141* (2013.01); *C12N 2710/16632* (2013.01); *C12N 2710/16643* (2013.01)

(58) Field of Classification Search
None
See application file for complete search history.

(56) References Cited

U.S. PATENT DOCUMENTS

| | | | |
|---|---|---|---|
| 10,688,164 B2* | 6/2020 | Nelson | A61P 33/00 |
| 11,359,212 B2* | 6/2022 | Micol | A61K 48/0058 |
| 11,596,685 B2* | 3/2023 | Micol | A61K 31/7088 |
| 11,931,409 B2* | 3/2024 | Micol | A61K 31/7105 |
| 2003/0170838 A1 | 9/2003 | Mishra et al. | |
| 2005/0261218 A1 | 11/2005 | Esau et al. | |
| 2010/0197772 A1 | 8/2010 | Califano et al. | |
| 2013/0156849 A1 | 6/2013 | De Fougerolles et al. | |
| 2014/0147454 A1* | 5/2014 | Chakraborty | C12N 15/67 536/23.1 |
| 2016/0089453 A1 | 3/2016 | Zamore et al. | |
| 2018/0311343 A1 | 11/2018 | Huang et al. | |
| 2020/0255863 A1 | 8/2020 | Micol et al. | |
| 2020/0376142 A1 | 12/2020 | Micol | |

FOREIGN PATENT DOCUMENTS

| | | |
|---|---|---|
| WO | WO 2013090648 A1 | 6/2013 |
| WO | WO 2013/126712 A1 | 8/2013 |
| WO | WO 2015/058069 A1 | 4/2015 |
| WO | WO 2015/070060 A1 | 5/2015 |
| WO | WO 2016/011306 A2 | 1/2016 |
| WO | WO 2016/100812 A1 | 6/2016 |
| WO | WO 2017/062513 A1 | 4/2017 |
| WO | WO 2017/132552 A1 | 8/2017 |
| WO | WO 2018/115527 A2 | 6/2018 |
| WO | WO 2019/158955 A1 | 8/2019 |

OTHER PUBLICATIONS

Criscitiello et al. Breast Care 7:262-266 (Year: 2012).*
JP Office Action in Japanese Application No. 2020-536493, dated Aug. 16, 2022, 9 pages (with English translation).
Ruiz et al., "MicroRNAs and oncolytic viruses", Current Opinion in Virology, Apr. 2015, 13:40-48.
Wroblewska et al., "Mammalian synthetic circuits with RNA binding proteins for RNA-only delivery". Nature Biotechnology, Aug. 2015, 33(8): 839-841.
Aghi et al., "Oncolytic herpes virus with defective ICP6 specifically replicates in quiescent cells with homozygous genetic mutations in p16," Oncogene, 27: 4249-4254 (2008).
Aref et al., "Measles to the Rescue: A Review of Oncolytic Measles Virus," Viruses, 8: 294 (2016).
Baker et al., "Designer Oncolytic Adenovirus: Coming of Age," Cancers, 10: 201 (2018).

(Continued)

*Primary Examiner* — Brian Whiteman
(74) *Attorney, Agent, or Firm* — DLA Piper LLP (US)

(57) ABSTRACT

A composition for expressing a polypeptide within a target organ including a delivery particle, and at least a first mRNA sequence complexed with, encapsulated by, or otherwise associated with the delivery particle. The mRNA sequence includes a coding sequence which codes for the polypeptide, at least a first untranslated region (UTR) sequence, and at least one micro-RNA (miRNA) binding site sequence, wherein the miRNA binding site sequence is located within, immediately 5' to, or immediately 3' to, the first UTR sequence. The miRNA binding site sequence is selected so as to provide for differential expression of the coding sequence between first and second cell types comprised within the target organ. Methods for making and using the composition are provided, particularly in treatment of disease, such as cancer.

10 Claims, 20 Drawing Sheets

Specification includes a Sequence Listing.

(56) References Cited

OTHER PUBLICATIONS

Baltimore, "Expression of Animal Virus Genomes," Bacteriological Reviews, 35(3): 235-241 (1971).
Braconi et al., The role of microRNAs in human liver cancers, Seminars in Oncology, 38(6):752-763 (2011).
Brown et al., "Exploiting and antagonizing microRNA regulation for therapeutic and experimental applications," Nature Reviews Genetics, 10: 578-585 (2009).
Brun et al., "Identification of Genetically Modified Maraba Virus as an Oncolytic Rhabdovirus," Molecular Therapy, 18(8): 1440-1449 (2010).
Chen et al., "Rapid Discovery of Potent siRNA-Containing Lipid Nanoparticles Enabled by Controlled Microfluidic Formulation," J. Am. Chem. Soc., 134: 6948-6951 (2012).
Cooper et al., "T-cell clones can be rendered specific for CD19: toward the selective augmentation of the graft-versus-B—lineage leukemia effect." Blood, 101(4): 1637-1644 (2003).
Coppola et al., "Lowered expression of microRNA-125a-5p in human hepatocellular carcinoma and up-regulation of its oncogenic targets sirtuin-7, matrix metalloproteinase-11, and c-Raf," Oncotarget, 8(15): 25289-25299 (2017).
Cotton et al., 142] Receptor-Mediated Transport of DNA into Eukaryotic Cells, Methods in Enzymology, 217: 618-644 (1993).
Edge et al., "A let-7 MicroRNA-sensitive Vesicular Stomatitis Virus Demonstrates Tumorspecific Replication," Molecular Therapy, 16(8): 1437-1443 (2008).
El Ouaamari et al., "miR-375 Targets 3' -Phosphoinositide-Dependent Protein Kinase-1 and Regulates Glucose-Induced Biological Responses in Pancreatic ?-Cells," Diabetes. 57: 2708-2717 (2008).
Felt et al., "Chitosan: A Unique Polysaccharide for Drug Delivery," Drug Development and Industrial Pharmacy, 24(11): 979-993 (1998).
Fiume et al., "Targeting of antiviral drugs to the liver using glycoprotein carriers," Advanced Drug Delivery Reviews, 14: 51-65 (1994).
Gao et al., "An insertion/deletion polymorphism at miRNA-122-binding site in the interleukin-1 3' untranslated region confers risk for hepatocellular carcinoma," Carcinogenesis, 30(12): 2064-2069 ,2009).
Goldsmith et al., "Infected Cell Protein (ICP)47 Enhances Herpes Simplex Virus Neurovirulence by Blocking the CD81 T Cell Response," J. Exp. Med., 187(3): 341-348 (1998).
Hamad et al., "Demonstration of the Presence of the "Deleted" MIR122 Gene in HepG2 Cells," PLoS One, 10(3): e0122471 (2015).
Haralambieva et al.. "Engineering Oncolytic Measles Virus to Circumvent the Intracellular Innate Immune Response," Molecular Therapy. 15(3): 588-597 (2007).
International Search Report and Written Opinion for International Application No. PCT/GB2019/050454 dated May 8, 2019.
International Search Report and Written Opinion for International Application No. PCT/US2018/049772 mailed Dec. 19, 2018.
Jena et al., "Redirecting T-cell specificity by introducing a tumor-specific chimeric antigen receptor," Blood, 116(7): 1035-1044 (2010).
Kaczmarek et al., "Polymer-Lipid Nanoparticles for Systemic Delivery of mRNA to the Lungs," Angew Chem Int Ed Engl., 55(44): 13808-13812 (2016).
Kasuya et al., "Suitability of a US3-inactivated HSV mutant (L1BR1) as an oncolytic virus for pancreatic cancer therapy," Cancer Gene Therapy, 14: 533-542 (2007).
Kauffman et al., "Optimization of Lipid Nanoparticle Formulations for mRNA Delivery in Vivo with Fractional Factorial and Definitive Screening Designs," Nano Lett.. 15: 7300-7306 (2015).
Kutay et al.. "Downregulation of miR-122 in the Rodent and Human Hepatocellular Carcinomas," J Cell Biochem., 99(3): 671-678 (2006).
Lagos-Quintana et al., "Identification of Tissue-Specific MicroRNAs from Mouse," Current Biology, 12: 735-739 (2002).
Leopardi et al.. "The herpes simplex virus 1 protein kinase US3 is required for protection from apoptosis induced by the?virus," Proc. Natl. Acad. Sci. USA, 94: 7891-7896 (1997).
Liu et al., "ICP34.5 deleted herpes simplex virus with enhanced oncolytic, immune stimulating, and anti-tumour properties." Gene Therapy, 10: 292-303 (2003).
Lohcharoenkal et al., "Protein Nanoparticles as Drug Delivery Carriers for Cancer Therapy," BioMed Research International, vol. 2014, Article ID 180549, 12 pages (2014).
Lui et al., "Patterns of Known and Novel Small RNAs in Human Cervical Cancer," Cancer Res, 67: 6031-6043 (2007).
Marchini et al., "Oncolytic parvoviruses: from basic virology to clinical applications," Virology Journal, 12:6 (2015).
Mazzacurati et al., "Use of miRNA Response Sequences to Block Off-target Replication and Increase the Safety of an Unattenuated, Glioblastoma-targeted Oncolytic HSV," Molecular Therapy, 23(1): 99-107 (2015).
Moffett et al., "Hit-and-run programming of therapeutic cytoreagents using mRNA nanocarriers," Nature Communications, 8: Article No. 389 (2017).
Nicholson et al., "Construction and Characterisation of a Functional CD19 Specific Single Chain Fv Fragment fFor Immunotherapy of B Lineage Leukaemia and Lymphoma," Molecular Immunology, 34(16-17): 1157-1165 (1997).
Nygaard et al., "Identification and analysis of miRNAs in human breast cancer and teratoma samples using deep sequencing," BMC Medical Genomics, 2:35 (2009).
Park et al., "Treating Cancer with Genetically Engineered T Cells," Trends Biotechnol., 29(11): 550-557 (2011).
PCT International Search Report and Written Opinion in International Application No. PCT/US2021/043975, dated Dec. 6, 2021, 13 pages.
Russell et al., "Oncolytic Virotherapy," Nat. Biotechnol., 30(7): 658-670 (2014).
Singh et al. Indian J Med Res. Oct. 2012; 136(4): 571-584 (Year: 2012).
Song et al., "Expression levels of microRNA-375 in pancreatic cancer," Biomedical Reports, 1: 393-398 (2013).
Vigil et al., "Use of Reverse Genetics to Enhance the Oncolytic Properties of Newcastle Disease Virus," Cancer Res, 67(17): 8285-8292 (2007).
Wagner et al., "Delivery of drugs, proteins and genes into cells using transferrin as a ligand for receptor-mediated endocytosis," Advanced Drug Delivery Reviews, 14: 113-135 (1994).
Watahiki et al., "MicroRNAs Associated with Metastatic Prostate Cancer," PLoS One 6(9): e24950 (2011).
Wyman et al., "Repertoire of microRNAs in Epithelial Ovarian Cancer as Determined by Next Generation Sequencing of Small RNA cDNA Libraries," PLoS One 4(4): e5311 (2009).
Yu et al., "let-7 Regulates Self Renewal and Tumorigenicity of Breast Cancer Cells," Cell, 131; 1109-1123 (2007).
Zhang et al., "Wuhan seafood market pneumonia virus isolate Wuhan-Hu-1, complete genome", Database EMBL, MN908947, Jan. 15, 2020, 15 pages.

* cited by examiner

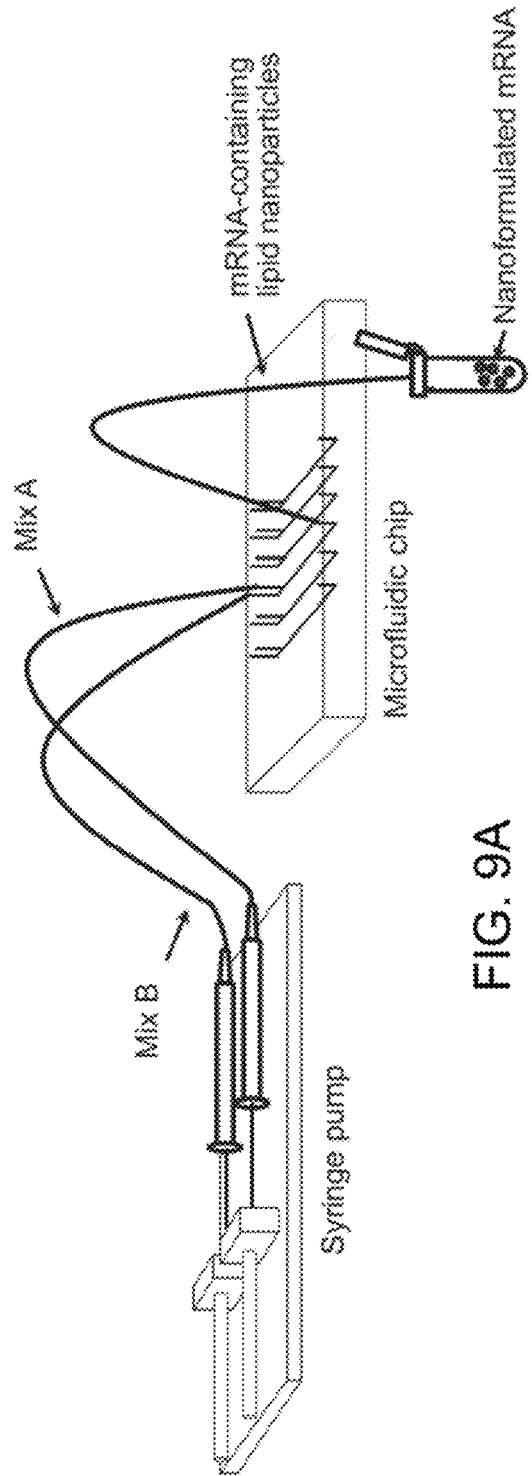
FIG. 9A
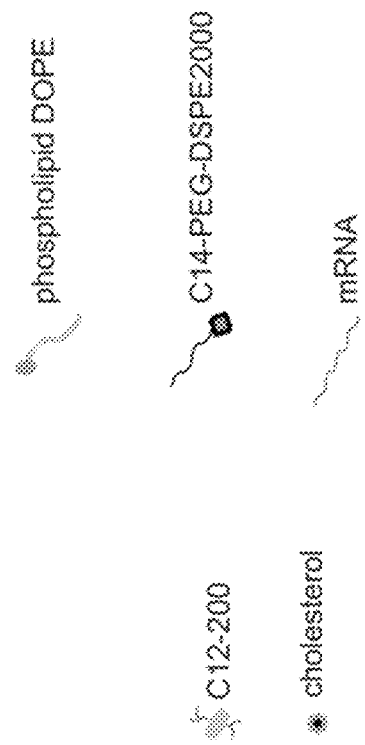
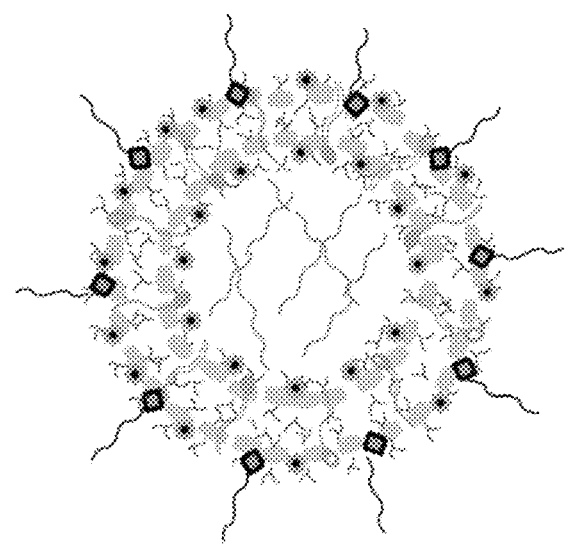
FIG. 9B

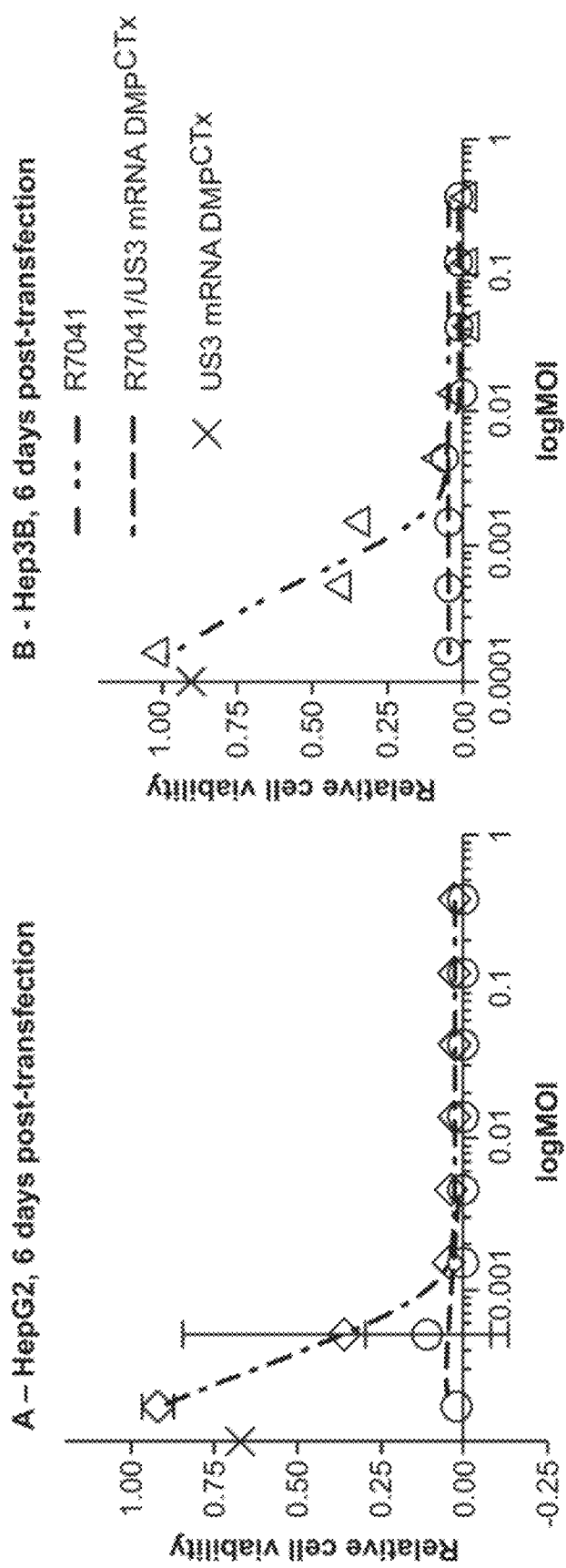

SEQUENCE LISTING

```
<160> NUMBER OF SEQ ID NOS: 5

<210> SEQ ID NO 1
<211> LENGTH: 22
<212> TYPE: RNA
<213> ORGANISM: Artificial Sequence
<220> FEATURE:
<223> OTHER INFORMATION: single miR122 binding site

<400> SEQUENCE: 1
aacgccauua ucacacuaaa ua                                              22

<210> SEQ ID NO 2
<211> LENGTH: 50
<212> TYPE: RNA
<213> ORGANISM: Artificial Sequence
<220> FEATURE:
<223> OTHER INFORMATION: 2x miR-122 binding sites with linker

<400> SEQUENCE: 2
aacgccauua ucacacuaaa uauuuaaaaa cgccauuauc acacuaaaua               50

<210> SEQ ID NO 3
<211> LENGTH: 761
<212> TYPE: RNA
<213> ORGANISM: Artificial Sequence
<220> FEATURE:
<223> OTHER INFORMATION: mCherry sequence with 2x miR-122 binding
      sequence and linker

<400> SEQUENCE: 3
auggugagca agggcgagga ggauaacaug gccaucauca aggaguucau gcgcuucaag      60
gugcacaugg agggcuccgu gaacggccac gaguucgaga ucgagggcga gggcgagggc    120
cgccccuacg agggcaccca gaccgccaag cugaaggugu ccaagggugg cccccugccc    180
uucgccuggg acauccuguc cccucaguuc auguacggcu ccaaggccua cgugaagcac    240
cccgccgaca uccccgacua cuugaagcug uccuucccgg agggcuucaa gugggagcgc    300
gugaugaacu ucgaggacgg cggcguggug accgugaccc aggacuccuc ccugcaggac    360
ggcgaguuca ucuacaaggu gaagcugcgc ggcaccaacu uccccuccga cggccccgua    420
augcagaaga agaccauggg cugggaggcc uccuccgagc ggauguaccc cgaggacggc    480
gcccugaagg gcgagaucaa gcagaggcug aagcugaagg acggcggcca cuacgacgcu    540
gaggucaaga ccaccuacaa ggccaagaag cccgugcagc ugcccggcgc cuacaacguc    600
```

| | |
|---|---|
| aacaucaagu uggacaucac cucccacaac gaggacuaca ccaucgugga acaguacgaa | 660 |
| cgcgccgagg gccgccacuc caccggcggc auggacgagc uguacaagua aaacgccauu | 720 |
| aucacacuaa auauuuaaaa acgccauuau cacacuaaau a | 761 |

```
<210> SEQ ID NO 4
<211> LENGTH: 1496
<212> TYPE: RNA
<213> ORGANISM: Artificial Sequence
<220> FEATURE:
<223> OTHER INFORMATION: US3 with 2x miR-122 binding sites and linker

<400> SEQUENCE: 4
```

| | |
|---|---|
| auggccuguc guaaguuuug ucgcguuuac ggggggacagg gcaggaggaa ggaggaggcc | 60 |
| gucccgccgg agacaaagcc gucccgggug uuuccucaug gccccuuuua uaccccagcc | 120 |
| gaggacgcgu gccuggacuc cccgcccccg gagaccccca aaccuuccca caccacacca | 180 |
| cccggcgaug ccgagcgccu gugucaucug caggagaucc uggcccagau guacggaaac | 240 |
| caggacuacc ccauagagga cgaccccagc gcggaugccg gacgaugu cgacgaggac | 300 |
| gccccggacg acguggccua uccggaggaa uacgcagagg agcuuuucu gcccggggac | 360 |
| gcgcccgguc cccuuaucgg ggccaacgac cacaucccuc ccccgugugg cgcaucuccc | 420 |
| cccguauac gacgacgcag ccgggaugag auuggggcca cgggauuuac cgcggaagaa | 480 |
| cuggacgcca uggacaggga ggcggcucga gccaucagcc gcggcggcaa gccccccucg | 540 |
| accauggcca agcuggugac uggcaugggc uuuacgaucc acggagcgcu caccccagga | 600 |
| ucggaggggu gugucuuuga cagcagccac ccagauuacc cccaacgggu aaucgugaag | 660 |
| gcggggguggu acacgagcac gagccacgag gcgcgacugc ugaggcgacu ggaccacccc | 720 |
| gcgauccugc cccuccugga ccugcaugc gucuccgggg ucacguguc ugguccucccc | 780 |
| aaguaccagg ccgaccugua uccuaucug aguaggcgcc ugaacccgcu gggacgcccg | 840 |
| cagaucgcag cggucucccg gcagcuccua agcgccguug acuacauuca ccgccagggc | 900 |
| auuauccacc gcgacauuaa gaccgaaaau auuuuauua acaccccga ggacauuugc | 960 |
| cugggggacu uuggugccgc gugcuucgug cagggguuccc gaucaagccc cuuccccuac | 1020 |
| ggaaucgccg gaaccaucga caccaacgcc cccgaggucc ugaccgggga uccguauacc | 1080 |
| accaccgucg acauuuggag cgccggucug gugaucuucg agacugccgu ccacaacgcg | 1140 |
| uccuuguucu cggcccccccg cggccccaaa aggggcccgu gcgacaguca gaucacccgc | 1200 |
| aucauccgac aggcccaggu ccacguugac gaguuuuccc cgcauccaga aucgcgccuc | 1260 |
| accucgcgcu accgcucccg cgcggccggg aacaaucgcc gccguacac ccgaccggcc | 1320 |
| uggacccgcu acuacaagau ggacauagac gucgaauauc ugguuugcaa agcccucacc | 1380 |
| uucgacggcg cgcuucgccc cagcgccgca gagcugcuuu guuugccgcu guuucaacag | 1440 |
| aaaugaaacg ccauuaucac acuaaauauu uaaaaacgcc auuaucacac uaaaua | 1496 |

```
<210> SEQ ID NO 5
<211> LENGTH: 3466
<212> TYPE: RNA
<213> ORGANISM: Artificial Sequence
<220> FEATURE:
<223> OTHER INFORMATION: ICP6 with 2x miRNA-122 binding site sequences

<400> SEQUENCE: 5
```

| | |
|---|---|
| augauggcca gccgcccagc cgcauccucu cccgucgaag cgcgggcccc gguuggggga | 60 |
| caggaggccg gcggcccag cgcagccacc caggggggagg ccgccggggc cccucucgcc | 120 |

```
cacggccacc acguguacug ccagcgaguc aauggcguga uggugcuuuc cgacaagacg   180
cccggguccg cguccuaccg caucagcgau agcaacuuug uccaaugugg uuccaacugc   240
accaugauua ucgacggaga cguggugcgc gggcgccccc aggacccggg ggccgcggca   300 uccccgcuc ccuucguugc ggugacaaac aucggagccg cagcgacgg cgggaccgcc    360 gucguugcau ucgggggaac cccacgucgc ucggcgggga cgucuaccgg uacccagacg   420
gccgacgucc cagccgaggc ccuuggggc ccccccuccuc ucccccgcuu cacccugggu   480
ggcggcuguu gcuccugucg gacacacgg cgccgcucug cgguauucgg ggggagggg    540 gaucccgucg gccccgcgga guucgucucg gacgaccggu cguccgauuc cgacucggau   600
gacucggagg acaccgacuc ggagacgcug ucacgcgccu ccucggacgu guccggcggg   660
gccacguacg acgacgcccu ugacuccgau ucgucaucgg augacucccu gcagauagau   720
ggccccgugu gucgccgug gagcaaugac accgcgcccc uggauguuug ccccgggacc    780
cccggcccgg gcgccgacgc cggguggucc ucagcgguag acccacacgc gccgacgaca   840
ggggccggcg cuggucuugc ggccgauccc gccguggccc gggacgacgc ggaggggcuu   900
ucggaccccc ggccacgucu gggaacgggc acggccuacc ccguccccu ggaacucacg    960 cccgagaacg cggaggccgu ggcgcgcuuu cugggagaug ccgugaaccg cgaacccgcg   1020
cucaugcugg aguacuuuug ccggugcgcc cgcgaggaaa ccaagcgugu cccccccagg   1080
acauucugca gccccccucg ccucacggag gacgacuuug ggcuucucaa cuacgcgcuc   1140
guggagaugc agcgccugug ucggacguu ccuccggucc cgccgaacgc auacaugccc    1200
uauuaucuca gggaguaugu gacgcggcug gucaacgggu caagccgcu ggugagccgg    1260 uccguucgcc uuuaccgcau ccuggggguu cuggugcacc ugcggauccg gacccgggag   1320
gccuccuuug aggaguggcu gcgauccaag gaaguggccc uggacuuugg ccugacggaa   1380
aggcuucgcg agcacgaagc ccagcuggug auccuggccc aggcucugga ccauuacgac   1440
ugucugaucc acagcacacc gcacacgcug gucgagcggg ggcugcaauc ggcccugaag   1500
uaugaggagu uuuaccuaaa gcgcuuuggc gggcacauaca uggagcucgu cuuccagaug   1560
uacacccgca ucgccggcuu uuuggccugc cgggccacgc gcggcaugcg ccacaucgcc   1620
cuggggcgag aggggucgug gugggaaaug uucaaguucu uuuuccaccg ccucuacgac   1680
caccagaucg uaccgucgac ccccgccaug cugaaccugg ggacccgcaa cuacuacacc   1740
uccagcugcu accugguaaa ccccccaggcc accacaaaca aggcgacccu gcgggccauc   1800
accagcaacg ucagugccau ccucgcccgc aacgggggca ucgggcuaug cgucgaggcg   1860
uuuaacgacu ccggccccgg gaccgccagc gucaugcccg cccucaaggu ccucgacucg   1920
cugguggcgg cgcacaacaa agagagcgcg cguccgaccg gcgcgugcgu uaccuggag   1980 ccguggcaca ccgacgugcg ggccgugcuc cggaugaagg ggguccucgc cggcgaagag   2040
gcccagcgcu gcgacaauau cuucagcgcc cucuggaugc cagaccuguu uucaagcgc    2100 cugauucgcc accuggacgg cgagaagaac gucacaugga cccguucga ccgggacacc     2160 agcaugucgc ucgccgacuu ucacggggag gaguucgaga agcucuacca gcaccucgag    2220 gucaugggu ucgcgagcca gauacccauc caggagcugg ccuauggcau ugugcgcagu    2280
gcggccacga cccgggagccc cuucgucaug uucaaagacg cggugaaccg ccacuacauc    2340
uacgacaccc aggggcggc caucgccggc uccaaccucu gcaccgagau cguccauccg    2400
gccuccaagc gauccagugg ggucugcaau cuggaagcug ugaaucuggc ccgaugcguc    2460
```

```
uccaggcaga cguuugacuu ugggcggcuc cgcgacgccg ugcaggcgug cgugcugaug    2520
gugaacauca ugaucgacag cacgcuacaa cccacgcccc agugcacccg cggcaacgac    2580
aaccugcggu ccaugggaau cggcaugcag ggccugcaca cggccugccu gaagcugggg    2640
cuggaucugg agucugccga auuucaggac cugaacaaac acaucgccga ggugaugcug    2700
cugucggcga ugaagaccag caacgcgcug ugcguucgcg gggcccgucc cuucaaccac    2760
uuuaagcgca gcauguaucg cgccggccgc uuucacuggg agcgcuuucc ggacgcccgg    2820
ccgcgguacg agggcgagug ggagaugcua cgccagagca ugaugaaaca cggccugcgc    2880
aacagccagu uugucgcgcu gaugcccacc gccgccucgg cgcagaucuc ggacgucagc    2940
gagggcuuug cccccugu caccaaccug uuuagcaagg ugacccggga cggcgagacg     3000
cugcgcccca acacgcuccu gcuaaaggaa cuggaacgca cguuuagcgg gaagcgccuc    3060
cuggagguga uggacaguuc gacgccaagc aguggaccgu ggcgcaggcg cucccgugcc    3120
uggagcccac ccaccccuc cggcgauuca agaccgcguu ugacuacgac cagaaguugc     3180
ugaucgaccu gugugcggac cgcgcccccu acgucgacca uagccaaucc augacccugu    3240
augucacgga gaaggcggac gggacccucc cagccuccac ccuggccgc cuucuggucc     3300 acgcauauaa gcgcgacua aaaacaggga uguacacug caagguucgc aaggcgacca     3360
acagcggggu cuuuggcggc gacgacaaca uugucugcac gagcugcgcg cuguagaacg    3420
ccauuaucac acuaaauauu uaaaaacgcc auuaucacac uaaaua                  3466
```

COMPOSITIONS AND PROCESSES FOR TARGETED DELIVERY, EXPRESSION AND MODULATION OF CODING RIBONUCLEIC ACIDS IN TISSUE

CROSS-REFERENCE TO RELATED APPLICATIONS

This application is a continuation application of U.S. application Ser. No. 16/811,504 filed Mar. 6, 2020, now pending; which is a continuation application of International Application No. PCT/US2018/049772 filed Sep. 6, 2018, now expired; which claims the benefit under 35 USC § 119(e) to U.S. application Ser. No. 62/632,056 filed Feb. 19, 2018; and the benefit under 35 USC § 119(a) to United Kingdom Patent Application No. GB 1714430.4 filed Sep. 7, 2017. The disclosure of each of the prior applications is considered part of and is incorporated by reference in the disclosure of this application.

INCORPORATION BY REFERENCE OF SEQUENCE LISTING

The material in the accompanying sequence listing is hereby incorporated by reference into this application. The accompanying sequence listing text file, named CTX1110-3_ST25. txt, was created on Mar. 23, 2022 and is 9 kB in size. The file can be accessed using Microsoft Word on a computer that uses Windows OS.

BACKGROUND OF THE INVENTION

Field of the Invention

The present invention relates to messenger ribonucleic acid (mRNA) delivery technologies, typically nanoparticle-based delivery, and methods of making and using these mRNA delivery technologies in a variety of therapeutic, diagnostic and prophylactic indications. Such delivery systems may be used as stand-alone interventions, or in combination with other therapeutic components.

Background Information

Gene therapy is the process of introducing coding polynucleotides into the cells of a patient in order to treat disease. For example, a mutated and/or functionless gene can be replaced in target cells by an intact copy. Gene therapy often relies on viral vectors to introduce coding polynucleotides into target cells, but other techniques exist to deliver polynucleotides to cells without the use of viruses. The advantages of viruses include relatively high possible transfection rates, as well as the ability to target the virus to particular cell types by control of the binding proteins by which viruses enter a target cell. In contrast, non-viral methods of introducing coding polynucleotides into cells can have problems with low transfection rates, as well as having limited options for targeting expression to particular organs and cell types. However, the nature of viral intervention carries risks of toxicity and inflammation, but also has limited control over the duration and degree of the expression of the introduced factor.

Tumour therapies based upon biological approaches have advantages over traditional chemotherapeutics because they can employ numerous diverse mechanisms to target and destroy cancers more precisely—e.g., via direct cell lysis, cytotoxic immune effector mechanisms and vascular collapse amongst others. As a result, there has been a significant increase in the number of clinical studies into the potential of such approaches. However due to the diverse range of therapeutic activities, pre-clinical and clinical study is complex, as multiple parameters may affect their therapeutic potential and, hence, defining reasons for treatment failure or methodologies that might enhance the therapeutic activity can be difficult. Maintaining on-target activities, tumour specificity and reducing side effects is also a major challenge for such experimental and powerful therapies.

In non-clinical contexts, too, the ability to induce expression of a particular gene product such as a polypeptide in a particular target tissue or organ is frequently desired. In many situations, a target tissue or organ, will comprise more than one type of cell, and in such cases it is also frequently desired to express the gene product to different degrees in the different cell types—that is, to provide differential expression in the different cell types. While methods exist to introduce polynucleotides in vitro and in vivo, they have the same limitations as discussed above.

There is therefore a need to further develop methods and compositions for delivery of polynucleotide sequences, such as mRNA, to specific organs and/or tissues, and methods to modulate the expression of the delivered polynucleotide sequences in specific cells.

SUMMARY OF THE INVENTION

The present invention accordingly provides compositions and methods which are capable of delivering expressible messenger RNA (mRNA) to cells in a target organ, and using the cellular system of microRNA-mediated expression modulation to drive differential expression in different cells, cell types and/or tissues within the target organ. Nanoscale delivery systems comprising the mRNA are used to enable delivery within the cells of a target organ. By supplying mRNA, the invention allows controllable and limited exogenous expression of polypeptide gene product from the supplied mRNA within different cell types, for example, cancerous, non-cancerous, diseased or healthy cells.

The invention can be used to enhance or modulate the function of various adjunct, co-administered or concurrently administered therapies. For example, the invention can be used in conjunction with oncolytic viral therapy, chemotherapy, antibody therapy or radiotherapy. In an example, mRNA coding for factors which increase the efficacy of an oncolytic virus administered to a patient can be selectively expressed in cancerous cells, thus increasing viral lysis of cancer cells while preserving non-cancerous and/or healthy cells. This approach can be used so that attenuated oncolytic viruses are restored to full potency in cancerous cells but not in neighbouring non-cancerous or healthy cells. A key advantage of this approach is that it reduces off target effects and increases the potency of the therapeutic effect, leading to reductions in dosage and associated side effects.

According to a first aspect of the invention, there is provided a composition for expressing a polypeptide within a target organ, the composition comprising a delivery particle, and at least a first mRNA sequence complexed with, encapsulated by, or otherwise associated with the delivery particle. The mRNA sequence comprises a coding sequence which codes for the polypeptide, at least a first untranslated region (UTR) sequence, and at least one micro-RNA (miRNA) binding site sequence, wherein the miRNA binding site sequence is located within, immediately 5' to, or immediately 3' to, the first UTR sequence. The miRNA binding site sequence is selected so as to provide for differential expression of the coding sequence between first and second cell types comprised within the target organ.

In an embodiment of the invention, the mRNA sequence may be encapsulated by the delivery particle. The delivery particles may comprise aminoalcohol lipidoids. In some embodiments the delivery particles are targeted towards the target organ, and may further comprise one or more targeting agents selected from: proteins, peptides, carbohydrates, glycoproteins, lipids, small molecules and nucleic acids, where these targeting agents associate preferentially with cells in the target organ.

In an embodiment of the invention, the miRNA binding site sequence comprises a plurality of miRNA binding site sequences. The plurality of miRNA binding site sequences may comprise greater than two, suitably greater than three, typically greater than four binding site sequences. The plurality of miRNA binding site sequences may each be substantially the same sequence, or may be one or more substantially different sequences. The plurality of miRNA binding site sequences may be different variants of sequences which are targets for the same miRNA species, or for different variants of the same miRNA species. In an embodiment of the invention, the miRNA binding site sequences may comprise one or more miRNA-122 binding site sequences, including variants and homologues thereof.

The different cell types in the target organ may comprise non-neoplastic cells, neoplastic (pre-cancerous or cancerous) cells, and combinations thereof. In particular, the first and second cell types may be different selections from the group comprising non-neoplastic cells, a transformed cell phenotype; a pre-cancerous phenotype; and a neoplastic phenotype. The non-neoplastic cells may be considered as healthy cells, or alternatively may include non-healthy (e.g., cirrhotic, inflamed, or infected) but otherwise non-cancerous cells.

According to an embodiment of the invention, the target organ comprises at least a first cell phenotype and at least a second cell phenotype; optionally the target organ comprises at least third, fourth, fifth, sixth, seventh and eighth cell phenotypes; suitably the target organ comprises a plurality of cell phenotypes. Where the invention relates to an embodiment comprising a plurality of cell phenotypes, differential expression occurs at detectable levels in at least one of the plurality of cell phenotypes but to a lesser extent or not detectably in the other cell phenotypes.

In embodiments of the invention the target organ comprises first and second cell types presenting different miRNA expression patterns. The target organ may be selected from liver, brain, lung, breast or pancreas. The target organ may be liver, in which embodiment both the particle and the mRNA are adapted to facilitate differential expression of the coding sequence within cell types or tissues comprised within the liver of a subject patient or animal.

The first UTR sequence may be located 3' to the coding sequence. In other embodiments the first UTR sequence may be located 5' to the coding sequence. In an embodiment of the invention the mRNA sequence further comprises a second UTR sequence, which has at least 90% similarity to a UTR sequence found in at least one of the different cell types within the target organ. Optionally second UTR sequence, has at least 90% similarity to a UTR sequence in at least one non-diseased cell type within the target organ. Optionally second UTR sequence, has at least 90% similarity to a UTR sequence in at least one diseased cell type within the target organ.

In some embodiments, the polypeptide comprises a therapeutic enhancement factor. The therapeutic enhancement factor may be selected from: a tumour suppressor protein, a programmed cell death protein, an inhibitor of a programmed cell death pathway, a monoclonal antibody or fragment or derivative thereof, a sequence-specific nuclease, an oncolytic viral virulence factor, a cytokine, a chemokine, a fluorescent marker protein and combinations thereof. In an embodiment the therapeutic enhancement factor is an immunomodulatory molecule selected from the group consisting of:

(i) cytokines involved in immune response and inflammation selected from one or more of: TNF α, TNFβ, IFNα, IFβ, IFNgamma, IL1, IL2, IL3, IL4, IL5, IL6, IL7, IL8, IL9, IL10, IL11, IL12, CCL 2, CCL3, CCL4, CCL5 CXCL 9, and CXCL10;

(ii) dendritic cell activators selected from one or more of: GM-CSF, TLR7 and TLR9;

(iii) molecules targeting the following cellular receptors and their ligands selected from one or more of: CD40, CD40L, CD160, 2B4, Tim-3, GP-2, B7H3 and B7H4;

(iv) TGF β inhibitors;

(v) T-cell membrane protein 3 inhibitors;

(vi) inhibitors of programmed death 1 (PD1), programmed death-ligand 1 (PDL1), programmed death-ligand 2 (PDL2), cytotoxic T-lymphocyte antigen 4 (CTLA4), and lymphocyte-activation gene 3 (LAG3); and (vii) NF-κB inhibitors.

In an embodiment the composition according to the invention may further comprise an oncolytic virus. Suitably the virus selected from any one of the Groups I-VII of the Baltimore classification of viruses. Optionally, the oncolytic virus is selected from the group comprising one or more of: Vesicular Stomatitis Virus, Maraba virus, Polio virus, Reovirus, Measles virus, Newcastle disease virus, Coxsackievirus A21, Parvovirus, Herpes Simplex Virus Type 1, and Adenovirus.

In another aspect of the invention, an isolated mRNA sequence for expressing a polypeptide within a target organ is provided. The sequence comprises at least one coding sequence which codes for the polypeptide, at least a first untranslated region (UTR) sequence, and at least one microRNA (miRNA) binding site sequence wherein the miRNA binding site sequence is located within, immediately 5' to or immediately 3' to, the first UTR sequence. The miRNA binding site sequence allows for differential expression of the coding sequence in different cell types within the target organ. Also envisaged in an embodiment of the invention is a polynucleotide expression construct encoding this mRNA sequence. It is intended that this aspect may further comprise any of the features discussed above in relation to the mRNA sequence of other embodiments of the invention. In another embodiment the polypeptide may code for a fluorescent marker protein, such as mCherry, as disclosed in SEQ ID NO:3.

In a further aspect of the invention, there is provided a method for the treatment, prevention, delay of the onset or progression, of cancer or alleviation of a symptom associated with cancer, the method comprising administering to a subject in need thereof a composition as discussed according to the above aspects and embodiments. The polypeptide, in certain embodiments, may code for a therapeutic enhancement factor, such as an immunomodulatory molecule or other factors as previously described.

In a further embodiment of the invention the the mRNA comprises a plurality of coding sequences, which may encode the same or different polypeptides.

In an aspect of the invention there is provided a polynucleotide expression vector construct encoding the mRNA sequence described. Suitably the polynucleotide expression vector comprises a DNA plasmid.

In embodiments of the invention the subject may be human or a non-human animal. The cancer may be selected from liver, brain, lung, breast or pancreatic cancer. The cancer may be liver cancer, which may suitably be hepatocarcinoma, or metastatic liver cancer. The liver cancer may be a primary cancer, such as hepatocarcinoma or hepatoblastoma, or secondary/metastatic cancer in the liver. The metastatic cancer may be from a known or unknown primary solid tumor. The methods may further comprise administering a therapy or therapeutic agent to the subject such as chemotherapy, an oncolytic virus, radiotherapy, a biological, an oncolytic virus, a small molecule drug, a adoptive cell therapy (such as CAR-T cell therapy, CAR-NK therapy), and combinations thereof.

In an aspect of the invention, the compositions and compounds as discussed according to the above aspects and embodiments are for use in medicine, suitably for the treatment of cancer. The cancer may be liver cancer, which may suitably be a primary cancer, such as a hepatocarcinoma; a hepatoblastoma; a cholangiocarcinoma; a angiosarcoma, or secondary/metastatic cancer in the liver.

In yet a further aspect of the invention, a process is provided for making a composition comprising a plurality of delivery particles as described herein, the process comprising:

(i) providing an encapsulating composition;
(ii) providing a solution comprising an mRNA sequence, wherein the mRNA sequence is for expressing a polypeptide within a target organ, the mRNA sequence comprising:
at least one coding sequence which codes for the polypeptide;
at least a first untranslated region (UTR) sequence;
at least one micro-RNA (miRNA) binding site sequence;
wherein the miRNA binding site sequence is located within, immediately 5' to or immediately 3' to, the first UTR sequence; and
wherein the miRNA binding site sequence allows for differential expression of the coding sequence in different cell types within the target organ;
(iii) combining the encapsulating composition with the solution comprising the mRNA sequence in order to form a complex between the encapsulating composition and the mRNA sequence; and
(iv) dispersing the complex of (iii) in order to create a plurality of delivery particles.

Suitably, the encapsulating composition is comprised of an aminoalcohol lipidoid, optionally an ethanolic solution comprising C12-200 aminoalcohol lipidoids. Typically the plurality of delivery particles comprises delivery particles having an average diameter of at least about 1 nanometres (nm), suitably at least about 30 nm, optionally at least about 50 nm and at most about 150 nm.

In yet a further aspect of the invention, there is provided a method for the treatment, prevention, delay of the onset or progression, of cancer or alleviation of a symptom associated with cancer, the method comprising providing a composition as discussed according to the above aspects and embodiments, and administering the composition in combination or concurrently with an oncolytic virus to a subject in need thereof.

In an embodiment, the mRNA sequence codes for a therapeutic agent which increases the efficacy of the oncolytic virus. The oncolytic virus may have been attenuated by deletion of one or more virulence genes, and the mRNA sequence may code for the one or more virulence genes, or an equivalent thereof.

In some embodiments, the oncolytic virus is selected from any one of the Groups I-VII of the Baltimore classification of viruses. The oncolytic virus may be selected from the group comprising one or more of: Vesicular Stomatitis Virus, Maraba virus, Polio virus, Reovirus, Measles virus, Newcastle disease virus, Coxsackievirus A21, Parvovirus, Herpes Simplex Virus Type 1, and Adenovirus. In an embodiment, the oncolytic virus is a Herpes Simplex Virus, and the mRNA sequence codes for US3, and may comprise SEQ ID NO: 4. In another embodiment, the oncolytic virus is a Herpes Simplex Virus, and the mRNA sequence codes for ICP6, and may comprise SEQ ID NO: 5.

BRIEF DESCRIPTION OF THE DRAWINGS

The invention is further illustrated by reference to the accompanying drawings in which:

FIG. 9A shows a method of preparation of a nanoformulation of delivery particles comprising mRNA according to an embodiment of the invention.

FIG. 9B shows the structure of a cross section of a delivery particle comprising mRNA according to an embodiment of the invention, and further comprising the encapsulating constituent compounds depicted in FIG. 8.

FIGS. 16A and 16B show the results of in vitro experiments where human cells from a model of hepatoblastoma (FIG. 16 A) and hepatocarcinoma (FIG. 16 B) were treated with virus alone or in combination with a composition according to an embodiment of the invention following the timetable of FIG. 15. The composition is a delivery particle comprising mRNA coding for US3 (US3 mRNA DMP$^{CTx}$). The effects of the treatments on cell viability are shown.

FIG. 17A shows the tumor growth (Hep3B cells are labelled with luciferase). FIG. 17B shows fluorescent microscopy images of the healthy mouse liver using mRNA coding for mCherry—no fluorence was detected when using the mCherry-DMP$^{CTx}$-miRNA122 composition.

DETAILED DESCRIPTION OF THE INVENTION

Figure 1:
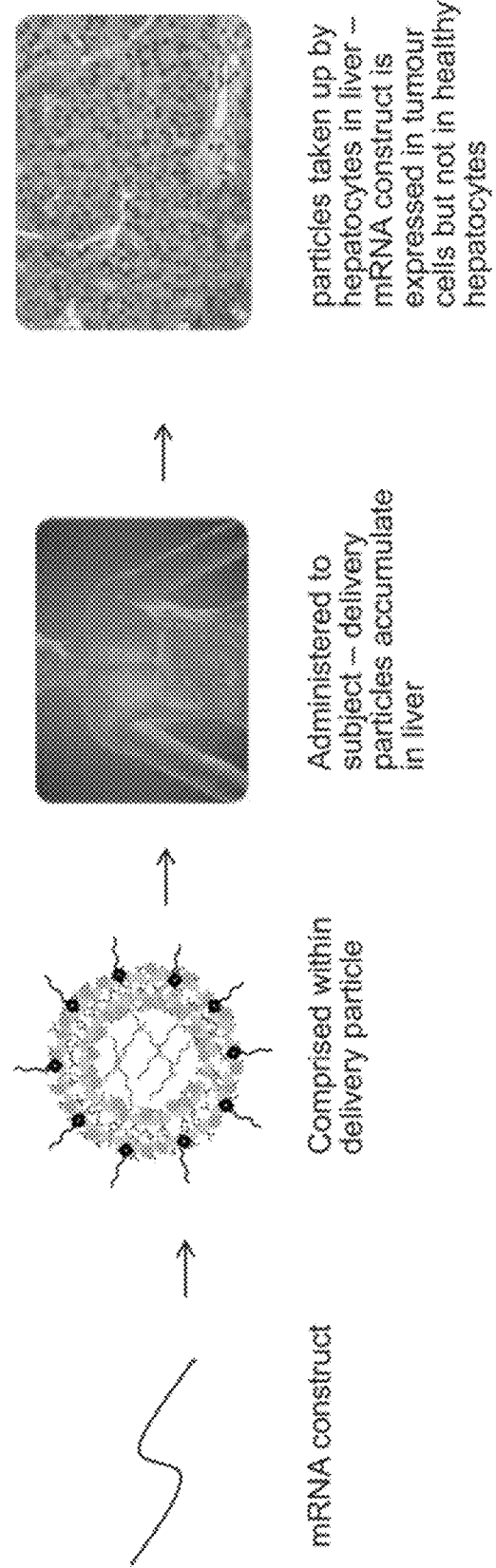
FIG. 1 shows a schematic of a method of administration of a lipidoid encapsulated mRNA composition according to one embodiment of the invention.

Unless otherwise indicated, the practice of the present invention employs conventional techniques of chemistry, molecular biology, microbiology, recombinant DNA technology, and chemical methods, which are within the capabilities of a person of ordinary skill in the art. Such techniques are also explained in the literature, for example, M. R. Green, J. Sambrook, 2012, Molecular Cloning: A Laboratory Manual, Fourth Edition, Books 1-3, Cold Spring Harbor Laboratory Press, Cold Spring Harbor, NY; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridisation: Principles and Practice, Oxford University Press; M. J. Gait (Editor), 1984, Oligonucleotide Synthesis: A Practical Approach, IRL Press; and D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference.

Prior to setting forth the invention, a number of definitions are provided that will assist in the understanding of the invention. All references cited herein are incorporated by reference in their entirety. Unless otherwise defined, all technical and scientific terms used herein have the same meaning as commonly understood by one of ordinary skill in the art to which this invention belongs.

As used herein, the term 'comprising' means any of the recited elements are necessarily included and other elements may optionally be included as well. 'Consisting essentially of' means any recited elements are necessarily included, elements that would materially affect the basic and novel characteristics of the listed elements are excluded, and other elements may optionally be included. 'Consisting of' means that all elements other than those listed are excluded. Embodiments defined by each of these terms are within the scope of this invention.

The term 'isolated', when applied to a polynucleotide sequence, denotes that the sequence has been removed from its natural organism of origin and is, thus, free of extraneous or unwanted coding or regulatory sequences. The isolated sequence is suitable for use in recombinant DNA processes and within genetically engineered protein synthesis systems. Such isolated sequences include cDNAs, mRNAs and genomic clones. The isolated sequences may be limited to a protein encoding sequence only, or can also include 5' and 3' regulatory sequences such as promoters and transcriptional terminators. Prior to further setting forth the invention, a number of definitions are provided that will assist in the understanding of the invention.

A 'polynucleotide' is a single or double stranded covalently-linked sequence of nucleotides in which the 3' and 5' ends on each nucleotide are joined by phosphodiester bonds. The polynucleotide may be made up of deoxyribonucleotide bases or ribonucleotide bases. Polynucleotides include DNA and RNA, and may be manufactured synthetically in vitro or isolated from natural sources. Sizes of polynucleotides are typically expressed as the number of base pairs (bp) for double stranded polynucleotides, or in the case of single stranded polynucleotides as the number of nucleotides (nt). One thousand bp or nt equal a kilobase (kb). Polynucleotides of less than around 40 nucleotides in length are typically called 'oligonucleotides'. The term 'nucleic acid sequence' as used herein, is a single or double stranded covalently-linked sequence of nucleotides in which the 3' and 5' ends on each nucleotide are joined by phosphodiester bonds. The polynucleotide may be made up of deoxyribonucleotide bases or ribonucleotide bases. Nucleic acid sequences may include DNA and RNA, and may be manufactured synthetically in vitro or isolated from natural sources. Sizes of nucleic acid sequences, also referred to herein as 'polynucleotides' are typically expressed as the number of base pairs (bp) for double stranded polynucleotides, or in the case of single stranded polynucleotides as the number of nucleotides (nt). One thousand bp or nt equal a kilobase (kb). Polynucleotides of less than around 40 nucleotides in length are typically called 'oligonucleotides' and may comprise primers for use in manipulation of DNA such as via polymerase chain reaction (PCR).

The term 'nucleic acid' as used herein, is a single or double stranded covalently-linked sequence of nucleotides in which the 3' and 5' ends on each nucleotide are joined by phosphodiester bonds. The polynucleotide may be made up of deoxyribonucleotide bases or ribonucleotide bases. Nucleic acids may include DNA and RNA, and may be manufactured synthetically in vitro or isolated from natural sources. Nucleic acids may further include modified DNA or RNA, for example DNA or RNA that has been methylated, or RNA that has been subject to post-translational modification, for example 5'-capping with 7-methylguanosine, 3'-processing such as cleavage and polyadenylation, and splicing. Nucleic acids may also include synthetic nucleic acids (XNA), such as hexitol nucleic acid (HNA), cyclohexene nucleic acid (CeNA), threose nucleic acid (TNA), glycerol nucleic acid (GNA), locked nucleic acid (LNA) and peptide nucleic acid (PNA). Sizes of nucleic acids, also referred to herein as 'polynucleotides' are typically expressed as the number of base pairs (bp) for double stranded polynucleotides, or in the case of single stranded polynucleotides as the number of nucleotides (nt). One thousand bp or nt equal a kilobase (kb). Polynucleotides of less than around 100 nucleotides in length are typically called 'oligonucleotides' and may comprise primers for use in manipulation of DNA such as via polymerase chain reaction (PCR). In specific embodiments of the present invention the nucleic acid sequence comprises messenger RNA (mRNA).

According to the present invention, homology to the nucleic acid sequences described herein is not limited simply to 100% sequence identity. Many nucleic acid sequences can demonstrate biochemical equivalence to each other despite having apparently low sequence identity. In the present invention homologous nucleic acid sequences are considered to be those that will hybridise to each other under conditions of low stringency (Sambrook J. et al, supra).

The term 'operatively linked', when applied to nucleic acid sequences, for example in an expression construct, indicates that the sequences are arranged so that they function cooperatively in order to achieve their intended purposes. By way of example, in a DNA vector a promoter sequence allows for initiation of transcription that proceeds through a linked coding sequence as far as a termination sequence. In the case of RNA sequences, one or more untranslated regions (UTRs) may be arranged in relation to a linked protein coding sequence referred to as an open reading frame (ORF). A given mRNA may comprise more than one ORFs, a so-called polycistronic RNA. A UTR may be located 5' or 3' in relation to an operatively linked coding sequence ORF. UTRs may comprise sequences typically found in mRNA sequences found in nature, such as Kozak consensus sequences, initiation codons, cis-acting regulatory elements, poly-A tails, internal ribosome entry sites (IRES), structures regulating mRNA longevity, sequences directing the localisation of the mRNA, and so on. A mRNA may comprise multiple UTRs that are the same or different.

The term 'expressing a polypeptide' in the context of the present invention refers to production of a polypeptide for which the polynucleotide sequences described herein code. Typically, this involves translation of the supplied mRNA sequence by the ribosomal machinery of the cell to which the sequence is delivered.

The term 'delivery particle' as used herein refers to particles which can comprise therapeutic components by encapsulation, holding within a matrix, the formation of complex or by other means, and deliver a therapeutic component such as a coding nucleic acid sequence into a target cell. Delivery particles may on the micro-scale, but in specific embodiments may typically be on the nanoscale—i.e., nanoparticles. Nanoparticles are typically sized at least 50 nm (nanometres), suitably at least approximately 100 nm and typically at most 150 nm, 200 nm, although optionally up to 300 nm in diameter. In one embodiment of the invention the nanoparticles have a mean diameter of approximately at least 60 nm. An advantage of these sizes is that this means that the particles are below the threshold for reticuloendothelial system (mononuclear phagocyte system) clearance, i.e., the particle is small enough not to be destroyed by phagocytic cells as part of the body's defence mechanism. This facilitates the use of intravenous delivery routes for the compositions of the invention.

Alternative possibilities for the composition of the nanoparticles include polylactic acid (PLA), poly(lactic-co-glycolic acid) (PLGA), a lipid- or phospholipid-based particles such as liposomes; particles based on proteins and/or glycoproteins such as collagen, albumin, gelatin, elastin, gliadin, keratin, legumin, zein, soy proteins, milk proteins such as casein, and others (Lohcharoenkal et al. BioMed Research International; Volume 2014 (2014)); and particles based on metals or metallic compounds such as gold, silver, aluminium, copper oxides and so on.

In particular, polymers comprising polyethyleneimine (PEI) have been investigated for the delivery of nucleic acids. Nanoparticle vectors composed of poly(β-amino esters) (PBAEs) have also been shown to be suitable for nucleic acid delivery, especially in coformulation with polyethylene glycol (PEG) (Kaczmarek J C et al Angew Chem Int Ed Engl. 2016; 55(44): 13808-13812). Particles of such coformulations have been used to deliver mRNA to the lung.

Also considered are particles based on polysaccharides and their derivatives, such as cellulose, chitin, and chitosan. Chitosan is a cationic linear polysaccharide obtained by partial deacetylation of chitin, with nanoparticles comprising this substance possessing promising properties for drug delivery such as biocompatibility, low toxicity and small size (Felt et al., Drug Development and Industrial Pharmacy, Volume 24, 1998—Issuer 11). It is envisioned that combinations between the above constituents may be used.

US2010/0331234, US2011/0293703 and US2015/0203439—which are incorporated herein by reference—describe the production of aminoalcohol lipidoids by reacting an amine with an epoxide-terminated compound. Complexes, micelles, liposomes and particles, including nanoparticles, may be prepared with these lipidoids and their chemical structure makes them particularly suited to the delivery of a 'cargo'—e.g., nucleic acids such as coding mRNAs—to target cell types within the body of a human or animal subject. Delivery platforms comprising aminoalcohol lipidoid compounds are particularly suitable for use in the delivery of net negatively charged cargo molecules given the tertiary amines available for protonation thus forming a cationic moiety. For example, aminoalcohol lipidoid compounds may be used in the preparation of particulate compositions to deliver DNA, RNA, or other polynucleotide cargoes to a subject or to a target cell or tissue. Suitable particles may be in the form of microparticles, nanoparticles, liposomes, or micelles.

The aminoalcohol lipidoid based delivery particles possess tertiary amines that are available to interact with a polynucleotide cargo, such as a coding mRNA. Polynucleotides, or derivatives thereof, are contacted with the aminoalcohol lipidoid compounds under conditions suitable to form polynucleotide/lipidoid complexes. The lipidoid is preferably at least partially protonated so as to form a complex with the negatively charged polynucleotide. In this way, the polynucleotide/lipidoid complexes form particles that are useful in the delivery of cargo polynucleotides to cells and tissues. In certain embodiments, multiple aminoalcohol lipidoid molecules may be associated with a polynucleotide molecule. The complex may include at least 1, at least 5, at least 10, at least 20, at least 50, or suitably at least 100 aminoalcohol lipidoid molecules. The complex may include at most 10,000, at most 5000, at most 2000, at most 1000, at most 500, or typically at most 100 aminoalcohol lipidoid molecules.

Those of ordinary skill in the art will appreciate that a population of particles follow principles of particle size distribution. Widely used, art-recognized methods of describing particle size distributions include, for example, average diameters and D values, such as the D50 value, which is commonly used to represent the mean diameter of the range of the particle sizes of a given sample. In certain embodiments, the diameter of the nanoparticles particles ranges from 10-500 nm, more suitably the diameter of the particles ranges from 10-1200 nm, and particularly from 50-150 nm. In some embodiments, the nanoparticles have average diameters of at least about 10 nm, suitably at least about 30 nm. In some embodiments, nanoparticles have average diameters of less than about 150 nm in average diameter and greater than 50 nm in average.

The particles may be further associated with a targeting agent at facilitates binding of the delivery particle to a target cell type. The term 'targeted' as used herein in relation to refers to an object, or composition such as comprising a delivery particle, which is intended to associate with and facilitate transfection of cells within a particular organ, tissue or cell type within the body. In a particular embodiment, a delivery particle—such as a delivery nanoparticle—may be targeted to deliver its cargo only to a certain organ, tissue or cell type. Targeting may be geographical, for example by the delivery of the targeted object directly to a particular tissue, or may be mediated chemically, through targeting agents or binding moieties which preferentially associate with target cells or tissues.

A variety of targeting agents that direct pharmaceutical compositions to particular cells are known in the art (see, for example, Cotten et al. Methods Enzym. 217:618, 1993; Wagner et al. Advanced Drug Delivery Reviews, Volume 14, Issue 1, April-May 1994, 113-135; Fiume et al. Advanced Drug Delivery Reviews, Volume 14, Issue 1, April-May 1994, 51-65). The targeting agents may be included throughout the particle or may be localised only on the surface. The targeting agent may be a protein, peptide, carbohydrate, glycoprotein, lipid, small molecule, nucleic acids, etc. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferrin, asialoglycoproteins, gp120 envelope protein of the human immunodeficiency virus (HIV), carbohydrates, receptor ligands, sialic acid, aptamers etc. If the targeting agent is distributed throughout the particle, the targeting agent may be included in the mixture or composite that is used to form the particles. If the targeting agent is only located on the surface, the targeting agent may be associated with the formed particles using standard chemical techniques e.g., by covalent binding, hydrophobic, hydrogen bonding, van der Waals, biotin-avidin linkage, or other interactions.

The particulate compositions of certain embodiments of the invention may suitably deliver the encapsulated mRNA cargo over a period of time that may be controlled by the particular choice or formulation of the encapsulating biodegradable non-toxic polymer or biocompatible material. For example, the particulate compositions may release the encapsulated mRNA cargo over at least 30 minutes, at least 1 hour, at least 2 hours, at least 6 hours, at least 12 hours, or at least 1 day. The particulate compositions may release the encapsulated mRNA cargo over at most 2 days, at most 3 days, or at most 7 days.

The term 'diseased' as used herein, as in 'diseased cells' and/or 'diseased tissue' indicates tissues and organs (or parts thereof) and cells which exhibit an aberrant, non-healthy or disease pathology. For instance, diseased cells may be infected with a virus, bacterium, prion or eukaryotic parasite; may comprise deleterious mutations; and/or may be cancerous, precancerous, tumoural or neoplastic. Diseased cells may comprise an altered intra-cellular miRNA environment when compared to otherwise normal or so-called healthy cells. In certain instances disease cells may be pathologically normal but comprise an altered intra-cellular miRNA environment that represents a precursor state to disease. Diseased tissues may comprise healthy tissues that have been infiltrated by diseased cells from another organ or organ system. By way of example, many inflammatory diseases comprise pathologies where otherwise healthy organs are subjected to infiltration with immune cells such as T cells and neutrophils. By way of a further example, organs and tissues subjected to stenotic or cirrhotic lesions may comprise both healthy and diseased cells in close proximity.

The term 'cancer' as used herein refers to neoplasms in tissue, including malignant tumours which may be primary cancer starting in a particular tissue, or secondary cancer having spread by metastasis from elsewhere. The terms cancer, neoplasm and malignant tumours are used interchangeably herein. Cancer may denote a tissue or a cell located within a neoplasm or with properties associated with a neoplasm. Neoplasms typically possess characteristics that differentiate them from normal tissue and normal cells. Among such characteristics are included, but not limited to: a degree of anaplasia, changes in morphology, irregularity of shape, reduced cell adhesiveness, the ability to metastasize, and increased cell proliferation. Terms pertaining to and often synonymous with 'cancer' include sarcoma, carcinoma, malignant tumour, epithelioma, leukaemia, lymphoma, transformation, neoplasm and the like. As used herein, the term 'cancer' includes premalignant, and/or precancerous tumours, as well as malignant cancers.

The term 'healthy' as used herein, as in 'healthy cells' and/or 'healthy tissue' indicates tissues and organs (or parts thereof) and cells which are not themselves diseased and approximate to a typically normal functioning phenotype. It can be appreciated that in the context of the invention the term 'healthy' is relative, as, for example, non-neoplastic cells in a tissue affected by tumours may well not be entirely healthy in an absolute sense. Therefore 'non-healthy cells' is used mean cells which are not themselves neoplastic, cancerous or pre-cancerous but which may be cirrhotic, inflamed, or infected, or otherwise diseased for example. Similarly, 'healthy or non-healthy tissue' is used to mean tissue, or parts thereof, without tumours, neoplastic, cancerous or pre-cancerous cells; or other diseases as mentioned above; regardless of overall health. For instance, in the context of an organ comprising cancerous and fibrotic tissue, cells comprised within the fibrotic tissue may be thought of as relatively 'healthy' compared to the cancerous tissue.

In an alternative embodiment, the health status of a cell, cell type, tissue and/or organ is determined by the quantification of miRNA expression. In certain disease types, such as cancer, the expression of particular miRNA species is affected, and can be up- or down-regulated compared to unaffected cells. This difference in the miRNA transcriptome can be used to identify relative states of health, and/or to track the progression of healthy cells, cell types, tissues and/or organs towards a disease state. The disease state may include the various stages of transformation into a neoplastic cell. In embodiments of the present invention the differential variations in the miRNA transcriptome of cell types comprised within a given organ or organ system is leveraged in order to control protein expression in the different cell types.

As used herein, the term 'organ' is synonymous with an 'organ system' and refers to a combination of tissues and/or cell types that may be compartmentalised within the body of a subject to provide a biological function, such as a physiological, anatomical, homeostatic or endocrine function. Suitably, organs or organ systems may mean a vascularized internal organ, such as a liver or pancreas. Typically organs comprise at least two tissue types, and/or a plurality of cell types that exhibit a phenotype characteristic of the organ.

The term 'therapeutic virus' as used herein refers to a virus which is capable of infecting and killing cancer cells, sometimes by direct viral lysis (oncolysis), but also including indirect killing by the stimulation of host anti-tumoural responses. Oncolytic viruses are frequently characterised by having increased activity in diseased cells, including cancer cells, compared with healthy cells.

Examples of oncolytic viruses include those provided in Table 1, and subtypes thereof.

TABLE 1

| Oncolytic Virus | Type |
| --- | --- |
| Vesicular Somatitis Virus | Enveloped RNA |
| Maraba virus | Enveloped rhabdovirus |
| Polio virus | Non enveloped RNA |
| Reovirus | Non enveloped RNA |
| Measles virus | Enveloped RNA |
| Newcastle disease virus | Enveloped RNA |
| Coxsackievirus A21 | Non enveloped RNA |
| Parvovirus | Non enveloped DNA |
| Herpes Simplex Virus Type 1 | Enveloped DNA |
| Adenovirus | Non enveloped DNA |

In embodiments of the invention viruses may be selected from any one of the Groups I-VII of the Baltimore classification of viruses (Baltimore D (1971). "Expression of animal virus genomes". Bacteriol Rev. 35 (3): 235-41). In specific embodiments of the invention suitable viruses may be selected from Baltimore Group I, which are characterised as having double stranded DNA viral genomes; Group IV, which have single stranded positive RNA genomes; and Group V, which have single stranded negative RNA genomes.

The term 'virulence gene' or 'virulence factor' as used herein refers to a gene or gene product which aids in the replication of a therapeutic virus such as an oncolytic virus within or lysis of the cells which it infects. The term 'replication factor' is used as a synonymous term herein. Virulence factors may typically be viral genes encoded by the viral genome. Virulence factors may be involved in functions such as intracellular immune system suppression and evasion, viral genome replication, the spread or transmission of virions, the production or assembly of structural coat proteins, the activation of viruses in a latent state, the prevention of viral latency, and the takeover of host cell processes. Several virulence factors have cellular or other equivalents which can compensate for the function of these genes if lacking in the virus genome. Some viruses can be modified with exogenous virulence genes which increase their ability to replicate, lyse cells, and spread.

In specific embodiments of the present invention the compositions enhance or sustain the oncolytic potency of a virus in a tumor located within an organ through differential expression of protein or polypeptide that enhances virion replication preferentially in the tumor. In further embodiments of the invention the compositions may encode a gene product that controls the interaction between host immune cells and oncolytic virus within a tumour. In yet a further embodiment, the compositions of the invention can be used to produce gene products that modulate differential patterns of oncolytic virus activity as well as expression of immune co-stimulatory molecules that are administered via the virion, exogenously or via a delivery particle of the invention.

The term 'polypeptide' as used herein is a polymer of amino acid residues joined by peptide bonds, whether produced naturally or in vitro by synthetic means. Polypeptides of less than around 12 amino acid residues in length are typically referred to as "peptides" and those between about 12 and about 30 amino acid residues in length may be referred to as "oligopeptides". The term "polypeptide" as used herein denotes the product of a naturally occurring polypeptide, precursor form or proprotein. Polypeptides can also undergo maturation or post-translational modification processes that may include, but are not limited to: glycosylation, proteolytic cleavage, lipidization, signal peptide cleavage, propeptide cleavage, phosphorylation, and such like. The term "protein" is used herein to refer to a macromolecule comprising one or more polypeptide chains.

The term 'gene product' as used herein refers to the product of the coding sequence or ORF comprised within an mRNA construct as described herein. The gene product may comprise a polypeptide or a protein. A polycistronic mRNA construct may result in the production of multiple gene products.

Delivery of mRNA directly to cells allows direct and controllable translation of the desired gene products such as polypeptides and/or proteins in the cells. Provision of mRNA specifically allows not only for the use of cell expression modulation mechanisms such as miRNA mediated control (as detailed in specific embodiments below), but also represents a finite and exhaustible supply of the product, rather than the potentially permanent change to the transcriptome of a target cell which an episomal or genomically inserted DNA vector might provide.

In embodiments of the present invention an mRNA sequence is provided that comprises a sequence that codes for at least one polypeptide in operative combination with one or more untranslated regions (UTRs) that may confer tissue specificity, and stability to the nucleic acid sequence as a whole. By 'tissue specificity' it is meant that translation of the protein product encoded by the mRNA is modulated according to the presence of the UTR. Modulation may include permitting, reducing or even blocking detectable translation of the mRNA into a protein product. The UTRs may be linked directly to the mRNA in cis—i.e., on the same polynucleotide strand. In an alternative embodiment, a first sequence that codes for a gene product is provided and a further second sequence, that hybridises to a portion of the first sequence, is provided that comprises one or more UTRs that confer tissue specificity to the nucleic acid sequence as a whole. In this latter embodiment the UTR is operatively linked to the sequence that encodes the gene product in trans.

According to specific embodiments of the invention, an mRNA is provided that comprises such associated nucleic acid sequences operatively linked thereto as are necessary to prevent or reduce expression of a gene product in non-diseased liver tissue, e.g., in healthy hepatocytes. As such, an mRNA construct, or transcript, is provided that comprises a 5' cap and UTRs necessary for ribosomal recruitment and tissue specific expression (typically, but not exclusively positioned 3' to the ORF), as well as start and stop codons that respectively define the ORF. When the construct is introduced into a non-diseased liver, expression of the gene product is prevented or reduced. In contrast, neoplastic cells comprised within the liver typically do not conform to normal non-diseased liver cell expression patterns, posessing a quite different miRNA transcriptome. The gene product is translated specifically in these cancer cells but not in neighboring healthy hepatocytes. Delivery of the mRNA construct to the liver tissue may be achieved via a particulate delivery platform as described herein. Cell type specific expression can be mediated via microRNA modulation mechanisms such as those described in more detail below.

A 'therapeutic component' or 'therapeutic agent' as defined herein refers to a molecule, substance, cell or organism that when administered to an individual human or other animal as part of a therapeutic intervention, contributes towards a therapeutic effect upon that individual human or other animal. The therapeutic effect may be caused by the therapeutic component itself, or by another component of the therapeutic intervention. The therapeutic component may be a coding nucleic acid component, in particular an mRNA. The coding nucleic acid component may code for a therapeutic enhancement factor, as defined below. A therapeutic component may also comprise a drug, optionally a chemotherapeutic drug such as a small molecule or monoclonal antibody (or fragment thereof). In some embodiments, a therapeutic component may comprise a cell, such as a recombinantly modified immune effector cell—e.g., a CAR-T cell. In other embodiments of the invention, the therapeutic agent comprises a therapeutic virus, such as an oncolytic virus or a viral vector.

The term 'therapeutic effect' refers to a local or systemic effect in an animal subject, typically a human, caused by a pharmacologically or therapeutically active agent that comprises a substance, molecule, composition, cell or organism that has been administered to the subject, and the term 'therapeutic intervention' refers to the administration of such a substance, molecule, composition, cell or organism. The term thus means any agent intended for use in the diagnosis, cure, mitigation, treatment or prevention of disease or in the enhancement of desirable physical or mental development and conditions in an animal or human subject. The phrase 'therapeutically-effective amount' means that amount of such an agent that produces a desired local or systemic effect at a reasonable benefit/risk ratio applicable to any treatment. In certain embodiments, a therapeutically effective amount of an agent will depend on its therapeutic index, solubility, and the like. For example, certain therapeutic agents of the present invention may be administered in a sufficient amount to produce a reasonable benefit/risk ratio applicable to such treatment. In the specific context of treatment of cancer, a 'therapeutic effect' can be manifested by various means, including but not limited to, a decrease in solid tumour volume, a decrease in the number of cancer cells, a decrease in the number of metastases observed, an increase in life expectancy, decrease in cancer cell proliferation, decrease in cancer cell survival, a decrease in the expression of tumour cell markers, and/or amelioration of various physiological symptoms associated with the cancerous condition.

In one embodiment, the subject to whom therapy is administered is a mammal (e.g., mouse, rat, primate, non-human mammal, domestic animal or livestock, such as a dog, cat, cow, horse, sheep, goat and the like), and is suitably a human. In a further embodiment, the subject is an animal model of cancer. For example, the animal model can be an orthotopic xenograft animal model of a human-derived cancer, suitably liver cancer.

In a specific embodiment of the methods of the present invention, the subject has not yet undergone a therapeutic treatment, such as therapeutic viral therapy, chemotherapy, radiation therapy, targeted therapy, and/or anti-immune checkpoint therapy. In still another embodiment, the subject has undergone a therapeutic treatment, such as the aforementioned therapies.

In further embodiments, the subject has had surgery to remove cancerous or precancerous tissue. In other embodiments, the cancerous tissue has not been removed, for example, the cancerous tissue may be located in an inoperable region of the body, such as in a tissue that if subjected to surgical intervention may compromise the life of the subject, or in a region where a surgical procedure would cause considerable risk of permanent harm.

In some embodiments, the provided mRNA may code for a 'therapeutic enhancement factor'. According to the present invention therapeutic enhancement factors are gene products or polypeptides that may enhance or facilitate the ability of another, co-administered therapeutic agent, to exert a therapeutic effect upon a given cell, suitably the target cell. When introduced into or in the vicinity of the target cell, expression of the therapeutic enhancement factor may cooperate with a co-administered therapeutic agent thereby enabling or enhancing the therapeutic activity of the agent. In some embodiments, the therapeutic enhancement factor may enhance the ability of a co-administered oncolytic virus to lyse cancer cells. In other embodiments of the invention, the therapeutic enhancement factor may effect an alteration of a tumour microenvironment so as to assist or recruit the subject's own immune response. In this latter embodiment, the alteration of the tumour microenvironment may assist co-administration of an oncolytic virus or a CAR-T or other adoptive cell based therapy. In some embodiments, the therapeutic enhancement factor may enable the conversion of a prodrug into an active form.

Multiple therapeutic enhancement factors may be combined in compositions according to specific embodiments of the present invention. In such embodiments, the coding sequences for each therapeutic enhancement factor may be present in separate mRNA molecules. In some embodiments, sequences for more than one therapeutic enhancement factor may be present on the same mRNA molecule. In such cases the polycistronic mRNA molecule further comprises sequences as necessary for the expression of all coded sequences, such as internal ribosome entry sites (IRES).

In embodiments where multiple different mRNA molecules are comprised in one or more delivery particles, it is contemplated that each delivery particle may comprise one or more than one type of mRNA molecule; that is, not every delivery particle in a particular embodiment will necessarily comprise all of the mRNA molecules provided in said embodiment.

The mRNA constructs of certain embodiments of the invention may be synthesised from a polynucleotide expression construct, which may be for example a DNA plasmid. This expression construct may comprise any promoter sequence necessary for the initiation of transcription and a corresponding termination sequence, such that transcription of the mRNA construct can occur. Such polynucleotide expression constructs are contemplated to comprise embodiments of the invention in their own right.

The gene product encoded by the mRNA is typically a peptide, polypeptide or protein. Where a particular protein consists of more than one subunit, the mRNA may code for one or more than one subunit.

The gene product encoded by the mRNA may be of any type suitable for producing a therapeutic effect. In the context of treating cancer, the gene product encoded by the mRNA may suitably include genes which when expressed by a cancer cell cause or aid in the destruction of the cancer cell.

Tumour suppressor genes such as p53 may be provided by the constructs of the invention. p53 plays a role in cell processes including apoptosis and genomic stability. It is involved in the activation of the DNA repair process in response to genomic damage, and can arrest cell growth and reproduction.

Genes which promote cell death by apoptosis—so-called suicide genes—which when expressed cause the cell to activate the process of apoptosis, may also be provided by the compositions and constructs of the invention. Cancer cells often possess mutated and/or functionless versions of these apoptosis-related genes, and so cannot undergo apoptosis in response to external signals. Suicide gene therapy may also refer to the introduction of genes which allow the conversion of a non-toxic compound or prodrug into a lethal drug (Duarte et al. Cancer Letters, 2012). According to embodiments of the invention, such gene products can be introduced selectively into diseased cells, such as neoplastic cells, marking them for destruction by induced apoptosis or delivery of an otherwise non-toxic compound or prodrug.

In specific embodiments of the invention, the mRNA may encode inhibitors of the programmed cell death pathway, such as inhibitors of PD-1 receptor (CD279) or its ligands PD-L1 (B7-H1; CD274) and PD-L2 (B7-DC; CD273). Hence, the mRNA may encode a protein or polypeptide that binds to or otherwise interferes with the function of the PD-1/PDL-1 or PD-1/PDL-2 axis within diseased or neoplastic cells within a target organ. Suitable proteins or polypeptides may include antibodies, which may be monoclonal or polyclonal, or antigen binding fragments thereof, or other antigen binding microproteins, that bind to PD-1 receptor, PDL-1, PDL-2, or complexes of ligand and receptor. This effect may also be observed by use of protein or polypeptide inhibitors of the cytotoxic T lymphocyte antigen 4 (CTLA4) pathway, another so-called immune checkpoint. Inhibition of either or both pathways is known to result in a change in the immune response within the tumour microenvironment that may positively benefit the health of the patient. In addition, by modulating the immune response in a subject the compositions of the present invention may show particular utility in combinatorial therapies with other anti-cancer therapeutic approaches, such as radiotherapy or chemotherapy. FDA approved anti-PD1 pathway inhibitors include pembrolizumab and nivolumab. Known anti-PDL-1 inhibitors include MPDL-3280A, BMS-936559 and atezolizumab. Anti-CTLA4 therapeutic inhibitors include ipilimumab and tremelimumab. The compositions of the invention may be used to deliver such inhibitors of the programmed cell death pathway selectively to diseased cells within a target organ in a subject by leveraging the differential miRNA environment in those cells.

Chimeric antigen receptor T-cells (CAR-T cells) are immune cells, typically T-lymphocytes, which have been modified to express receptors which target cancer cells.

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (see e.g., Park, T. S., S. A. Rosenberg, et al. (2011). "Treating cancer with genetically engineered T cells." Trends Biotechnol 29(11): 550-7).

Novel specificities in T cells, also known as immune effector cells, have been successfully generated through the genetic transfer of transgenic T cell receptors or chimeric antigen receptors (CARs) (see e.g., Jena, B., G. Dotti, et al. (2010). "Redirecting T-cell specificity by introducing a tumor-specific chimeric antigen receptor." Blood 116(7): 1035-44). CARs are synthetic receptors consisting of at least three parts: an extracellular antigen recognition domain (also known as the ectodomain), a transmembrane domain, and an intracellular T-cell activation domain (also known as the endodomain). In some embodiments, the engineered T cells comprise a specific class of T cells, such as, for example, gamma delta T cells, a subtype of T cells that selectively target tumoral cells without affecting healthy ones. CARs have successfully allowed T cells to be redirected against antigens expressed at the surface of tumor cells from various malignancies including lymphomas and solid tumors (Jena, Dotti et al. supra). In some embodiments, the engineered T cells comprise at least a population of autologous T cells in which the CAR-T cells are engineered to eliminate expression of the endogenous αβ T-cell receptor (TCR) to prevent a graft-versus-host response without compromising CAR-dependent effector functions. In some embodiments, the engineered T cells comprise at least a population of allogeneic T cells. In some embodiments, the engineered T cells comprise at least a population of autologous T cells and a population of allogeneic T cells.

Generally, the extracellular antigen recognition domain is a targeting moiety that is associated with one or more signaling domains in a single fusion molecule from an antibody, receptor, or ligand domain that binds a specific target, typically a tumor-associated target. In some embodiments, the extracellular antigen recognition domain is or is derived from a single-chain Fragment variant (scFv) of an antigen-binding domain of a single-chain antibody (scFv), comprising the light and heavy variable fragments of a monoclonal antibody joined by a flexible linker. In some embodiments, In some embodiments, extracellular antigen recognition domain is linked to the transmembrane domain by a linker, such as, for example, a flexible linker such as the IgG1 hinge linker. In some embodiments, the transmembrane is or is derived from a CD28 transmembrane domain. In some embodiments, the endodomain includes a co-stimulatory domain designed to enhance the immune response, for example, by enhancing survival and increasing proliferation of CAR modified T cells, and an internal T-cell activation domain designed to activate the T cell when it binds to the desired target. In some embodiments, the costimulatory domain is or is derived from a CD28 costimulatory domain, an OX-40 (CD134) costimulatory domain, an ICOS costimulatory domain, a 4-1BB (CD137) costimulatory domain, or any combination thereof. In some embodiments, the intracellular T-cell activation domain comprises the CD3 zeta (CD3ζ) domain or a biologically active portion thereof. In some embodiments, T cell activation results in immune cell activation in which inflammatory cytokines are released by the T cells to promote an inflammation and/or immune response. In some embodiments, T cell activation results in cytotoxic activity in which cytotoxins are released by the T cells to promote cancer cell apoptosis. In some embodiments, T cell activation results in proliferation in which interleukins are released by the T cells to promote cell development and division. In some embodiments, T cell activation results in a combination of at least two of immune cell activation, cytotoxic activity, and/or proliferation.

In some embodiments, the extracellular antigen recognition domain specifically binds to CD19. CD19 is an attractive target for immunotherapy because the vast majority of B-acute lymphoblastic leukemia (B-ALL) uniformly express CD19, whereas expression is absent on non-hematopoietic cells, as well as myeloid, erythroid, and T cells, and bone marrow stem cells. Clinical trials targeting CD19 on B-cell malignancies are underway with encouraging antitumor responses. Many of the current CAR-T therapies being evaluated in clinical trials use T cells genetically modified to express a chimeric antigen receptor (CAR) with specificity derived from the scFv region of a CD19-specific mouse monoclonal antibody FMC63 (see e.g., Nicholson, Lenton et al. (1997); "Construction and characterisation of a functional CD19 specific single chain Fv fragment for immunotherapy of B lineage leukaemia and lymphoma." Mol Immunol. 1997 November-December; 34 (16-17): 1157-65; Cooper, Topp et al. (2003). "T-cell clones can be rendered specific for CD19: toward the selective augmentation of the graft-versus-B-lineage leukemia effect." Blood. 2003 Feb. 15; 101(4):1637-44; Cooper, Jena et al. (2012) (International application: WO2013/126712)).

In some embodiments, extracellular antigen recognition domain specifically binds to CD22. CD22 is a transmembrane phosphoglycoprotein that belongs to the Siglec family of lectins and specifically binds sialic acid with its N-terminus seven extracellular immunoglobulin domains. It mainly acts as an inhibitory receptor for B cell activation and signaling and regulates the interaction of B cells with T cells and antigen presenting cells (APCs). Similar to CD19, CD22 is a B cell lineage-restricted marker, expressed explicitly by B lymphoid cells from the pre-B to mature B cell stage. However, it is lost during differentiation to plasma cells. CD22 is universally expressed in most B cell malignancies, including acute lymphoblastic leukemia (ALL), chronic lymphocytic leukemia (CLL), and various subtypes of non-Hodgkin lymphoma (NHL) such as diffuse large B cell lymphoma. Targeting CD22 as an attractive therapeutic target for B cell malignancies has been confirmed by positive results in clinical trials of anti-CD22 monoclonal antibodies (e.g., epratuzumab) and immunotoxins (e.g., BL22, HA22). CD22 has been shown to be expressed on ALL cells that lost CD19 expression after treatment with anti-CD19 CAR-T cells, making anti-CD22 CAR-T cells suitable for combination and/or follow-on therapy of anti-CD19 CAR-T cells.

However, although numerous clinical studies have demonstrated the potential of adoptive transfer of CAR T cells for cancer therapy, they have also raised the risks associated with the cytokine-release syndrome (CRS) and the "on-target off-tumour" effect.

The mRNA nanoparticle delivery compositions provided herein are useful to improve the safety and efficacy of CAR-T-cells. For example, the mRNA nanoparticle delivery systems of embodiments described herein may be used to recruit specific immune cells or modified subsets of immune cells such as CAR-T cells to the tumour microenvironment. Additionally, the mRNA nanoparticle delivery systems may be used to inhibit expression of endogenous T cell receptors (TCRs) to avoid graft-versus-host disease and/or to selectively delete immune checkpoint genes in these cells to strengthen their anti-cancer activity in the suppressive tumour milieu. (See e.g., Moffett, Coon, et al. (2017) "Hit-and-run programming of therapeutic cytoreagents using mRNA nanocarriers." Nature Communications. 8:389.)

In some embodiments, the coding mRNA and the delivery particles are used to attract CAR-T cells to a particular site in a subject. In some embodiments, the coding mRNA and the delivery particles are used to overcome insufficient migration of an immune cell to the tumour microenvironment. In response to specific chemokines, different immune cell subsets migrate into the tumour microenvironment and regulate tumour immune responses in a spatiotemporal manner. In addition, chemokines can directly target non-immune cells, including tumour cells and vascular endothelial cells, in the tumour microenvironment, and they have been shown to regulate tumour cell proliferation, cancer stem-like cell properties, cancer invasiveness and metastasis. In some embodiments, the immune cell is a T cell, a natural killer (NK) cell, a B cell, an antigen-presenting cell (APC) such as a macrophage or dendritic cell, or any combination thereof.

In some embodiments, the coding mRNA and the delivery particles are used to overcome insufficient migration of CAR T cells to the tumour microenvironment. In some embodiments, the delivery particles specifically target the tumour microenvironment, and the coding mRNA encodes a gene product that attracts or otherwise recruits CAR-T cells to the tumour microenvironment. In some embodiments, the coding mRNA expresses a chemokine. By way of non-limiting example, the coding mRNA can encode a chemokine that attracts T-cells such as CCL2, CCL3, CCL4, CCL5, CCL20, CCL22, CCL28, CXCL8, CXCL9, CXCL10, CXCL11, CXCL12, XCL1, and any combination thereof. In situations where the reverse effect is desired, such as in autoimmune disease, the coding mRNA can express blockers, antagonists and/or inhibitors of the above-mentioned factors.

In some embodiments, the coding mRNA and delivery particles are used to transiently express the coding mRNA in the tumour microenvironment. In some embodiments, the coding mRNA encodes a cytokine or other gene product involved in regulating the survival, proliferation, and/or differentiation of immune cells in the tumour response, such as, for example, activated T cells and NK cells. By way of non-limiting example, the coding mRNA can encode for a cytokine such as IL-1, IL-2, IL-4, IL-6, IL-8, IL-10, IL-12, IL-17, IL-33, IL-35, TGF-beta, and any combination thereof. Again, in situations where the reverse effect is desired, such as in autoimmune disease, the coding mRNA can express blockers, antagonists and/or inhibitors of the above-mentioned factors.

In some embodiments, of the invention, the coding mRNA and the delivery particle are used in conjunction with CAR-T or other adoptive cell therapy to provide transient expression of the coding mRNA.

In some embodiments, the mRNA nanoparticle delivery system delivers an mRNA that codes for a gene-editing agent to a target cell population. In some embodiments, the mRNA codes for a sequence-specific nuclease that targets a gene locus and disrupts expression of one or more endogenous gene produces in the target cell population. In some embodiments, the mRNA codes for a sequence-specific nuclease that targets a T cell receptor (TCR)-related gene locus, thereby disrupting expression of one or more domains in the TCR.

In some embodiments, the mRNA nanoparticle delivery compositions may be used to deliver an mRNA that codes for one or more agents that program engineered T cells toward a desired phenotype. In some embodiments, the mRNA nanoparticle delivery compositions may be used to induce markers and transcriptional patterns that are characteristic of a desired T cell phenotype. In some embodiments, the mRNA nanoparticle delivery compositions may be used to promote development of CD26L+ central memory T cells (Tcm), which have been shown to improve CAR-T treatment. (See e.g., Moffett, Coon supra).

In some embodiments, the mRNA nanoparticle delivery compositions include a surface-anchored targeting domain that is specific for a T cell marker, such as, for example, a surface antigen found on T cells. In some embodiments, the surface-anchored targeting domain is specific for an antigen that selectively binds the nanoparticle to T-cells and initiates receptor-induced endocytosis to internalize the mRNA nanoparticle delivery compositions. In some embodiments, the surface-anchored targeting domain selectively binds CD3, CD8, or a combination thereof. In some embodiments, surface-anchored targeting domain is or is derived from an antibody that selectively binds CD3, CD8, or a combination thereof.

MicroRNAs (miRNAs) are a class of noncoding RNAs each containing around 20 to 25 nucleotides some of which are believed to be involved in post-transcriptional regulation of gene expression by binding to complementary sequences in the 3' untranslated regions (3' UTR) of target mRNAs, leading to their silencing. These sequences are also referred to herein as miRNA binding site, or miRNA binding site sequences. Certain miRNAs are highly tissue-specific in their expression; for example, miR-122 and its variants are abundant in the liver and infrequently expressed in other tissues (Lagos-Quintana (2002), Current Biology, Vol. 12, April).

The miRNA system therefore provides a robust platform by which nucleic acids introduced into cells can be silenced in selected cell types in a target tissue, and expressed in others. By including a binding site for a particular given miRNA sequence into an mRNA construct to be introduced into target cells, particularly in or immediately 5' or 3' to a UTR, expression of certain introduced genes can be reduced or substantially eliminated in some cell types, while remaining in others (Brown and Naldini, Nature Reviews Genetics volume 10, pages 578-585 (2009)). The use of the term 'immediately' is understood to be synonymous with terms such as 'highly proximate to' or 'very close to'. When referring to 5' or 3' positioning relative to a UTR sequence it encompasses variants in which typically up to around twenty, suitably not more than fifty, intervening nucleotide bases may be placed between the miRNA binding sequence and the adjacent UTR. It is contemplated that one, or a plurality, of such miRNA binding site sequences can be included in the mRNA construct. Where a plurality of miRNA binding site sequences are present, this plurality may include for example greater than two, greater than three, typically greater than four miRNA binding site sequences. These miRNA binding site sequences may be arranged sequentially, in tandem or at predetermined locations within, 3' to, or 5' to a specified UTR within the mRNA constructs.

miR-122, despite its abundance in healthy non-diseased liver tissue, is reduced in the majority of liver cancers as well as in diseased cells (Braconi et al. 2011, Semin Oncol; 38(6): 752-763, Brown and Naldini Nature 2009; 10 578). By the above-mentioned method, it has been found that when the target tissue is the liver, translation of the introduced mRNA sequences can be facilitated in cancerous liver cells and reduced or substantially eliminated in transfected healthy cells, by including miRNA-122 binding sites (for example, SEQ ID NO: 1) in or adjacent to their 3' UTRs.

In the context of disease-specific expression of introduced polynucleotides, binding sequences for any miRNA sequence which is disrupted in a particular disease—that is, upregulated or downregulated in diseased cells (such as tumour cells) in comparison to non-diseased cells—is considered suitable for use in the invention. Table 2 discusses examples of tumour-associated miRNA binding sequences of this kind which may be used in embodiments of the present invention. It will be appreciated, however, that the present invention is not limited only to instances where a given miRNA or class of miRNAs is downregulated in a first cell type versus a second cell type within a given organ or organ system. On the contrary, it is merely required that there exists a differential expression pattern of a regulatory miRNA between first and second cell types comprised within the organ or organ system. The differential expression of the miRNA can be exploited using the compositions and methods described herein to enable corresponding differential translation of protein products in those cells.

Examples of cancers where evidence has been found for similar differential miRNA expression between healthy and cancer cells include breast (Nygaard et al, BMC Med Genomics, 2009 Jun. 9; 2:35), ovarian (Wyman et al, PloS One, 2009; 4(4):e5311), prostate (Watahiki et al, PloS One, 2011; 6(9):e24950), and cervical cancers (Lui et al. Cancer Research, 2007 Jul. 1; 67(13):6031-43). WO 2017/132552 A1 describes a wide range of miRNAs with differing expression levels in various cancer cells.

TABLE 2

| Tissue/Cancer Type | Implicated miRNA | Expression Profile | Reference |
|---|---|---|---|
| Liver | miRNA-122 | Reduced in cancer cells | Braconi, 2011, Brown, 2009 |
| Liver | miRNA-125 | Reduced in hepatocarcinoma | Coppola N. Oncotarget, 2017. Vol 8 |
| Brain | miRNA-124a | Reduced in glioblastoma | Mazzacurati L. Moleculatherapy 23, 2015 |
| Lung, breast | Let-7 | Reduced in cancer cells | Edge R E et al. Mol Ther 2008; 16: 1437 Yu F. Cell 2007; 131(6): 1109-23 |

TABLE 2-continued

| Tissue/ Cancer Type | Implicated miRNA | Expression Profile | Reference |
|---|---|---|---|
| Pancreas | miRNA-375 | Reduced in cancer cells | Song S, Zhou J et al. Biomed Reports: 393-398, 2013 |

In the pancreas, miRNA-375 expression has been indicated to be high in normal pancreas cells but significantly lower in diseased and/or cancerous tissues (Song, Zhou et al. 2013). This expression has been shown to relate to the stage of cancer, with expression further reduced with more advanced cancer. It is thought that miRNA-375 is involved with the regulation of glucose-induced biological responses in pancreatic β-cells, by targeting 3-phosphoinositide-dependent protein kinase-1 (PDK1) mRNA and so affecting the PI 3-kinase/PKB cascade (El Ouaamari et al. *Diabetes* 57:2708-2717, 2008). An anti-proliferative effect of miRNA-375 is implicated by this putative mode of action, which may explain its downregulation in cancer cells.

The UTR of the mRNA sequences supplied by the present invention can be selected to have similarity, for example greater than 90% similarity, to part or all of a UTR sequence expressed in one of the cell types within the target organ. Particular cell types can have genes which are up- or down-regulated in expression, and the UTR sequence can mediate this regulation, for instance through encouraging the stability or degradation of the relevant mRNA sequences.

As an example, UTRs associated with genes which are known to be upregulated in cancer cells may have one or more features, such as miRNA binding site sequences, which encourage their stability and translation in these cancer cells. By incorporating similar sequences into supplied mRNA sequences, stability and translation can be improved in cancerous cells but not non-cancerous or healthy cells.

It is also considered that the cancer to be treated by the invention may be a secondary cancer in the target tissue, that is, a metastasis from a cancer elsewhere than the target tissue. For example, a liver metastasis might originate from a cancer of the oesophageal, stomach, colon, rectum, breast, kidney, skin, pancreas or lung, and may be adenocarcinoma or another type of cancer. In these cases alternative miRNA sequences may need to be selected in order to provide differential expression in healthy, non-cancerous and/or cancerous cells. Indeed, there may be an increased choice of candidate miRNA sequences in such cases, due to the different tissue origin of metastasised cells.

In certain situations, it is possible that more than one candidate for an miRNA sequence which exhibits differential expression in different cell types in a target tissue may exist. In such cases, it may be advantageous that a plurality of miRNA binding site sequences are included in the mRNA construct, and that these sequences may be substantially different sequences. However, it is also envisaged that each of the plurality of miRNA binding site sequences may be substantially the same sequence.

Combination Therapies
Oncolytic Viruses

As mentioned above, oncolytic viral therapy is the process of using viruses to infect and kill cancer cells, sometimes by direct viral lysis, but also including indirect killing by the stimulation of host anti-tumoural responses. While oncolytic viruses are frequently characterised by having increased activity in cancer cells compared with healthy cells, off-target effects caused by damage to healthy cells have been documented (Russell et al. Nature Biotechnology, 2012).

In order to increase safety and decrease off-target effects, oncolytic viruses may be modified or selected to reduce their virulence, for example by the deletion of virulence factors or genes involved in functions such as intracellular immune system suppression and evasion, viral genome replication, and the takeover of host cell processes. The historical production of safe forms of live viruses for use in vaccination is another source of attenuated viruses. In other cases, particular mutations or even additional genes have been seen to enhance oncolytic activity in particular oncolytic viruses. Non-exhaustive examples of the virulence genes commonly added, mutated or deleted in oncolytic viruses may be found in Table 3.

TABLE 3

| Oncolytic Virus | Mutation | Reference |
|---|---|---|
| Vesicular Stomatitis Virus, marabavirus | G protein (Q242R mutation) M protein (L123W mutation) | Brun et al 2010, Mol Ther.; 18(8): 1440-1449. |
| Measles virus | NIS gene - Human thyroidal iodide symporter | Aref et al 2016, Viruses, 8, 294 |
| Newcastle disease virus | Fusion protein (F) cleavage site | Vigil et al 2007 Cancer Res; 67: (17). |
| Parvovirus | NS protein NS1 | Marchini et al 2015 Virology Journal 12: 6 |
| Herpes Simplex Virus Type 1 (HSV-1) | Viral ribonucleotide reductase (ICP6) inactivation; serine/threonine-protein kinase (US3) inactivation; ICP34.5 and ICP47 inactivation (Neurovirulence and immune system evasion); UL43 inactivation (Cell fusion) inactivation; UL49.5 inactivation (T-cell evasion) inactivation; UL55 and UL56 | Liu et al (2003) Gene Therapy volume 10, 292-303; Goldsmith et al 1998 J Exp Med. 187(3): 341-348; |
| Adenovirus | E1B-55, E3, E1a promoter, E3 gp19 kD, E1A 924 bp), E1A, deletion in E3 and E4, E3 quaitotal deletion, chimeric ad3/Ad11p E2B region, E3-6.7K + gp19K E1A | Baker et al 2018, Cancers, 10, 201 |

The attenuation or modification of oncolytic viruses in this way can play a role in the selectivity of oncolytic viruses to cancer cells: since the process of carcinogenesis often involves the inactivation of genes that play protective roles against both cancer (such as by regulating cell division or apoptosis), and viral infection, oncolytic viruses which are attenuated as described can retain their virulence in cancer cells, due to the absence of the usual antiviral genes in these cells. Therefore in healthy cells the attenuated virus cannot defend against the normal antiviral responses, and is eliminated, whereas in cancer cells this response is absent, and the virus can lyse the cells. However, this approach is rarely completely effective, as firstly partial inactivation of antiviral responses in cancer cells is more common than a complete lack of antiviral activity (Haralambieva et al, Mol. Ther., 2007), meaning that virulence can still be reduced in these cells, and secondly infection of healthy cells can still occur.

Similarly, as viruses typically utilise the cellular machinery of the host cell in order to replicate their genomes, but this machinery is typically downregulated in healthy, quiescent, non-replicating cells which are not replicating their own genomes, many viruses possess genes which reactivate or compensate for the host machinery. For example, ribonucleotide reductase enzymes are necessary for the production of deoxyribonucleotides from ribonucleotides; these enzymes are typically downregulated in quiescent host cells, and several viruses possess genes for their own enzyme of this type, in order to have a source of deoxyribonucleotides. Since replicating cancer cells may have these enzymes reactivated, an attenuated oncolytic virus with its own ribonucleotide reductase enzyme gene deleted can still replicate in cancer cells. However, for reasons similar to the above, this approach may not be completely effective, either in protecting healthy cells from infection, or in restoring virulence in cancer cells. For example, not all cells in a tumour are replicating at any given time, and as such sufficient deoxyribonucleotides may not be available for viral replication in the majority of cancer cells.

Following the above, when a composition or method according to the present invention is used in conjunction with oncolytic viral therapy, the therapeutic enhancement factor provided by the constructs of the invention may be a factor which increases the efficacy of the oncolytic virus in cancer cells, for example enhancing replication of the virus, or the ability of the virus to lyse the cells in which it resides. In particular, where the oncolytic virus has been modified to attenuate its function, for example by the deletion of one or more genes for virulence factors, the therapeutic factor may replace the deleted gene with mRNA for a gene product which is a copy of the viral gene product, or a gene product with substantial homology to the deleted gene, or which otherwise compensates for the deletion of the gene. In such embodiments, by the differential expression in healthy and cancerous cells which is made possible by the invention, the replacement gene product can be expressed only in cancer cells, enhancing viral activity and lysis in these cells, rather than in healthy cells, where expression of the provided mRNA is inhibited by the presence of the miRNA binding sites.

By similar means, mRNA coding for factors which increase the resistance of cells to oncolytic viruses can be expressed preferentially in healthy cells, again promoting viral activity in cancerous cells compared to healthy cells.

A benefit of this approach is that, unlike previous therapies using oncolytic viruses, it does not rely on which cellular antiviral genes and processes may be inactivated due to carcinogenesis, nor on cell replication processes which may be activated in some cancer cells but not others. As a result, a greater scope of which virulence genes can be deleted from oncolytic viruses is allowed. Thus, oncolytic viruses can be modified to completely lack replicative ability in healthy cells, and, in cancer cells where the function of the deleted virulence genes are replaced by means of the invention, the virus can be restored to full potency. As a result, side effects can be reduced, and efficacy increased. Similarly, since the differential expression of the provided mRNA relies on miRNA expression differences between cancer and healthy cells, virulence can be restored in all transfected cancer cells, and not only those that, for example, are undergoing replication at time of administration.

In a particular embodiment, the oncolytic virus is HSV-1, part of the herpesvirus family. Attenuated versions of HSV may be engineered or selected to be deficient in ICP6, which encodes a viral ribonucleotide reductase (Aghi et al, Oncogene. 2008) and/or in US3, which encodes a serine/threonine-protein kinase, and plays several roles in the virus' lifecycle, including blocking host cell apoptosis (Kasuya et al, Cancer Gene Therapy, 2007).

Cytokines

It is contemplated that the compositions and methods as described herein may act to induce an immune response against disease. In particular, immune responses may be induced against cancer cells. The process of carcinogenesis frequently involves ways in which the cancer cells attempt to evade the immune system, involving changes to the antigens produced and displayed by these cells, In some embodiments, the mRNA provided by the invention comprises at least one polynucleotide encoding a protein that is a bispecific T-cell engager (BiTE), an anti-immunosuppressive protein, or an immunogenic antigen. The term "anti-immunosuppressive protein" as used herein is a protein that inhibits an immunosuppressive pathway.

The invention encompasses compositions supplying mRNA coding for an anti-immunosuppressive protein that is an anti-regulatory T-cell (Treg) protein or an anti-myeloid-derived suppressor cell (MDSC) protein. In some embodiments, the anti-immunosuppressive protein is a VHH-derived blocker or a VHH-derived BiTE.

The term "immunogenic antigen" as used herein refers to a protein that increases an inflammatory or immunogenic immune response. In particular embodiments, the anti-immunosuppressive and immunogenic antigens induce an anti-tumour immune response. Examples of such proteins include antibody or antigen binding fragments thereof that bind to and inhibit immune checkpoint receptors (e.g., CTLA4, LAG3, PD1, PDL1, and others), proinflammatory cytokines (e.g., IFNγ, IFNα, IPNβ, TNFα, IL-12, IL-2, IL-6, IL-8, GM-CSF, and others), or proteins that binding to and activate an activating receptor (e.g., FcγRI, FcγIIa, FcγIIIa, costimulatory receptors, and others). In particular embodiments, the protein is selected from EpCAM, folate, IFNβ, anti-CTLA-4, anti-PD1, A2A, anti-FGF2, anti-FGFR/FGFR2b, anti-SEMA4D, CCL5, CD137, CD200, CD38, CD44, CSF-1R, CXCL10, CXCL13, endothelin B Receptor, IL-12, IL-15, IL-2, IL-21, IL-35, ISRE7, LFA-1, NG2 (also known as SPEG4), SMADs, STING, TGFβ, and VCAM1.

The invention encompasses compositions supplying mRNA coding for functional macromolecules to targeted cell populations used in cell-based therapies. In some embodiments, the targeted cell population is a genetically engineered T cell population. In some embodiments, the targeted cell population is a population of chimeric antigen receptor T cells (CAR-T cells).

The coding mRNA and the delivery particles may be used to attract a population of immune cells or a combination of immune cell populations to a particular site in a subject. In some embodiments, the coding mRNA and the delivery particles are used to attract immune cells to the tumour microenvironment. In some embodiments, the coding mRNA and the delivery particles are used to overcome insufficient migration of an immune cell to the tumour microenvironment. In some embodiments, the immune cell is a T cell, a natural killer (NK) cell, a B cell, an antigen-presenting cell (APC) such as a macrophage or dendritic cell, or any combination thereof. In some embodiments, the coding mRNA and the delivery particles are used to attract CAR-T cells to the tumour microenvironment.

The coding mRNA and the delivery particles may be used to overcome insufficient migration of CAR T cells to the tumour microenvironment. In some embodiments, the delivery particles specifically target the tumour microenvironment, and the coding mRNA encodes a gene product that attracts or otherwise recruits CAR-T cells to the tumour microenvironment. In some embodiments, the coding mRNA expresses a chemokine. By way of non-limiting example, the coding mRNA can encode a chemokine that attracts T-cells such as CCL2, CCL3, CCL4, CCL5, CCL20, CCL22, CCL28, CXCL8, CXCL9, CXCL10, CXCL11, CXCL12, XCL1, and any combination thereof. In situations where the reverse effect is desired, such as in autoimmune disease, the coding mRNA can express blockers, antagonists and/or inhibitors of the above-mentioned factors.

The coding mRNA and the delivery particles may be used to transiently express the coding mRNA in the tumour microenvironment. In some embodiments, the coding mRNA encodes a cytokine or other gene product involved in regulating the survival, proliferation, and/or differentiation of immune cells in the tumour response, such as, for example, activated T cells and NK cells. By way of non-limiting example, the coding mRNA can encode for a cytokine such as IL-1, IL-2, IL-4, IL-6, IL-8, IL-10, IL-12, IL-17, IL-33, IL-35, TGF-beta, and any combination thereof. Again, in situations where the reverse effect is desired, such as in autoimmune disease, the coding mRNA can express blockers, antagonists and/or inhibitors of the above-mentioned factors.

The compositions supplying mRNA may be designed to target particular cell subtypes and, upon binding to them, stimulate receptor-mediated endocytosis, thereby introducing the synthetic mRNA they carry to the cells, which can now express the synthetic mRNA. Because nuclear transport and transcription of the transgene are not required, this process is fast and efficient.

In some embodiments, the mRNA nanoparticle delivery system delivers an mRNA that codes for a gene-editing agent to a target cell population. In some embodiments, the mRNA codes for a sequence-specific nuclease that targets a gene locus and disrupts expression of one or more endogenous gene produces in the target cell population. In some embodiments, the mRNA codes for a sequence-specific nuclease that targets a T cell receptor (TCR)-related gene locus, thereby disrupting expression of one or more domains in the TCR.

In some embodiments, the mRNA nanoparticle delivery compositions may be used to deliver an mRNA that codes for one or more agents that program engineered T cells toward a desired phenotype. In some embodiments, the mRNA nanoparticle delivery compositions may be used to induce markers and transcriptional patterns that are characteristic of a desired T cell phenotype. In some embodiments, the mRNA nanoparticle delivery compositions may be used to promote development of CD26L+ central memory T cells (Tcm), which have been shown to improve CAR-T treatment. (See e.g., Moffett, Coon supra). In some embodiments, compositions supply mRNA encoding one or more transcription factors to control cell differentiation in a target cell population. In some embodiments, the transcription factor is Foxo1, which controls development effector-to-memory transition in CD8 T-cells.

In some embodiments, the mRNA nanoparticle delivery compositions include a surface-anchored targeting domain that is specific for a T cell marker, such as, for example, a surface antigen found on T cells. In some embodiments, the surface-anchored targeting domain is specific for an antigen that selectively binds the nanoparticle to T-cells and initiates receptor-induced endocytosis to internalize the mRNA nanoparticle delivery compositions. In some embodiments, the surface-anchored targeting domain selectively binds CD3, CD8, or a combination thereof. In some embodiments, surface-anchored targeting domain is or is derived from an antibody that selectively binds CD3, CD8, or a combination thereof.

By means of the invention, differential expression of the above-mentioned gene products can be achieved in different cell types, for example, in healthy cells, non-diseased, diseased and cancer cells. By this method, an immune response can be triggered targeted towards diseased cells while sparing the non-diseased or healthy cells.

The introduction of coding nucleotides sequences into a target cell most often requires the use of a delivery agent to transfer the desired substance from the extracellular space to the intracellular environment. Frequently, such delivery agents are in the form of delivery particles, which may undergo phagocytosis and/or fuse with a target cell. Delivery particles may contain the desired substance by encapsulation or by comprising the substance within a matrix or structure.

The delivery particles of the present invention may be targeted to the cells of the target tissue. This targeting may be mediated by a targeting agent on the surface of the delivery particles, which may be a protein, peptide, carbohydrate, glycoprotein, lipid, small molecule, nucleic acid, etc. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferrin, asialycoproteins, gp120 envelope protein of the human immunodeficiency vims (HIV), carbohydrates, receptor ligands, sialic acid, aptamers etc.

Typically, the delivery particles comprise aminoalcohol lipidoids. These compounds may be used in the formation of particles including nanoparticles, liposomes and micelles, which are particularly suitable for the delivery of nucleic acids. An illustrative example for the production of nanoformulations comprising particles according to some embodiments of the invention may be found in the Examples.

When administered to a subject, a therapeutic component is suitably administered as part of a composition that comprises a pharmaceutically acceptable vehicle. Acceptable pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilising, thickening, lubricating and colouring agents may be used. When administered to a subject, the pharmaceutically acceptable vehicles are preferably sterile. Water is a suitable vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skimmed milk, glycerol, propylene, glycol, water, ethanol and the like. Pharmaceutical compositions, if desired, can also contain minor amounts of wetting or emulsifying agents, or buffering agents.

The medicaments and pharmaceutical compositions of the invention can take the form of liquids, solutions, suspensions, gels, modified-release formulations (such as slow or sustained-release), emulsions, capsules (for example, capsules containing liquids or gels), liposomes, microparticles, nanoparticles or any other suitable formulations known in the art. Other examples of suitable pharmaceutical vehicles are described in Remington's Pharmaceutical Sciences, Alfonso R. Gennaro ed., Mack Publishing Co. Easton, Pa., 19th ed., 1995, see for example pages 1447-1676.

For any compound or composition described herein, the therapeutically effective amount can be initially determined from in vitro cell culture assays. Target concentrations will be those concentrations of active component(s) that are capable of achieving the methods described herein, as measured using the methods described herein or known in the art.

As is well known in the art, therapeutically effective amounts for use in human subjects can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

It is contemplated that embodiments of the invention may include compositions formulated for use in medicine. As such, the composition of the invention may be suspended in a biocompatible solution to form a composition that can be targeted to a location on a cell, within a tissue or within the body of a patient or animal (i.e., the composition can be used in vitro, ex vivo or in vivo). Suitably, the biocompatible solution may be phosphate buffered saline or any other pharmaceutically acceptable carrier solution. One or more additional pharmaceutically acceptable carriers (such as diluents, adjuvants, excipients or vehicles) may be combined with the composition of the invention in a pharmaceutical composition. Suitable pharmaceutical carriers are described in 'Remington's Pharmaceutical Sciences' by E. W. Martin. Pharmaceutical formulations and compositions of the invention are formulated to conform to regulatory standards and can be administered orally, intravenously, topically, intratumorally, or subcutaneously, or via other standard routes. Administration can be systemic or local or intranasal or intrathecal.

Further intended are embodiments wherein the composition of some embodiments of the invention is administered separately to or in combination with alternative antitumoral or otherwise anti-cancer therapeutic components. These components can include oncolytic viruses, small molecule drugs, chemotherapeutics, radiotherapeutics or biologicals. The components may be administered concurrently with the composition of the invention, and may be comprised within the delivery particles, or may be administered separately, before or after administration of the composition of the invention, by any means suitable.

It is also contemplated that the composition of some embodiments of the invention may be used in in vitro and/or ex vivo methods, for example in a laboratory setting. An example of an in vivo method is wherein a composition comprising a delivery particle and an mRNA sequence as described herein is administered to target in vitro cells, and the miRNA binding site sequences comprised in the mRNA sequence allow for differential expression of the coding sequence of the mRNA in different cell types within the target in vitro cells. Similarly, a method is contemplated wherein a composition comprising a delivery particle and an mRNA sequence as described herein is administered to a target ex vivo sample taken from an animal, and the miRNA binding site sequences comprised in the mRNA sequence allow for differential expression of the coding sequence of the mRNA in different cell types within the target sample.

The device of the invention is exemplified by, but in no way limited to, the following Examples.

EXAMPLES

General Protocols
Cell Lines

Human liver hepatocarcinoma (HCC) HepG2 (ATCC® HB-8065™) and Hep3B (ATCC® HB-8064™) cell were purchased from ATCC. Cells were cultured in Eagle's Minimum Essential Medium (EMEM) (Cellgro, USA), 10% FBS (HyClone, USA), streptomycin (100 μg/mL) and penicillin (100 U/mL$^{-1}$) (Cellgro) as monolayers at 37° C. in an atmosphere of 5% $CO_2$. HepG2 cells were grown on collagen (Gibco, USA) coated plates at a collagen concentration of 5 μg/cm$^2$.

HMCPP5 (pooled plateable human hepatocytes; a mixture of plateable primary hepatocytes produced by combining cells from 5 individual donors) were purchased from ThermoFisher Scientific, USA. Cells were plated in Williams E Medium (WEM), supplemented with 5% FBS, 1 μM Dexamethasone, and Cocktail A (Penicillin/Streptomycin, Human Recombinant Insulin, GlutaMax, and HEPES, pH 7.4). 24 hours after plating, the WEM/Cocktail A medium was changed to maintenance/incubation medium WEM supplemented with 0.1 μM Dexamethasone and Cocktail B (Penicillin/Streptomycin, ITS (Human Recombinant Insulin, Human transferrin, selenous acid, BSA, linoleic acid), GlutaMax, and HEPES, pH 7.4) as monolayers at 37° C. in an atmosphere of 5% $CO_2$. During all experiments, cells were cultured in WEM/Cocktail B medium with the exception of during transfection with nanoformulated mRNA. WEM/Cocktail B medium was exchanged for fresh every 3 days. HMCPP5 cell growth on collagen (Gibco) coated plates at protein concentration 5 μg/cm$^2$.

Aml12 (mouse healthy hepatocytes) were purchased from ATCC, USA. Cells were seeded into a 12-well plate at a density of 1×10$^5$/well.

Vector Constructs
Constructing of pMRNA-CTx-mRNA Template

Plasmid pMRNA-CTx-mRNA template forming matrices for in vitro synthesis of all mRNA used in the experiments were constructed according to commercially available mRNAExpress™ mRNA Synthesis Kit (SBI, USA). All plasmids were propagated in *E. coli* (Invitrogen, USA) and purified using Qiagen Mini or Maxi Kit (Qiagen, USA). Restriction maps of all plasmids were generated using pDRAW32 software (www.acaclone.com).

Cloning Method 1—Restriction Endonuclease

Figure 2:
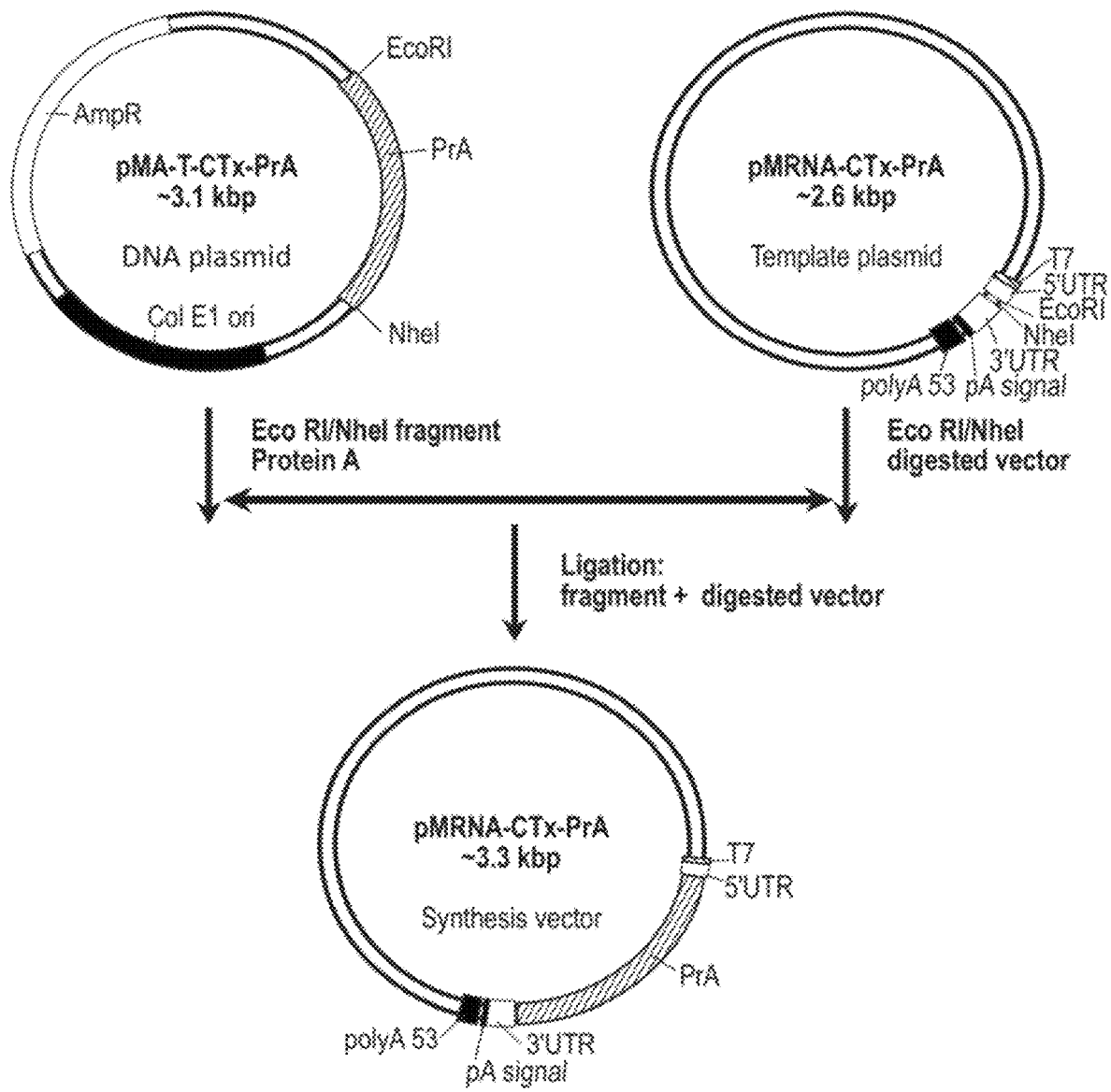
FIG. 2 shows an example of a cloning method to produce DNA synthesis vectors, which vectors were used to produce the mRNA constructs according to embodiments of the invention.

As shown in FIG. 2, the sequence of one or more genes, flanked with Kozak sequence for optimal translation directly before the ATG codon at the 5'-end or a stop codon (TAA, TAG, TGA) at the 3'-end of gene, were synthesised by company GeneArt (without codon optimisation) and delivered as plasmid DNA (referred to as DNA plasmids or vectors), shown in FIG. 2 as pMA-T-CTx-Gene. Proprietary 5' and 3' UTR regions flanking the coding sequence were included in all synthesised sequences (not shown in the appended sequences). The 5' UTR is synthetic, and contains the Kozak sequence, and the 3' UTR is based on a mouse alpha globin UTR and also comprises a poly A tail of 120 bases. To generate the synthesis vector shown in FIG. 2 as pMRNA-CTx-mRNA, a nucleotide fragment containing the gene or genes was cut out from the DNA plasmid using restriction endonucleases, here EcoRI and NheI, and subcloned into EcoRI/NheI restriction sites in the pMRNA template plasmid, this template plasmid comprising T7 promoter recognized by T7 RNA polymerase, 5'- and 3'-UTRs, and a polyA sequence.

Cloning Method 2—Cold Fusion

The sequence of one or more genes, flanked as in Cloning Method 1 with a Kozak sequence and a stop codon (TAA, TAG, TGA), was synthesised by company GeneArt (without codon optimisation) and delivered as a plasmid DNA pMAT-CTx-Gene, with the backbone of this plasmid the same as described above. To construct the pMRNA-CTx-mRNA template vector, the Cold Fusion cloning kit (SBI, USA) was deployed. Briefly, the gene sequence from the DNA plasmid was amplified by PCR with specific primers, the primers adding an extension of 14 bases of homology to each end of the gene sequence. These 14 bases were designed to be homologous to the ends of the linearised vector produced by digestion of the template plasmid with a restriction endonuclease cutting in the multicloning site located between the 5' and 3' UTRs. To produce the synthesis vector, the predicted PCR product was purified by PCR purification kit (Qiagen, USA) and incorporated to the pMRNA template plasmid following a Cold Fusion reaction (homology recombination) according to the manufacturer's protocol.

Construction of a Template Containing miRNA Binding Site Sequences

Figure 3:
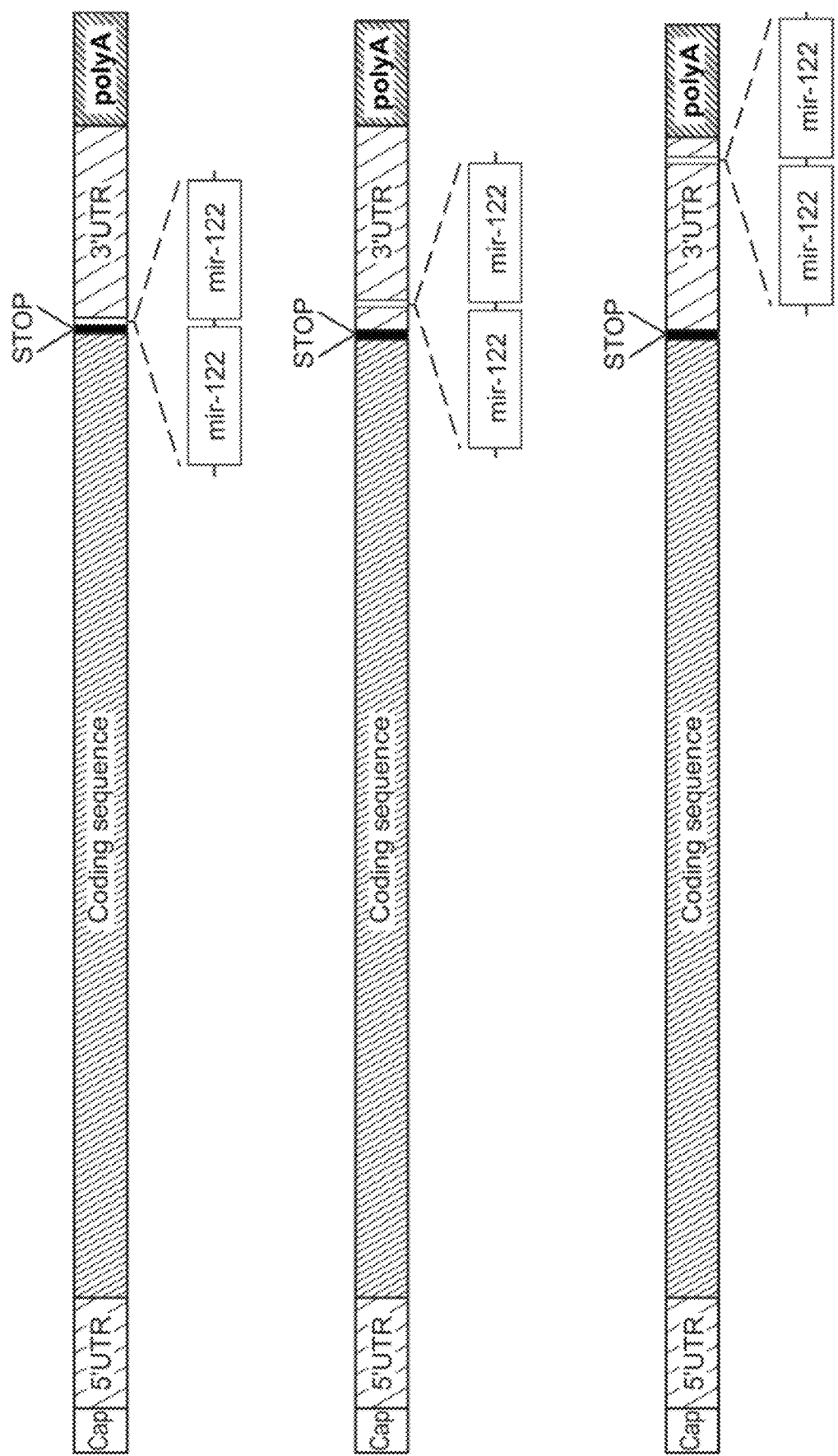
FIG. 3 shows three variants of mRNA constructs used in embodiments of the invention, and illustrated in FIG. 4, and possible options for the insertion point of a pair of miRNA binding sequences (here sequences that bind to miR-122) within or adjacent to a UTR sequence located 3' to the coding sequence.

For the production of mRNA sequences comprising miRNA binding site sequences, for which examples using miR-122 are shown in FIG. 3, exemplary methods of creating three variants are discussed below. In variant 1, two copies of the miRNA binding site sequence are included between the stop codon and the +1 position of the 3' UTR. In variant 2, two copies of the miRNA binding site sequence are included at the beginning or 5' end of the 3' UTR, and in variant 3, two copies of the miRNA binding site sequence are included at the end or 3' end of the 3' UTR.

Figure 4:
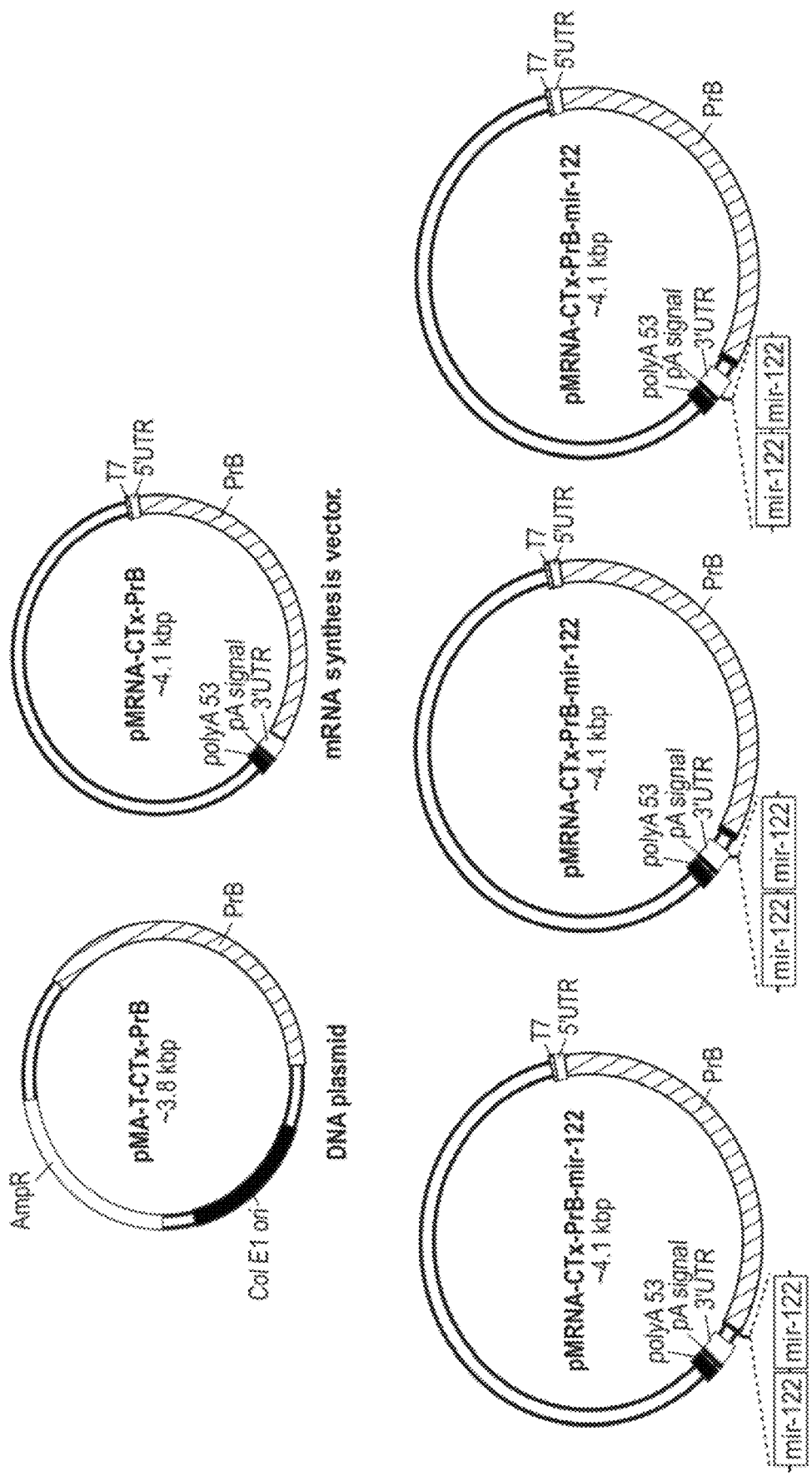
FIG. 4 shows examples of DNA plasmids, template plasmids, as well as synthesis vectors for producing the mRNA constructs depicted in FIG. 3.

FIG. 4 shows examples of synthesis vectors comprising these three variants, using as an example Protein B, a gene of approximately 1400 base pairs.

Variant 1

Figure 5:
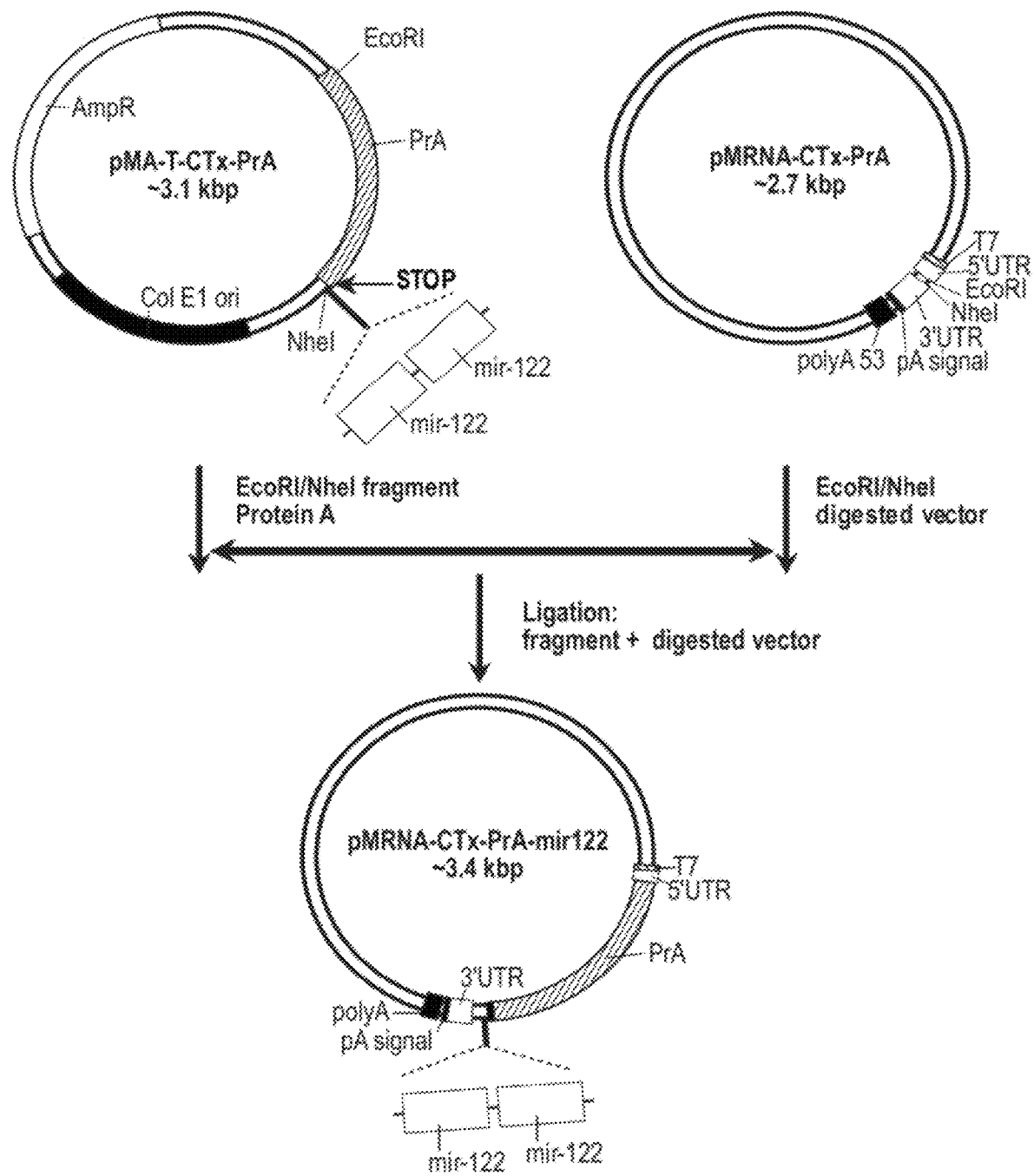
FIGS. 5, 6 and 7 show examples of methods which may be used to produce a synthesis vector for producing the mRNA construct variants as depicted in FIG. 3.

As shown in FIG. 5, the sequence of one or more genes, flanked as in the above methods with a Kozak sequence and a stop codon (TAA, TAG, TGA), and additionally comprising two copies of a miRNA binding site sequence following the stop codon, was synthesised by company GeneArt (without codon optimisation) and delivered as a plasmid (here illustrated again with Protein A) DNA pMAT-CTx-Gene, with the backbone of this plasmid the same as described above. This sequence was then cloned into the template plasmid to create a synthesis vector by either of the methods described above.

Variants 2 and 3

Figure 6:
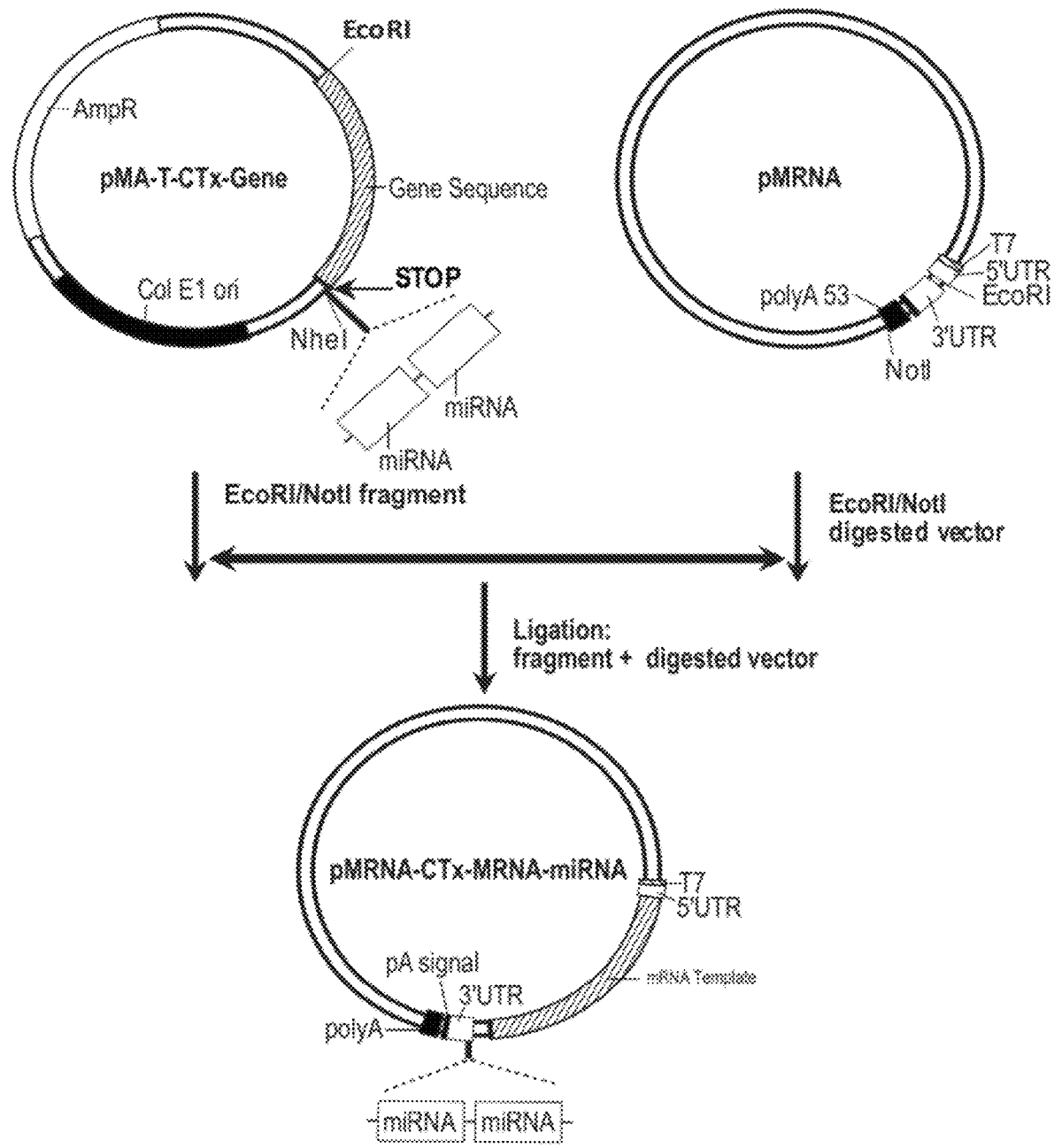
Figure 7:
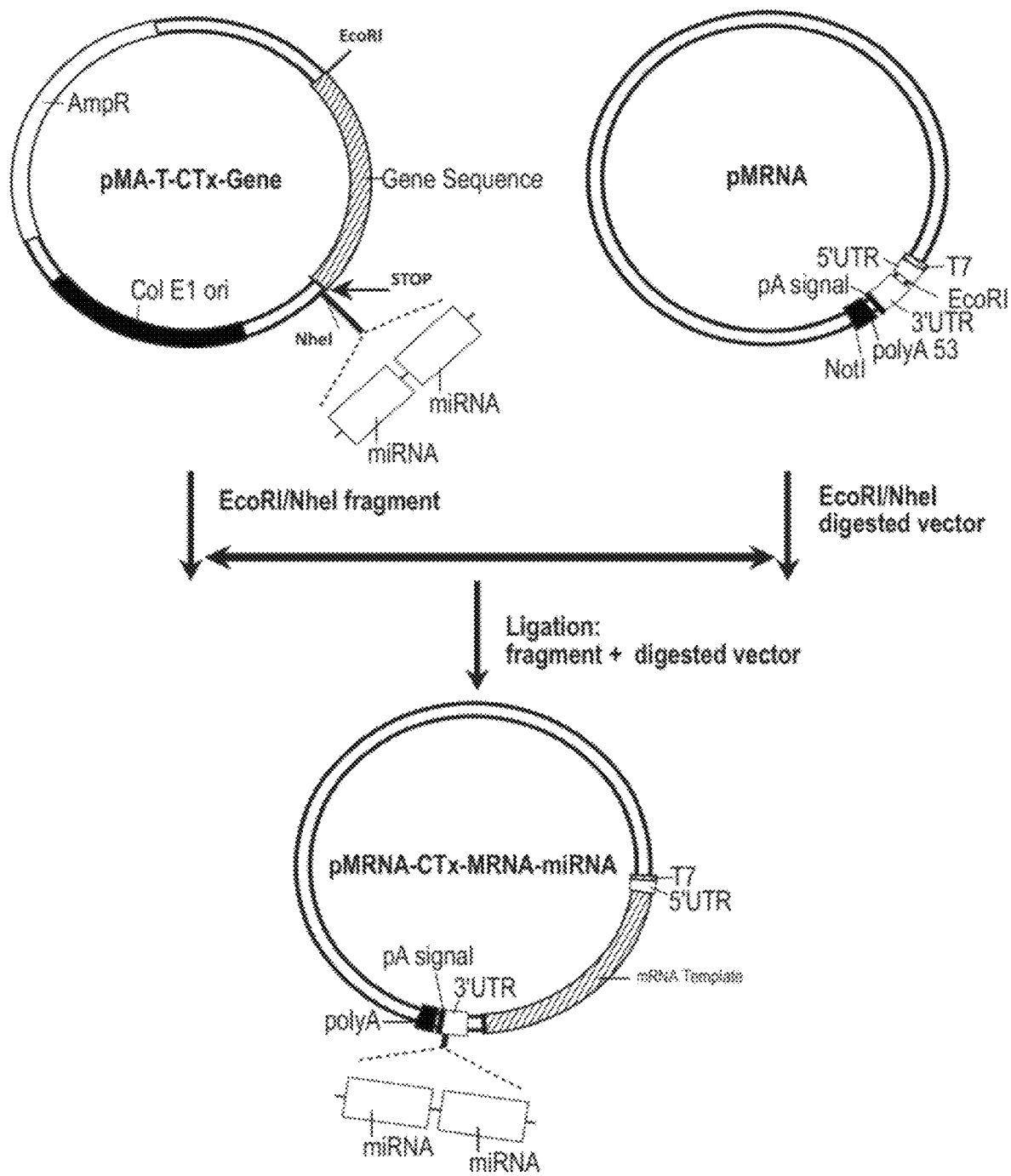
Figure 8:
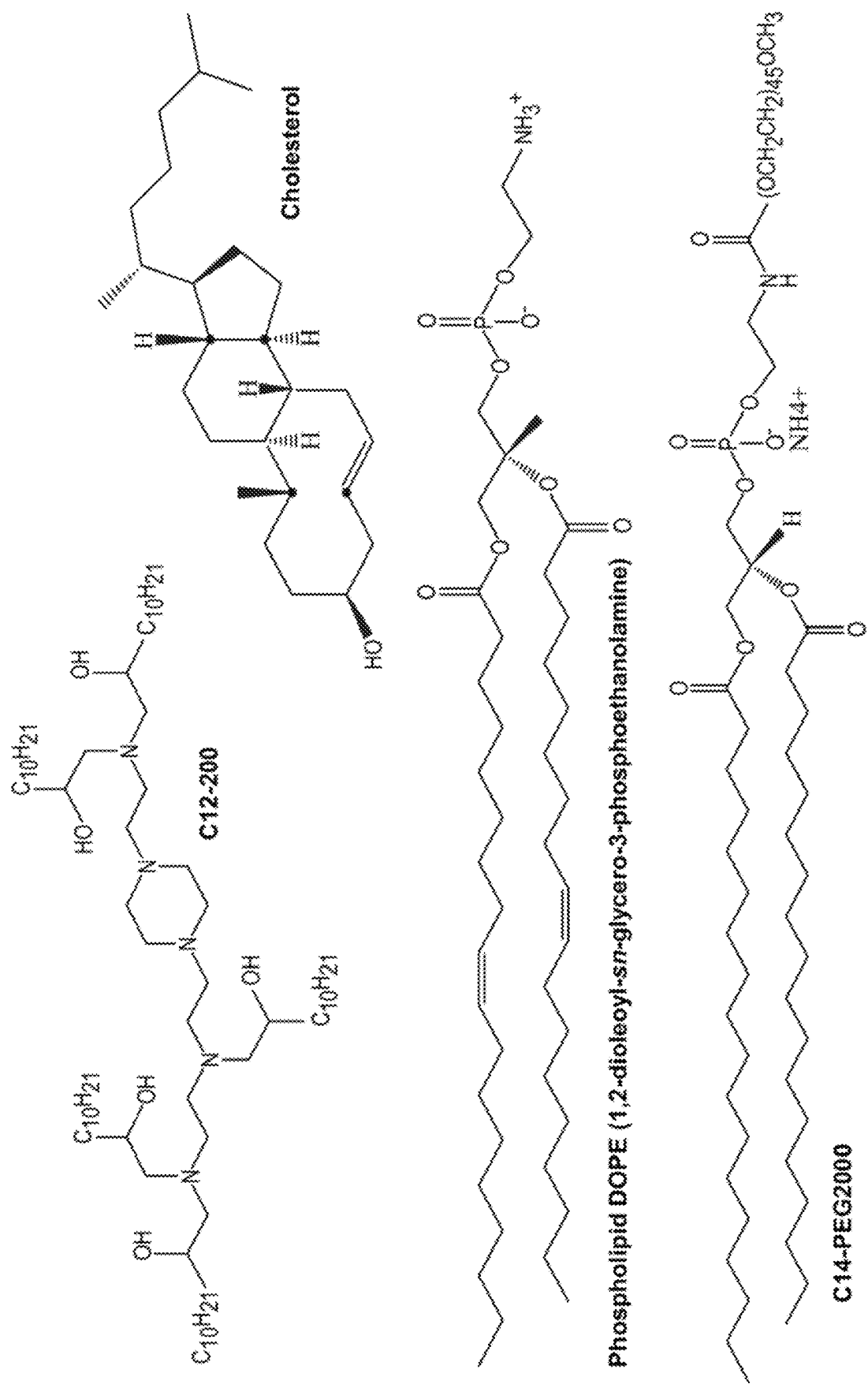
FIG. 8 shows the chemical formulae of examples of constituent compounds that can be used in the preparation of delivery particles according to an embodiment of the invention.

The sequence of one or more genes, flanked as in the above methods with a Kozak sequence and a stop codon (TAA, TAG, TGA), and additionally comprising a 3' UTR, including two copies of a miRNA binding site sequence either at the beginning/5' end of this region (variant 2, as shown in FIG. 6) or at the end/3'end of this region (variant 3, as shown in FIG. 7), was synthesised by company GeneArt (without codon optimisation) and delivered as a plasmid DNA pMAT-CTx-Gene, with the backbone of this plasmid the same as described above. This sequence was then cloned into a template plasmid to create a synthesis vector by either of the methods described above, modified in that restriction enzymes were chosen (here EcoRI and NotI) to remove the 3' UTR from the template vector, such that the 3' UTR from the supplied DNA sequence would be present in the final synthesis vector, as this contained the miRNA binding site sequences.

In Vitro Transcription (IVT) of mRNA with In Vitro mRNA Synthesis

To perform IVT of mRNA with or without miRNA-modified 3' UTRs the commercially available mRNAExpress™ mRNA Synthesis Kit was used. DNA templates for IVT vectors were constructed as described in the protocols as set forth above. The procedure of in vitro mRNA synthesis was performed according to the manufacturer's protocol. Briefly, a polyA tail was added to the DNA sequence using a PCR reaction with specific 5' and 3' primers (provided with the kit). During in vitro transcription, the synthesised mRNA on DNA template was capped with anti-reverse cap analog (ARCA)-modified nucleotides (5-Methylcytidine-5'-Triphosphate). Cap analog, pseudouridine-5'-triphosphate and poly-A tail were incorporated in the in vitro transcribed mRNAs to enhance stability and to reduce the immune response of host cells.

Synthesis of $DMP^{CTx}$ and Formulation of mRNA

The delivery and modulation platform of Combined Therapeutics ($DMP^{CTx}$) formulation is a multi-component nanoparticle of ionizable lipid-like material C12-200, phospholipid DOPE, cholesterol and lipid-anchored polyethylene glycol C14-PEG-DSPE2000 mixture. This particular composition of $DMP^{CTx}$ and specific weight ratio (10:1) of C12-200: mRNA and molar [%] composition of lipid-like material, phospholipid, cholesterol and PEG (Table 4) was optimized and has revealed high efficiency of the formulation in vivo (Kauffman K. J., Nano Letter. 2015, 15, 7300-7306). The chemical structures of these exemplary components are shown in FIG. 8.

To synthesize $DMP^{CTx}$ an ethanolic solution (Mix A) of C12-200 (WuXi, China), as shown in FIG. 9A, phospholipid DOPE (1,2-dioleyl-snglycero-3-phosphoethanolamine) (Avanti Polar Lipids, Alabaster, AL, USA), cholesterol (Sigma, USA) and C14-PEG-DSPE2000 (Avanti Polar Lipids, Alabaster, AL, USA) and an aqueous buffered solution of mRNA (Mix B) in (10 mM citrate, pH 4.5) was prepared. Both ethanolic Mix A and aqueous Mix B at ratio 3:1 were mixed/combined using syringe pumps and microfluidic chip device (Chen D, at al J. Am. Chem. Soc. 2012, 134 (16), 6948-6951). Alcoholic solution of nanoformulated mRNA from microfluidic chip was collected to the 1.5 mL tubes.

TABLE 4

| Compound | Weight Ratio | Formulation Molar Composition [%] |
|---|---|---|
| C12-200:mRNA | 10:1 | n/a |
| C12:200 | n/a | 35 |
| DOPE | | 16 |
| Cholesterol | | 46.5 |
| C14-PEG-DSPE200 | | 2.5 |

To remove alcohol after formulation the $DMP^{CTx}$-mRNA mixture was transferred to the Slide-A-Lyzer® Dialysis Cassette G2 and dialyzed in PBS in room temperature on the magnetic stirrer for 4 hours. Subsequently, formulated mRNA using syringe with 18 gauge, 1-inch beveled needles was transferred to new 1.5 mL tubes and ready for characterization.

To calculate efficacy of mRNA encapsulation RiboGreen RNA assay (Invitrogen) was used according manufacture protocol. Polydispersity (PDI) and size of lipid nanoparticles was measured using dynamic light scattering (ZetaPALS, Brookhaven, Instruments). The surface charge of DMP$^{CTx}$ (Zeta potential) was measured using the same instrument. Solutions of mRNA sequences with and without two copies of an miR-122 sequence connected by a linker (SEQ ID NO: 2) and inserted after the stop codon of the coding mRNA sequence were prepared from a 1.05 and 1 mg/ml stock, respectively. Examples of parameters after encapsulation of mRNA sequences comprising the mCherry (mCh) sequence, the sequence of protein A, a human protein of approximately 25 kDa, are shown in Table 5, including the size, encapsulation efficiency and polydispersity of the delivery and modulation platform of Combined Therapeutics (DMP$^{CTx}$). An illustrative diagram of a delivery particle according to DMP$^{CTx}$ may be seen in FIG. 9B.

TABLE 5

| mRNA | Formulation | Conc (ug/mL) | Encapsulation efficacy (%) | Size (nm) | Poly-dispersity |
|---|---|---|---|---|---|
| Protein A - 022 | C12-200 | 202 | 78 | 93 | 0.12 |
| US3 - 052 | | 172 | 78 | 93 | 0.12 |
| mCherry - 062 | | 120 | 76 | 96 | 0.12 |

Differential Expression of Delivered mRNA Constructs In Vitro

To investigate the potential of the present invention to successfully transfect target cells with construct mRNA and subsequently drive differential expression in different cell types, the DMP$^{CTx}$ mRNA platform, modified with miRNA-122 binding sites, was used in a model of liver hepatocarcinoma.

Transfection of Cell Lines
Fluorescence Imaging and Quantification

Single transfections of the human liver hepatocarcinoma cell lines HepG2 and Hep3B were performed as follows: one day prior to transfection, HepG2 and Hep3B cells were seeded separately into a 12-well plate at a density of $2.7 \times 10^5$/well, and $2 \times 10^5$/well (EMEM/10% FCS), respectively. The next day, cells were transfected either with a vehicle control of PBS alone, with 0.5 μg/well of mRNA-mCherry-DMP$^{CTx}$, or with 0.5 μg/well of mRNA-mCherry-122-DMP$^{CTx}$ (the sequence comprising SEQ ID NO: 3). The transfection was carried out by direct addition of mRNA-DMP$^{CTx}$ to the cultured medium in the well, with gentle mixture of the cultured cells as needed.

Single transfections of HMCPP5 (pooled plateable human hepatocytes), were performed as follows: one day prior to transfection HMCPP5 cells were seeded into a 12-well plate at a density of $2.5 \times 10^5$/well (WEM/Cocktail B). The next day, cells were transfected either with a vehicle control of DMP$^{CTx}$ (PBS), with 0.5 μg/well of mRNA-mCherry-DMP$^{CTx}$, or with 0.5 μg/well of mRNA-mCherry-122-DMP$^{CTx}$. The transfection was carried out by the direct addition of mRNA-DMP$^{CTx}$ to the cultured medium in the well, with gentle mixture of the cultured cells as needed. During transfection of HMCPP5 the WEM/Cocktail B medium was supplemented with 5% FBS. Transfection was carried out in the manner described for liver cancer cells, above. 24 hours after transfection, the medium was again changed to WEM/Cocktail B.

To evaluate constitutive activity and expression of miRNA-122 in healthy human hepatocytes, multiple transfections of HMCPP5 cells were performed as follows: the HMCPP5 cells were seeded and cultured as above, and were transfected with mRNA-mCherry-DMP$^{CTx}$, or mRNA-mCherry-122-DmP$^{CTx}$, three times (MPT) in total, with an interval of 48 hrs between each transfection. Transfection was carried out in the same manner described for single transfections of HMCPP5, as described above.

Single transfections of mouse healthy hepatocytes (Aml12, ATCC, USA) were performed as follows: one day prior to transfection Aml12 cells were seeded into a 12-well plate at a density of $1 \times 10^5$/well. The next day, cells were transfected either with a vehicle control of DMP$^{CTx}$ (PBS), with 0.5 μg/well of mRNA-mCherry-DMP$^{CTx}$, or with 0.5 μg/well of mRNA-mCherry-122-DMP$^{CTx}$. The transfection was carried out by the direct addition of mRNA-DMP$^{CTx}$ to the cultured medium in the well, with gentle mixture of the cultured cells as needed.

Following transfection, mCherry expression in the above cell lines was detected using a fluorescence imaging system (application from EVOS® FL Imaging Systems). Pictures showing mCherry fluorescence were taken 16, 24, 48, 72, 96 and 144 hours after transfection.

Figure 10A:
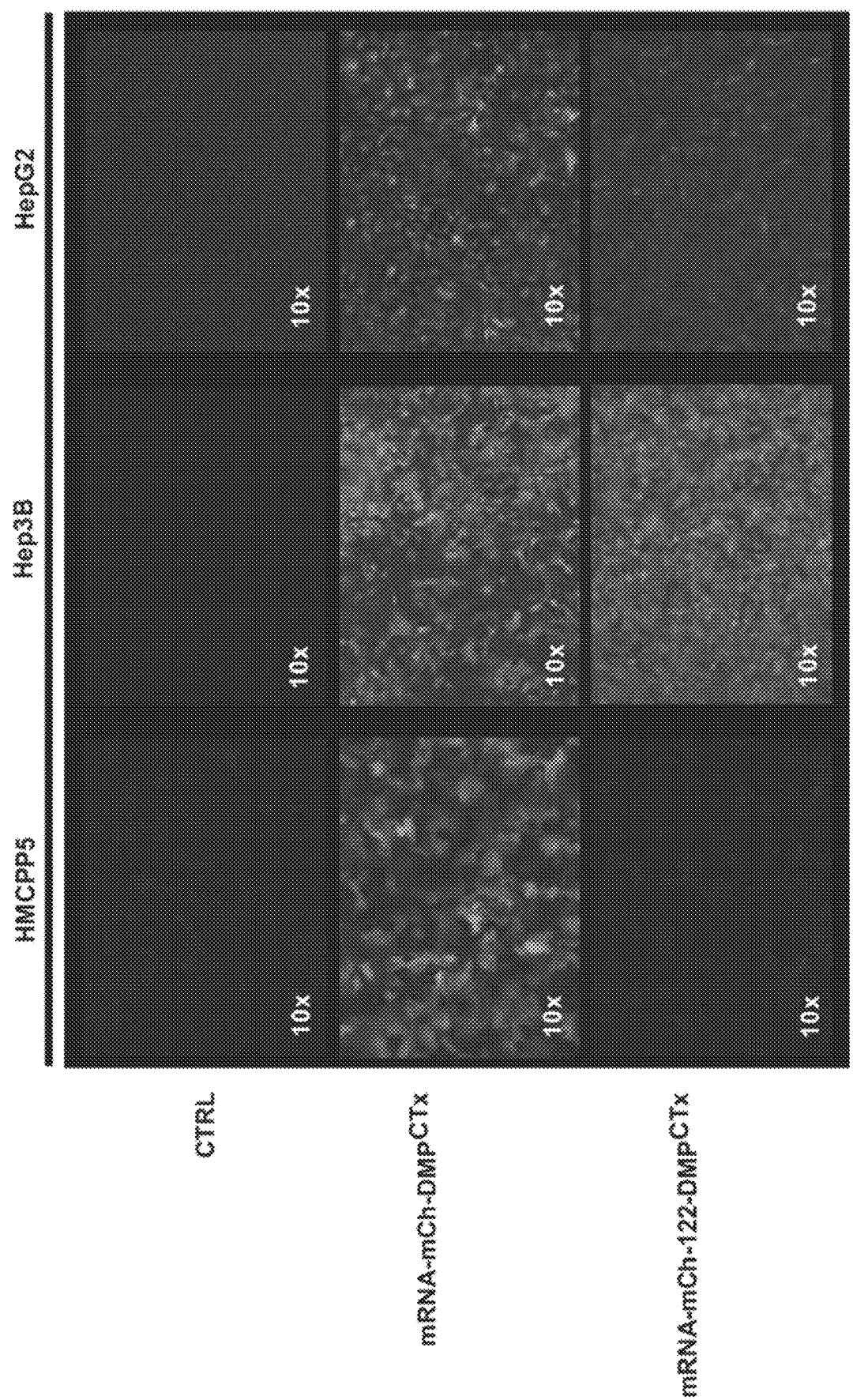
FIG. 10A fluorescent microscopy images indicating the results of an experiment where cells from healthy human hepatocyte culture (Human Plateable Hepatocytes, HMCPP5), human hepatocarcinoma (Hep3B) and human hepatoblastoma (HepG2) cells were transfected in vitro with compositions according to embodiments of the invention. Two delivery particles were administered: one containing a mRNA encoding the fluorescent protein mCherry (mRNA-mCh-DMP$^{CTx}$) and one one containing an mRNA encoding the fluorescent protein mCherry but where differential expression is controlled by miRNA-122 content in the the target cells (mRNA-mCh-122-DMP$^{CTx}$).
Figure 10B:
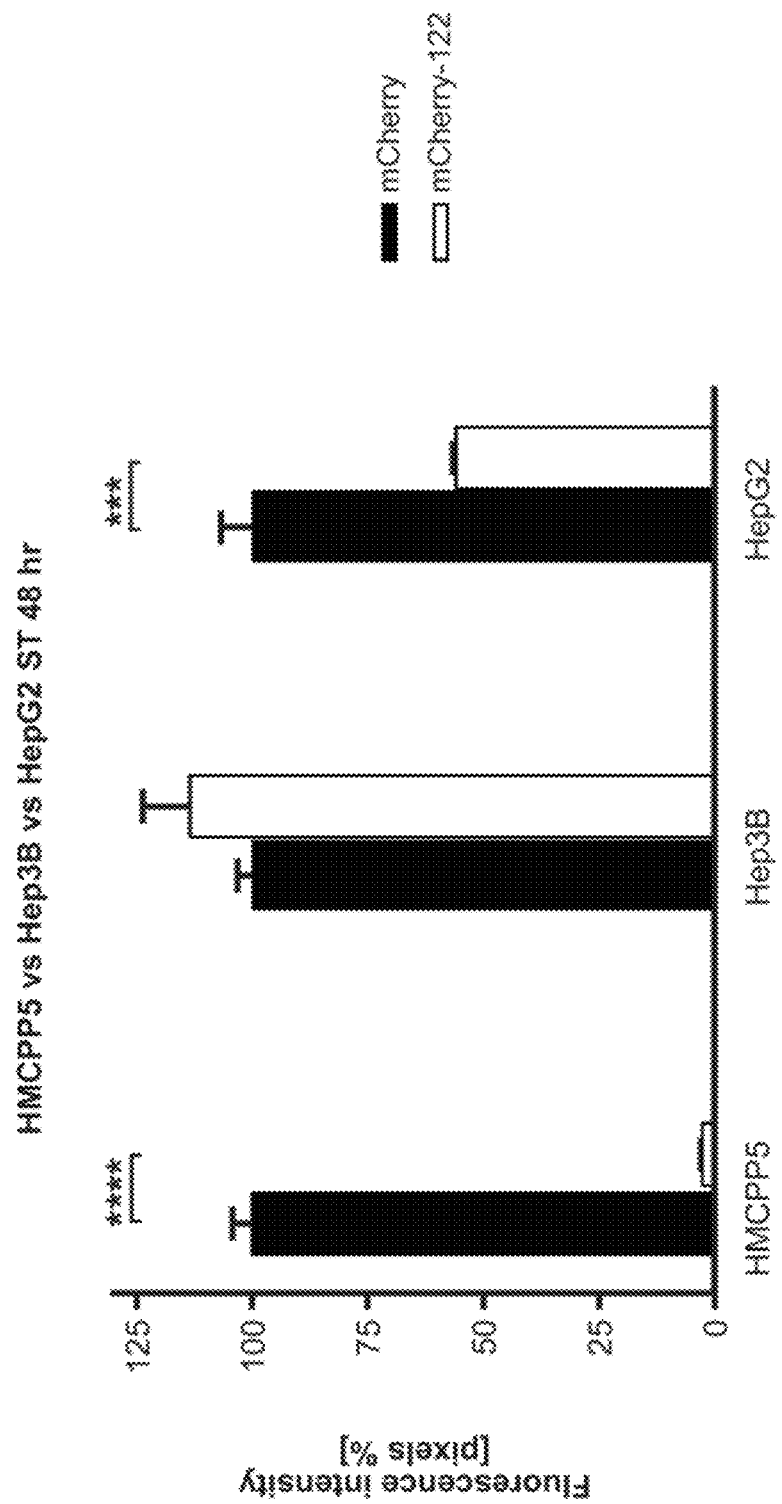
FIG. 10B shows a quantification of fluorescence intensity after 48 hours of cells transfected according to the experiment of FIG. 10A. Results are shown as means±SD. Statistical significance was determined using the t test. Asterisks indicate statistically significant difference between mRNA-mCherry, mRNA-mCherry-122 expression in transfected cells (**p<0.0001, *p<0.001).
Figure 11:
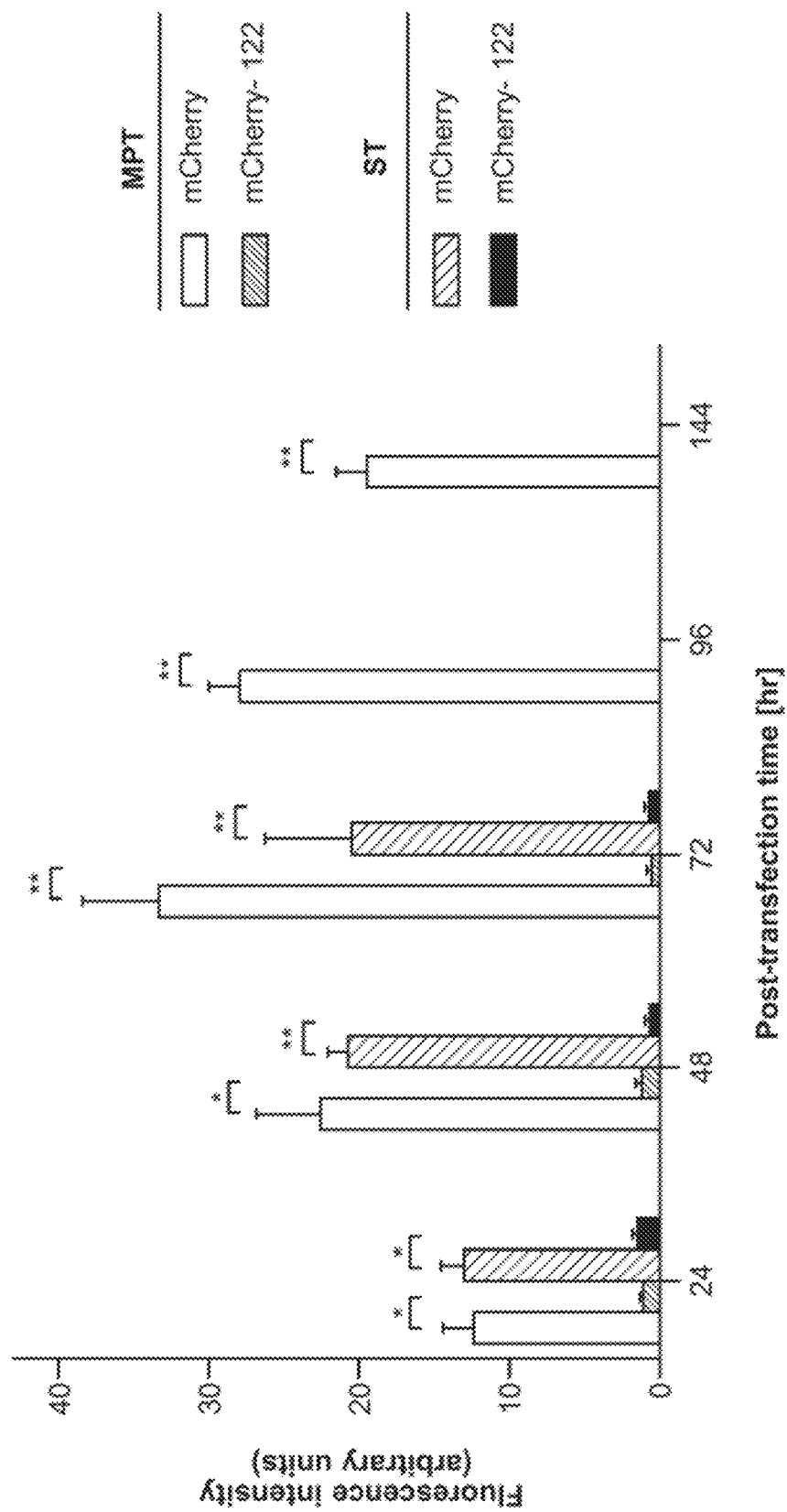
FIG. 11 shows a graph of results from an experiment in which human hepatocytes (HMCPP5) were transfected either multiple times (MPT) or singly (ST) with the delivery particles used in FIG. 10A. Expression of mCherry is determined by the level of fluorescence intensity measured at 24, 28, 72, 96 and 144 hours after transfection. Results are shown as means±SD. Statistical significance was determined using the t test. Asterisks indicate statistically significant difference between mRNA-mCherry, mRNA-mCherry-122 expression in transfected cells (*p<0.01, **p<0.05).

Quantification of the mCherry fluorescence signal was performed using ImageJ software (NIH, USA) from 3 randomized fields on culture plates (mRNA-mCherry, mRNA-mCherry-122). FIGS. 10B, 11 and 12B show the results of such quantifications. The pixel count of mCherry transfected wells were set at 100% (mCherry fluorescence). Statistical significance was determined using the Student t-test. Results are shown as means±SD. Significant difference was defined with p value <0.05. Asterisks indicate a statistically significant difference between mCherry fluorescence in cells transfected with mRNA-mCherry, compared to cells transfected with mRNA-mCherry-122 (**, $p<0.0001$, *$p<0.001$, **$p<0.01$, *$p<0.05$).

Example 1

Tumor-Specific Gene Expression by miRNA-122 Regulation miRNA-122 is an abundant, liver-specific miRNA, the expression of which is significantly decreased in human primary hepatocarcinoma (HCC) and HCC derived cell lines such as Hep3B and HepG2. The objective of this study was to demonstrate that modification of the 3'-untranslated region (UTR) of an mRNA sequence by the insertion of miRNA-122 targeted sequences (for example, SEQ ID NO: 2, as illustrated in variant 1, top of FIG. 3) may result in translational repression and/or deadenylation followed by decapping of exogenous mRNA in normal hepatocytes, but not in tested HCC cell lines.

To examine endogenous miRNA-122 activity in healthy hepatocytes, HMCPP5 cells (pooled plateable human hepatocytes, which are a mixture of plateable primary hepatocytes produced by combining cells from 5 individual donors) were transfected with mRNA-mCherry or mRNA-mCherry-122 prepared according to the above general protocols, using mCherry (red fluorescent protein) as the introduced gene of interest and followed mCherry (red fluorescent protein) expression over time. As illustrated in FIG. 10A, mCherry (mCh) expression was analyzed by fluorescence microscopy 48 hours post-transfection. During the entirety of the post-transfection time, mCherry expression was observed in HMCPP5 cells transfected with mRNA-mCherry (that is, without the 3'UTR modification to introduce an miR-122 sequence), indicating successful transfection and translation. In contrast, in healthy hepatocytes, which are known to be miRNA-122 positive, the expression of mRNA-mCherry-122 was downregulated to practically undetectable levels comparable to those seen in control untransfected cells, even 3 days after transfection. This indicated that the presence of an miRNA-122 targeted sequence in the mRNA-mCherry-122 inserted in 3' UTR (Variant 1) prevents translation of the mRNA, most likely due to translational repression in recipient cells.

Quantification of the fluorescence signal exhibited by these cells confirmed the above. As shown in FIG. 10B, fluorescence intensity was drastically reduced in healthy cells transfected with mRNA-mCherry-122, compared with those transfected with mRNA-mCherry.

The result obtained in the experiment above showed that native expression of miRNA-122 and colocalisation with an miRNA-122 targeted sequence (Variant 1) could efficiently regulate protein expression in healthy hepatocytes thereby significantly increasing tumor-specific gene expression. In the following experiment, the constitutive expression and activity of miRNA-122 in HMCPP5 cells was evaluated. The HMCPP5 cells were transfected with mRNA-mCherry or mRNA-mCherry-122 three times in total, with an interval of 48 hr each time. Six days after the first transfection (that is, 48 hours after the last transfection) expression of mCherry was determined by fluorescent microscopy. As before, while cells transfected with the mRNA-mCherry construct exhibited clear red fluorescence, those transfected with the mRNA-mCherry-122 construct did not. In FIG. 11, comparisons between cells transfected with mRNA-mCherry-122, and those transfected with mRNA-mCherry are shown over a five-day period after final transfection, both for singly (ST) and multiply-transfected cells (MPT). Multiply-transfected cells can be seen to exhibit the same drastic reduction in fluorescence intensity when transfected with mRNA-mCherry-122 as singly-transfected cells, with the effect lasting longer following multiple transfections. As would be expected, this indicates that the differential expression effect driven by the miRNA control mechanism is robust to repeated transfection events, and that the amount of miRNA-122 available within the cells to drive this mechanism is not exhausted in these timeframes.

To examine the effect of endogenous miRNA-122 activity using the human liver hepatocarcinoma Hep3B and hepatoblastoma HepG2 cell lines, an experiment similar to the above was carried out. Cells were transfected with the mRNA sequence mRNA-mCherry, mRNA-mCherry-122 (Variant 1), or underwent a control transfection. As previously, after 48 hours, fluorescence microscopy was used to determine the expression of mCherry in the transfected Hep3B and HepG2 cells, as shown in FIG. 10A. In Hep3B cells (FIG. 10A, middle column), mCherry fluorescence was clearly seen both in the mRNA-mCherry and the mRNA-mCherry-122 transfected lines, indicating that the miRNA-122 mediated translation repression is not active in these cells. In HepG2 cells, mCherry fluorescence was clearly seen in the mRNA-mCherry transfected line, but while some fluorescence was evident in the mRNA-mCherry-122 transfected cells, it appeared to be only partially reduced and significantly greater than that seen in normal hepatocytes. Further evidence of this is shown in FIG. 10B, where quantification of mCherry fluorescence in mRNA-mCherry-122 transfected lines indicates that no reduction of fluorescence is shown in Hep3B cells, but a reduction of around 50% is seen in the HepG2 cells.

The partial downregulation seen in HepG2 cells further implicates miRNA-122 mediated effects on translation, as cells from this line have been shown to retain residual miRNA-122 activity (Demonstration of the Presence of the "Deleted" MIR122 Gene in HepG2 Cells, PLoS One. 2015; 10(3)).

miRNA-122 is strongly conserved between vertebrate species, and, as in the human, a reduced level of miRNA-122 is associated with hepatocellular carcinoma in mouse (Kutay et al, 2006). The endogenous effect of miRNA-122 activity was therefore examined, using the mouse healthy hepatocyte cell line Aml12.

Healthy mice hepatocytes were also transfected with the mRNA-Cherry sequences previously described, i.e., mRNA-mCherry or mRNA-mCherry-122, encapsulated in $DMP^{CTx}$. A similar impact of the insertion of miRNA-122 binding site sequence on the mCherry fluorescence was observed at 24 and 72 hours after transfection.

Figure 12A:
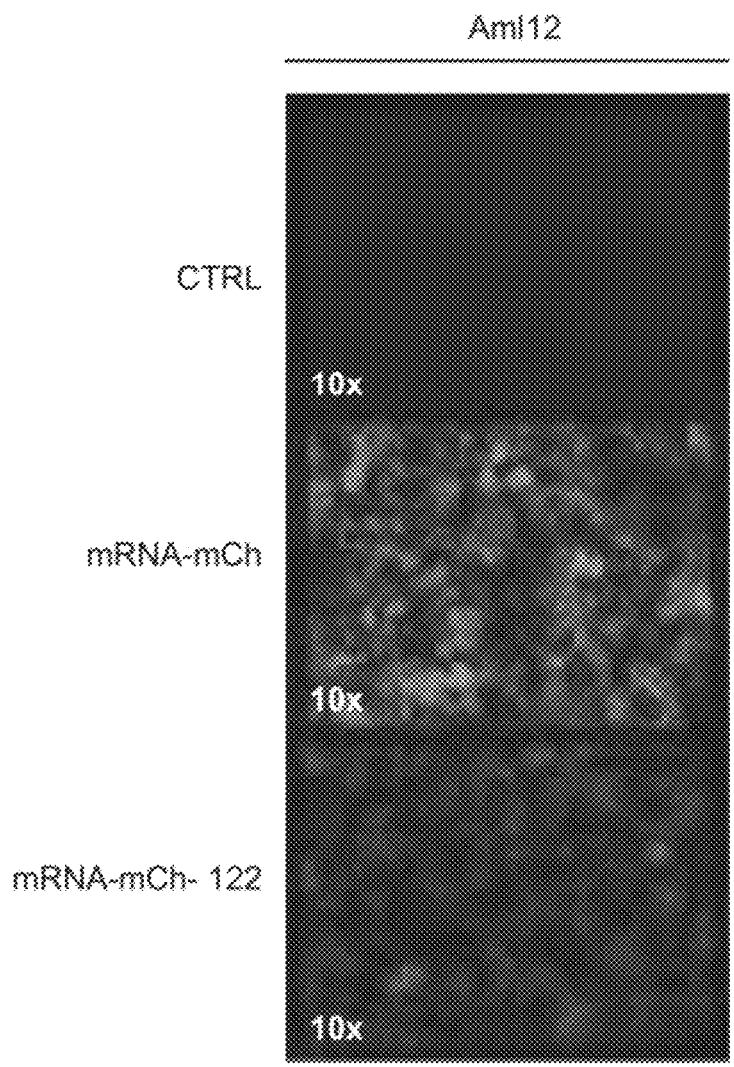
FIG. 12A shows fluorescent microscopy images indicating the results of an experiment where healthy mice hepatocytes (AML12 cell line) were transfected in vitro with the delivery particles used in FIG. 10A with relative expression levels of mCherry shown at 24 hours post transfection.
Figure 12B:
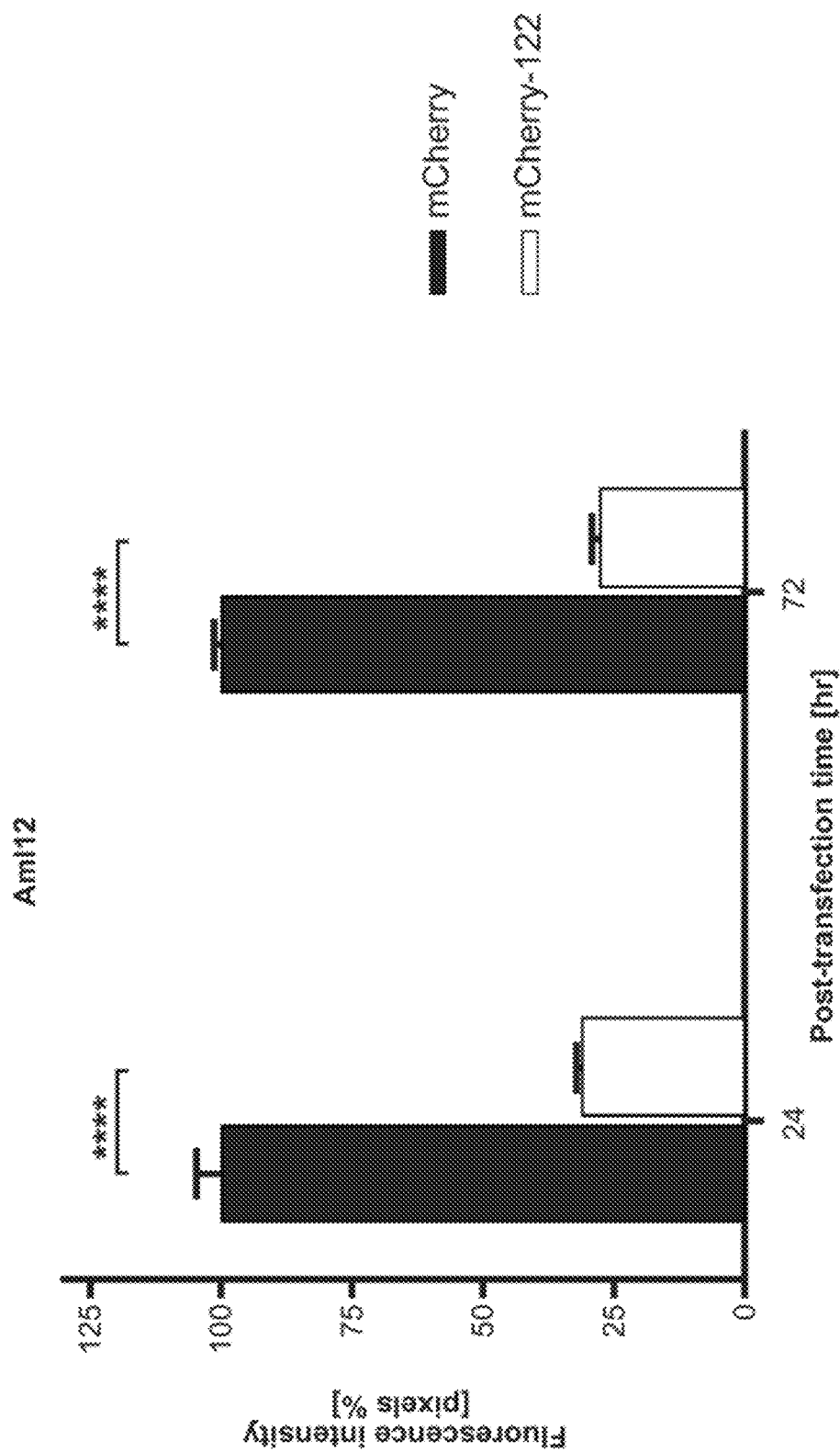
FIG. 12B shows a graph providing quantification of fluorescence intensity as % pixels counted for the results of FIG. 12A as well as a further post-transfection time point of 72 hours.

As shown in FIG. 12A, fluorescence was observed after transfection with mRNA-mCherry. A marked reduction in fluorescence was shown after transfection with mRNA-mCherry-122, although some signal could still be seen.

Quantification of mCherry fluorescence 24 and 72 hr after transfection was performed from 3 randomised fields on culture plates from each treatment group (FIG. 12B) showed that when transfected with mRNA-mCherry-122, more than 70% translation repression was observed.

As a preliminary conclusion, the above Example shows that the double targeting features of the nanoparticle delivery system, and the inclusion of miRNA-122 target sequence in the mRNA construct are sufficient to obtain quite significant differential expression of a protein product in hepatocarcinoma and hepatoblastoma cells compared to healthy hepatocytes. The observation of differential expression was evident in both human and mouse cell lines.

Example 2

Protein Expression Level After Tumor-Specific Gene Expression

In another experiment, Western blotting was employed to determine protein expression level ultimately exhibited after transfection as follows.

Transfection of Cell Lines and Immunoblot—Protein A

To evaluate tumor specific expression level of an exemplary 25 kDa human protein (denoted 'protein A') both liver cancer cells (HepG2 and Hep3B) and healthy hepatocytes (HMCPP5) were seeded into 12-well plates and transfected with 0.5 µg/well of nanoformulated mRNA expressing human protein A, 25 kDa (mRNA-A-$DMP^{CTx}$) or mRNA expressing human protein A (a human protein of approximately 25 kDa) comprising two miRNA122 binding sequences in the 3' UTR (SEQ ID NO: 2), Variant 1 (mRNA-A-miRNA122-$DMP^{CTx}$), as described above in Example 1 for mCherry transfection. 24 hours after transfection, immunoblot was performed following total protein extraction.

For the immunoblot, culture media was removed, cells were washed with cold PBS (Cellgro) and cell pellets lysed in RIPA (radioimmunoprecipitation assay) buffer (Boston Bioproducts) with a cocktail of protease inhibitors (Sigma). Protein concentration was determined by colorimetric Bradford assay. A total of 10 mg of protein was separated by Novex™ 4-12% mini gels (ThermoFisher Scientific) and transferred onto PVDF (polyvinylidene difluoride) membranes by electroblotting (iBlot® 2 Gel Transfer Device, Invitrogen). After blocking with 5% nonfat dry milk in TBS-Tween 20 (Boston Bioproducts), membranes were incubated at 4° C. overnight with anti-protein A antibodies (1:2000, Abcam), or β-actin (Cell Signaling), followed by incubation with appropriate HRP (horseradish peroxidase)-conjugated goat anti-rabbit secondary antibodies (1:10000; Abcam) for 1 hour at room temperature. Protein-antibody complexes were visualized and imagined using Clarity™ Western ECL Substrate (Bio Rad) and LI-COR® system (LI-COR), respectively.

Figure 13:
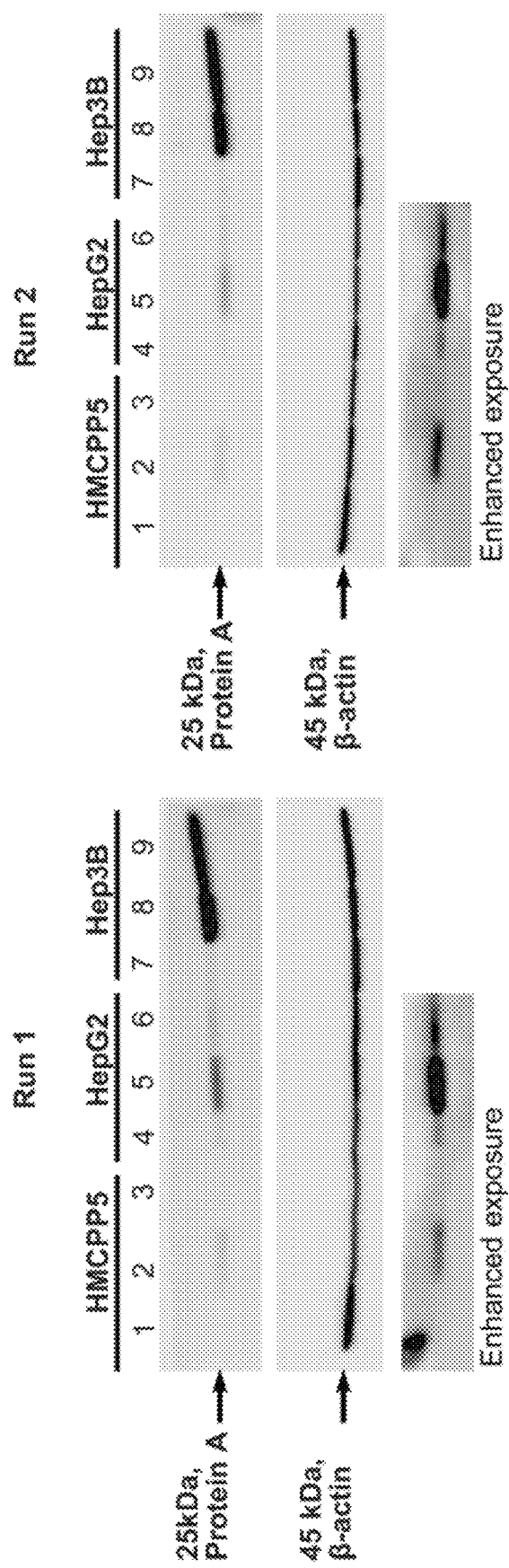
FIG. 13 shows the results of a Western blot in two experiments (denoted Run 1 and Run 2) where human hepatocytes (HMCPP5), human hepatoblastoma (HepG2) and human hepatocarcinoma (Hep3B) cells were transfected with a composition according to an embodiment of the invention which comprised an mRNA encoding an exemplary human polypetide of 25 kDa molecular mass under miRNA differential expression control.

The results of the above can be seen in FIG. 13, with the following transfection constructs encapsulated in DMP$^{CTx}$ shown:
- Lanes 1, 4 and 7 of FIG. 13: vehicle (mock treated, PBS only),
- Lanes 2, 5 and 8 of FIG. 13: mRNA-A (mRNA comprising the sequence for protein A), and
- Lanes 3, 6 and 9 of FIG. 13: mRNA-A-122 constructs (comprising the sequence for protein A and miRNA122, inserted in the variant 1 position, as illustrated in FIG. 3).

Transfection was carried out in healthy hepatocytes (HMCPP5) in lanes 1-3, hepatocarcinoma model Hep3B in lanes 7 to 9 and cells from the hepatoblastoma model HepG2 in lanes 4 to 6 as described above, using 0.5 µg mRNA-DMP$^{CTx}$ per well. Protein was extracted from each cell line 24 hours after transfection. 10 µg of protein was loaded into each lane, and data was taken from two independent experiments. Protein A was detected in all tested cell lines when transfected with mRNA-A, indicating that successful transfection was achieved. While transfected with mRNA-A-122, translation repression was observed only in healthy hepatocytes, but not in Hep3B and HepG2 cells (lanes 3, 6 and 9), indicating that the miRNA-122 does not fulfil its function in tested liver cancer cells. However, for HepG2 cells transfected with mRNA-A-122, expression of protein A was slightly downregulated compared to cells transfected with mRNA-A, similar to the pattern previously seen for mCherry expression, in Example 1. This can be seen clearly in the enhanced exposure photographs (bottom) which show incomplete downregulation in the HepG2 cells. The partial downregulation seen in HepG2 cells further implicates miRNA-122 mediated effects on translation, as cells from this line have been shown to retain residual miRNA-122 activity (Demonstration of the Presence of the "Deleted" MIR122 Gene in HepG2 Cells, PLoS One. 2015; 10(3)).

In summary, modification of 3'UTR mRNA by inserting liver-specific miRNA-122 target sequence can significantly confine mRNA translation to hepatocarcinoma Hep3B and hepatoblastoma HepG2, but not in normal human hepatocytes.

Example 3

Oncolytic Viral Combination Therapy In Vitro

It is described herein that the differential expression of provided mRNA constructs allowed by the method of the invention, and shown in the above Examples, can be used in combination with oncolytic viral therapy. In particular, where oncolytic viruses have been modified to remove virulence genes, attenuating their replicative ability in healthy cells, the invention can be used to restore the function of those genes, or equivalents thereof, in diseased cells such as cancer cells. To investigate this possibility, the combination of the oncolytic virus HSV-1 (R7041), deficient in US3 (see Leopardi et al, 1997, PNAS 94; 7891-7896), and the DMP$^{CTx}$ platform, providing an mRNA construct coding for US3, and modified with miRNA-122 binding sites, was used in a model of liver hepatocarcinoma (SEQ ID NO: 4).

General Protocols

Cell Culture

Human liver hepatocarcinoma (HCC) HepG2 and Hep3B cells were cultured in Eagle's Minimum Essential Medium (EMEM, Cellgro, USA), 10% FBS, streptomycin (100 µg/mL) and penicillin (100 U/mL-1) as monolayers, at 37° C. and in an atmosphere of 5% CO2. HepG2 cells were grown on collagen coated plates at a collagen concentration of 5 µg/cm2.

Virus Preparation

Frozen R7041 virus was thawed in a water bath at 37° C., and sonicated for 30 sec using a bath sonicator (Q500 sonicator, Qsonica, USA), then transferred to ice, ready for use.

Toxicity of R7041 Alone Against Human HCC

The US3 mutant R7041 virus is thought to be virtually apathogenic to healthy cells (Leopardi et al. 1997) and has even shown good safety in immunodeficient, athymic mice (Liu et al. 2007, Clin Cancer Res 2007; 13(19)). To establish a baseline of the efficacy of the R7041 virus against liver hepatocarcinoma cells, the model cell lines were treated with oncolytic virus alone. Cells from the Hep3B and HepG2 lines were seeded, in triplicate, into 96-well plates, at 15,000 and 17,000 per well, respectively.

24 hours later, cells were infected with 3-fold serial dilutions of virus, from MOI 0.37 to 0.0001694. 96 hours post-infection, the viability of tested cell lines was measured by MTS assay according to vendor instructions (CellTiter 96® AQueous One Solution Cell Proliferation Assay, Promega, USA). Absorbance was measured at 490 nm with a 96-well plate reader (BioTek, Cytation 3, USA). Dose-response curves and 50% effective dose values (ED$_{50}$) were obtained using GraphPad Prism, 7.03.

Figure 14:
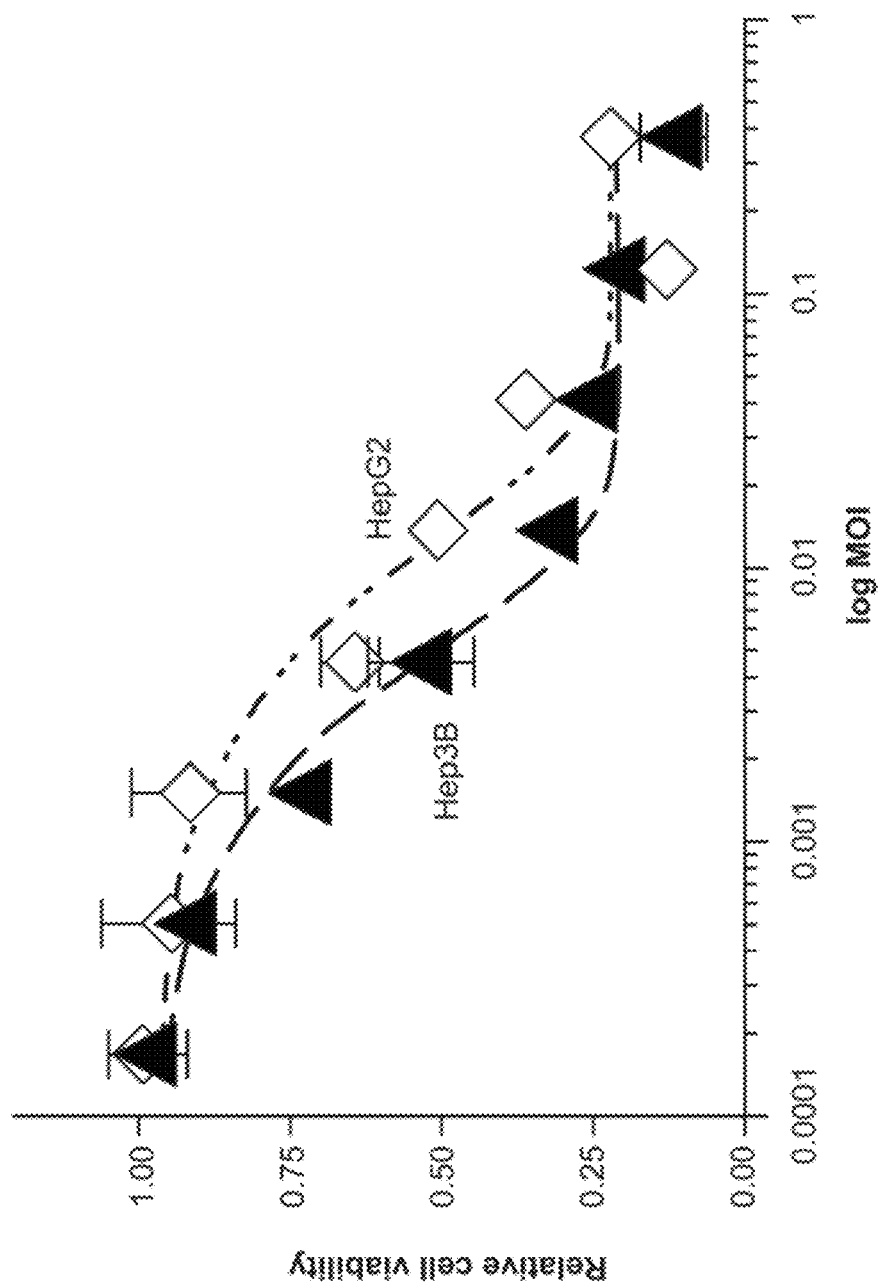
FIG. 14 shows the effect of the Herpes Simplex Virus variant R7041 on the viability of human cells from a model of hepatocarcinoma (Hep3B) and hepatoblastoma (HepG2). The effects of viral application on relative cell viability are shown.

As shown in FIG. 14, both Hep3B and HepG2 cell lines exhibited similar susceptibility to R7041, with ED$_{50}$=0.01 and 0.02 MOI, respectively. However, Hep3B cell lines were seen to be slightly more susceptible to R7041, than were HepG2 cells.

The Combinatorial Effect of R7041 and of mRNA-DMP$^{CTx}$ on Human HCC Viability Prior to evaluation of the combinatorial effect of R7041 virus and mRNA-US3-DMP$^{CTx}$ on human hepatocarcinoma cells, we verified that transfection of Hep3B and HepG2 cells with mRNA-US3-DMP$^{CTx}$ at 0.04 µg/mL mRNA-US3 has no significant effect on cell viability, as measured by the MTS assay.

Figure 15:
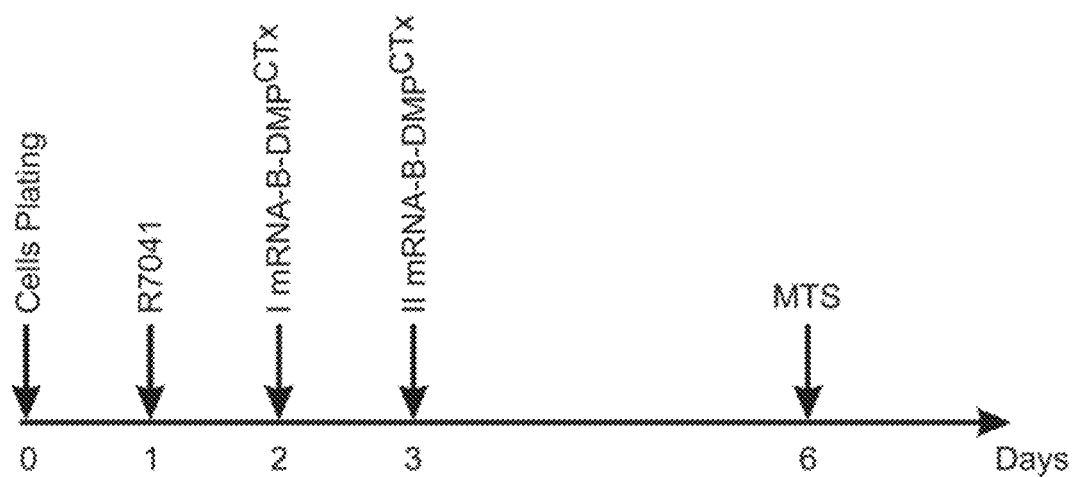
FIG. 15 shows a timetable for an in vitro experiment where human cells from a model of hepatocarcinoma were treated with a composition and method according to an embodiment of the invention and then tested via MTS colorimetric assay.

Hep3B and HepG2 cells were seeded in triplicate into 96-well plates at 15,000 and 17,000 per well, respectively. 24 hours later, cells were infected with 3-fold serial dilutions of virus, starting from MOI 0.37 up to 0.0001694. Both tested cell lines were transfected twice with a fixed dose of 0.04 µg/mL mRNA-US3-DMP$^{CTx}$, 24 and 48 hours after infection with R7041, according to the experiment timeline as shown in FIG. 15. Three days post-transfection, viability of tested cell lines was measured by MTS assay as described above. For both tested human HCCs, the combination of two different compounds: an oncolytic R7041 and a nontoxic dose of mRNA-US3-DMP$^{CTx}$ (0.04 µg/mL) significantly enhanced tumor destruction at lower viral titres, as shown in FIG. 16. In this figure, the effect on viability is shown for mRNA-US3-DMP$^{CTx}$ alone at 0.04 µg/mL (y-axis cross), for R7041 alone at various dilutions (grey triangles/diamonds) and for the combination (black circles).

The above Examples indicate that the combination of an attenuated oncolytic virus with deleted virulence genes, and a supply of differentially expressed replacements for the deleted genes can significantly increase the efficacy of oncolytic viral therapy in vitro. In particular, greater effects were seen at lower viral titres when in combination with the composition of the invention.

Example 4

Expression of Delivered Fluorescent Protein mCherry mRNA Constructs In Vivo

In order to determine the applicability of the invention for in vivo approaches, a mouse model of orthotopic human hepatocellular carcinoma was used. Differential expression of driven by miRNA-122 binding sites has been shown above (see Example 1) to be applicable in healthy mouse Aml12 liver cells in vitro.

Orthotopic Human Hepatocellular Carcinoma (HCC) Model
Animals

Female (CB17/Ics-PrkdcSCID/IcrIcoCrl) Fox Chase SCID mice at 6-8 weeks old, were purchased from Charles River, UK. All in vivo procedures were approved by the Subcommittee on Research Animal Care, at CrownBio in UK.

Cells

To generate an orthotopic HCC model, a bioluminescent variant of the human Hep3B cell line expressing firefly luciferase (Hep3B-cLuX) was used. Cells were cultured in EMEM medium (Sigma, UK) supplemented with 10% heat inactivated FBS, 2 mM L-Glutamine, 1% NEAA; Cells were treated weekly with 2 μg/mL Puromycin (Sigma).

Intrahepatic Injection and Tumor Growth Monitoring

Under anesthesia, human Hep3B-cLuX cells ($2 \times 10^6$) suspended in 20 μL of 1:1 PBS:Matrigel™ were injected in the upper left lobe of the liver using a 29 G needle. The injection site was covered using an absorbable gelatin sponge (AGS), the liver was placed back into the abdominal cavity without disturbing the AGS, and the skin was stitched closed. Tumor growth was checked twice weekly by bioluminescent imaging (BLI).

Briefly, the mice were anesthetised, and 150 mg/kg D-Luciferin was injected subcutaneously 15 minutes prior to imaging. BLI image was captured and processed using Living Image 4.3.1 software (Caliper LS, US). Mice were weighed three times weekly, or once weekly prior to dosing. On the indicated days, the mice were sacrificed, and the livers were fixed with 2 or 4% paraformaldehyde solution (PFA), before freezing in OCT (Optimal cutting temperature compound—embedding medium) for further histopathological analysis.

Formulation of mRNA and Evaluation of Tumor Targeting Efficiency mRNA sequences comprising the mCherry sequence, and the sequence of mCherry comprising miRNA-122 (SEQ ID NO: 3) were formulated as described above in the 'Synthesis of DMP$^{CTx}$ and formulation of mRNA' paragraph, and Table 4. To evaluate selective tumor targeting and the sparing of non-diseased liver cells, formulated mRNA was injected into the tail vein of mice bearing orthotopic liver cancer. Briefly, $2 \times 10^6$ of human Hep3B-cLuX cells suspended in 20 μL of 1:1 PBS:Matrigel™ were injected in the upper left lobe of the liver as described above. Tumor growth was then monitored by BLI imaging, also as above. Eight days later, when the tumor was established (BLI≥$6 \times 10^6$), 20 μg of formulated mRNA-mCherry-DMP$^{CTx}$, mRNA-mCherry-122-DMP$^{CTx}$ or mRNA-A-122-DMP$^{CTx}$ per mouse was injected through the tail vein, leading to the delivery particles being taken into the liver by returning blood flow. Twenty-four hours later last BLI was performed, mice were euthanised, and the livers were excised and imaged by BLI ex vivo at the localised liver lesions.

Histology

Briefly, following ex vivo imaging, left liver lobes with tumor were removed, fixed with 2% PFA, immersed in 30% sucrose solution (in PBS; pH7.4) at 4° C., embedded in OCT and frozen in isopentane pre-cooled with dry ice bath, and then stored at −80° C. 5 μm frozen sections (Leica CM300, USA) were subjected to nuclear counterstain with DAPI (VECTASHIELD, Vector Laboratories, USA) or H&E (hematoxylin end eosin) staining. Tumor targeting was assessed by determination of mCherry vs mCherry-122 expression level in tumor and healthy liver using fluorescence microscopy and/or software. Tumourous and healthy tissue was determined by H&E staining.

Figure 17A:
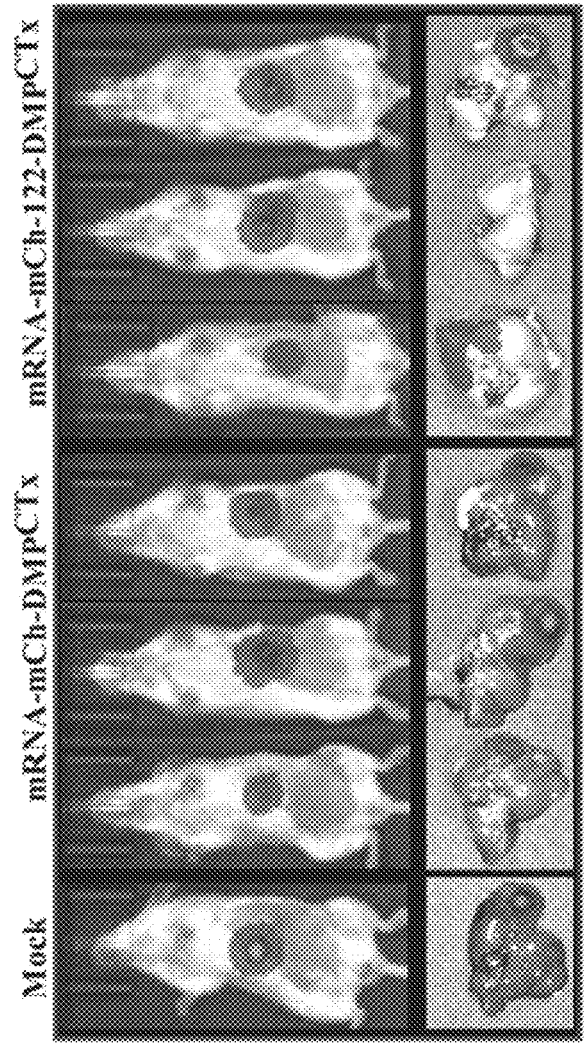
FIGS. 17A and 17B show the results of an in vivo experiments using a mouse model of human hepatocarcinoma.
Figure 17B:
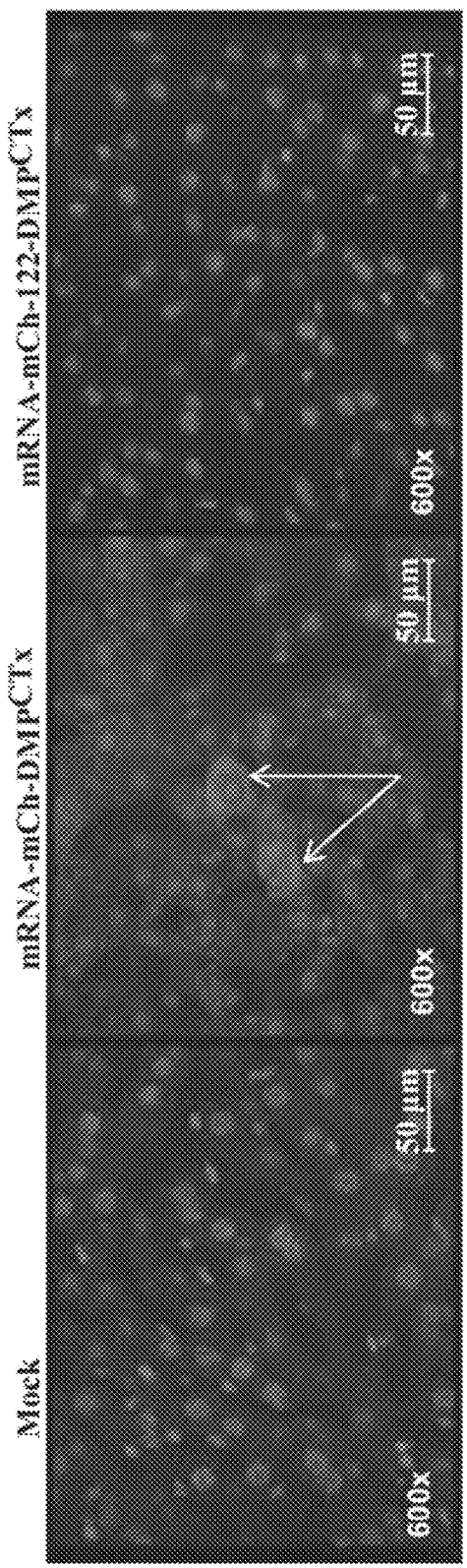

An example of tumor growth monitored by BLI imaging on mock and mRNA-mCherry-DMP$^{CTx}$, and mRNA-mCherry-122-DMP$^{CTx}$ treated mice. The animals were injected subcutaneously with D-luciferin, and imaged 15 min later. Signal was present in the midsection of the animals only as shown in FIG. 17A (upper panel), animals shown are prior to treatment with compositions. All animals with similar intensities in the midsection were dissected, and the livers were imaged ex vivo, FIG. 17A (lower panel). The left lobe of liver with tumour was sectioned and counter-stained with DAPI. Fluorescence microscopy was used to determine the expression of mCherry in healthy liver cells, and in liver tumour cells, 24 hours after injection of formulated mRNA, as shown in FIG. 17B. mCherry fluorescence was detected in healthy hepatocytes when mice were treated with mRNA-mCherry-DMP$^{CTx}$ (FIG. 17B, middle panel). When treated with mRNA-mCherry-122-DMP$^{CTx}$ (Variant 1), translation repression was observed (FIG. 17B, left panel) FIG. 17B shows healthy liver cells from (left to right), mock treated, mRNA-mCherry-DMP$^{CTx}$, and mRNA-mCherry-122-DMP$^{CTx}$ mice.

In conclusion, the compositions of the invention can be administered in vivo and can successfully transfect targeted liver cells. When modified with miRNA binding sites, differential expression can be achieved in non-diseased and tumoural cells.

Example 5

Figure 18:
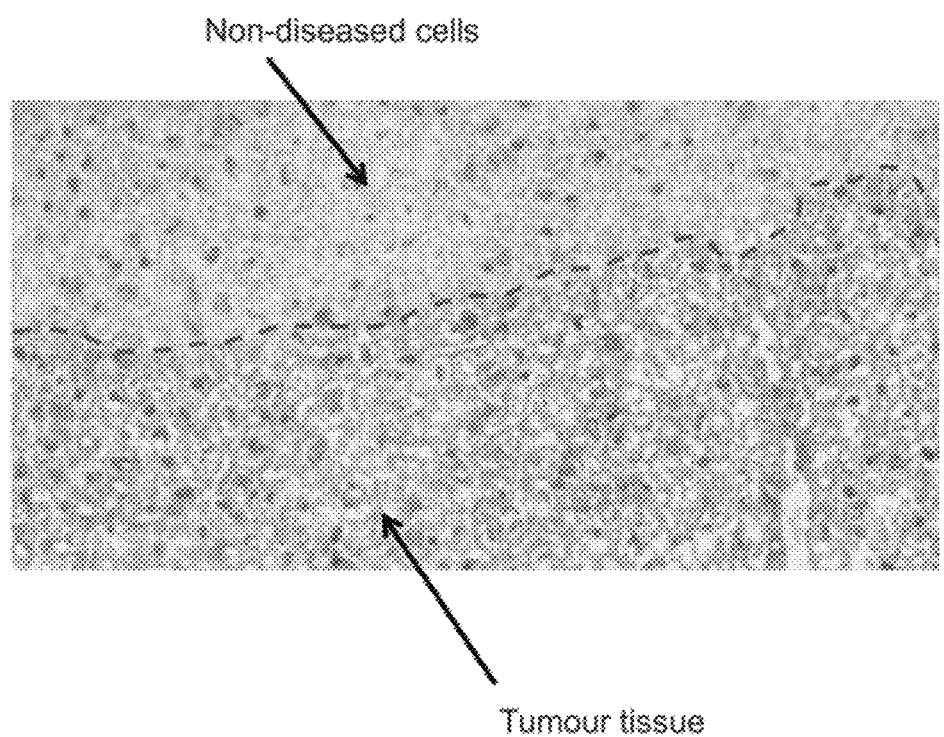
FIG. 18 shows an immunohistochemistry micrograph result of an in vivo experiment using the same mouse model as shown in FIG. 17A. A delivery particle comprising mRNA coding for US3 (US3 mRNA DMP$^{CTx}$ miRNA-122) is administered via the tail vein and provides differential expression between non-diseased hepatocytes and tumoural liver tissue as evidenced by darker staining for US3 protein in the tumoural tissue. The boundary between the tumour tissue and the non-diseased tissue is shown with a dashed line.

Differential Expression of Delivered US3 mRNA Construct In Vivo Between Non-Diseased and Diseased Tissue in the Liver The in vivo mouse model described in Example 4 was applied to administration of a delivery particle composition comprising a US3 mRNA DMP$^{CTx}$ miRNA-122 construct. Differential expression of US3 in the livers of mice containing Hep3B human cancer was analysed using immunohistochemistry with an anti US3 polyclonal antibody. The results are shown in FIG. 18, where it can be seen that there is a visible difference in US3 protein levels between the tumour (darker staining) and non-diseased cells (lighter staining). The differential expression tracks the boundary of the tumour, as independently verified by a pathologist. It can be concluded, therefore, that the compositions of the invention can successfully drive differential expression of a potential therapeutic enhancement factor in vivo in a mammalian subject.

Immunohistochemistry

Fresh frozen sections were cut at 5 μm (microns) and air-dried for approximately one hour prior to fixation with 4% paraformaldehyde at room temperature (RT) for 15 minutes. Sections were washed in running tap water and transferred to PBS-0.1% Tween. Sections were incubated with 2.5% normal horse serum (ready to use, ImmPRESS HRP anti-rabbit IgG peroxidase polymer detection kit, Vector MP-7401) for 20 minutes. The slides were drained and incubated with primary antibody to US3 diluted 1:400 (Acris AP55266SU-N). The antibodies were diluted with PBS-0.1% Tween and negative controls were included where the primary antibody was omitted and slides incubated with the antibody diluent PBS-0.1% Tween for one hour at RT. Slides were washed with PBS-0.1% Tween and endogenous peroxidase blocked with 0.3% hydrogen peroxide diluted with elga water for 10 minutes. Slides were washed with PBS-0.1% Tween and incubated with ImmPress anti-rabbit IgG reagent (ready to use, ImmPRESS HRP anti-rabbit IgG peroxidase polymer detection kit, Vector MP-7401) for 30 minutes at RT. Slides were washed with PBS-0.1% Tween and incubated for 5 minutes with chromogen ImmPACT DAB (ImmPACT DAB Peroxidase (HRP) Substrate, Vector SK-4105) then washed with elga water and counterstained as appropriate with Mayer's haematoxylin. A further wash in elga water briefly was carried out and blue in running tap water for 5 minutes. The slides were dehydated, cleared and mounted (95% IMS, 99% IMS ×2 and xylene ×2) then covered with a coverslip.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims.

What is claimed is:

1. A composition comprising at least two delivery particles comprising: a first delivery particle, wherein the first delivery particle comprises a first mRNA sequence complexed with, encapsulated by, or otherwise associated with the first delivery particle, the first mRNA sequence comprising a coding sequence which codes for tumor-associated antigen, an untranslated region (UTR) sequence; at least three micro-RNA (miRNA) binding site sequences, wherein the at least three miRNA binding site sequences are comprised of substantially different sequences and located within, immediately 5' to, or immediately 3' to, the UTR sequence; and a second delivery particle, wherein the second delivery particle comprises a second mRNA sequence complexed with, encapsulated by, or otherwise associated with the second delivery particle, the second mRNA sequence comprising a coding sequence which codes for an immunomodulatory molecule, an UTR sequence; at least three micro-RNA (miRNA) binding site sequences, wherein the at least three miRNA binding site sequences are comprised of substantially different sequences and located within, immediately 5' to, or immediately 3' to, the UTR sequence, and wherein upon administration to a subject, the composition stimulates an immune response to the tumor-associated antigen.

2. The composition of claim 1, wherein the first and/or second mRNA sequence comprises greater than four miRNA binding site sequences.

3. The composition of claim 1, wherein the at least three miRNA binding site sequences provide for differential expression of the coding sequence between a first and a second cell type comprised within a target organ selected from the group consisting of liver; brain; lung; breast; and pancreas.

4. The composition of claim 1, wherein the at least three miRNA binding site sequences comprise one or more miRNA-122 binding site sequences.

5. The composition of claim 1, wherein the first and second delivery particles comprise aminoalcohol lipidoids.

6. The composition of claim 5, wherein the first and second mRNA sequences are encapsulated by the first and second delivery particles, respectively.

7. The composition of claim 1, wherein the second mRNA codes for an immunomodulatory molecule selected from the group consisting of:
  (i) cytokines involved in immune response and inflammation selected from one or more of: TNF α, TNFβ, IFNα, IFNβ, IFNgamma, IL1, IL2, IL3, IL4, IL5, IL6, IL7, IL8, IL9, IL10, IL11, IL12, CCL 2, CCL3, CCL4, CCL5 CXCL 9, and CXCL10;
  (ii) dendritic cell activators selected from one or more of: GM-CSF, TLR7 and TLR9;
  (iii) molecules targeting the following cellular receptors and their ligands selected from one or more of: CD40, CD40L, CD160, 2B4, Tim-3, GP-2, B7H3 and B7H4;
  (iv) TGF β inhibitors;
  (v) T-cell membrane protein 3 inhibitors;
  (vi) inhibitors of programmed death 1 (PD1), programmed death-ligand 1 (PDL1), programmed death-ligand 2 (PDL2), cytotoxic T-lymphocyte antigen 4 (CTLA4), and lymphocyte-activation gene 3 (LAG3); and
  (vii) NF-κB inhibitors.

8. The composition of claim 7, wherein the second mRNA codes for IL12.

9. The composition of claim 7, wherein the second mRNA codes for GM-CSF.

10. A method of treating cancer in a subject comprising: systemically administering to the subject a composition as in one of claim 2-4 or 1-9, thereby treating the subject.

* * * * *